(12) United States Patent
Edwards et al.

(10) Patent No.: US 9,845,187 B2
(45) Date of Patent: Dec. 19, 2017

(54) AEROSOL DISPENSER WITH REPLACEABLE CARTRIDGE

(71) Applicant: AeroDesigns, Inc., Cambridge, MA (US)

(72) Inventors: David A. Edwards, Boston, MA (US); Cecily Lalor, Arlington, MA (US); Richard L. Miller, Needham, MA (US); Gavin McKeown, Bedford, MA (US)

(73) Assignee: AERODESIGNS, INC., Cambridge, MA (US)

( * ) Notice: Subject to any disclaimer, the term of this patent is extended or adjusted under 35 U.S.C. 154(b) by 1206 days.

(21) Appl. No.: 13/911,947

(22) Filed: Jun. 6, 2013

(65) Prior Publication Data

US 2013/0327327 A1    Dec. 12, 2013

Related U.S. Application Data

(60) Provisional application No. 61/656,507, filed on Jun. 6, 2012, provisional application No. 61/733,376, filed
(Continued)

(51) Int. Cl.
*A61M 16/00* (2006.01)
*B65D 83/14* (2006.01)
*A61M 15/00* (2006.01)

(52) U.S. Cl.
CPC ....... *B65D 83/753* (2013.01); *A61M 15/0016* (2014.02); *A61M 15/0028* (2013.01);
(Continued)

(58) Field of Classification Search
CPC .......... A61M 15/0028; A61M 15/0016; A61M 15/0043; A61M 2202/064; A61M 2205/128; B65D 83/753
(Continued)

(56) References Cited

U.S. PATENT DOCUMENTS 2,642,063 A    6/1953  Brown
3,906,950 A *  9/1975  Cocozza ........... A61M 15/0028
                                              128/203.15
(Continued)

FOREIGN PATENT DOCUMENTS

GB          2418147          3/2006

OTHER PUBLICATIONS

Invitation to Pay Additional Fees from the International Searching Authority dated Oct. 10, 2013 from Corresponding PCT Application No. PCT/US2013/044572.
(Continued)

*Primary Examiner* — Theodore Stigell
(74) *Attorney, Agent, or Firm* — McDermott Will & Emery LLP

(57) ABSTRACT

Aerosolizing delivery apparatuses can include cartridges configured to be detachably connected to a delivery device. The cartridges can include: a housing defining a reservoir and a cartridge outlet, the cartridge outlet configured to permit fluid communication between the reservoir and an exterior of the cartridge. A surface of the housing can be configured to define a bypass port between the housing and a surface of the delivery device when the cartridge is assembled with the delivery device.

24 Claims, 31 Drawing Sheets

Related U.S. Application Data on Dec. 4, 2012, provisional application No. 61/765,259, filed on Feb. 15, 2013, provisional application No. 61/781,786, filed on Mar. 14, 2013.

(52) U.S. Cl.
CPC ... *A61M 15/0043* (2014.02); *A61M 2202/064* (2013.01); *A61M 2205/128* (2013.01)

(58) Field of Classification Search
USPC .................................................. 128/203.15
See application file for complete search history.

(56) References Cited

U.S. PATENT DOCUMENTS

| | | | |
|---|---|---|---|
| 5,619,985 A * | 4/1997 | Ohki ................. | A61M 15/0028 128/203.15 |
| 2002/0078831 A1 * | 6/2002 | Cai ....................... | A47J 31/14 99/295 |
| 2004/0182387 A1 * | 9/2004 | Steiner .............. | A61M 15/0028 128/203.15 |
| 2009/0114220 A1 | 5/2009 | Wachtel et al. | |

OTHER PUBLICATIONS

Assembled, Rendering 1.
Exploded, Rendering 1.
Exploded, Cross-Section.
Exploded, Rendering 2.
Piece 2—Rendering.
Assembled, Top Side Perspective 1.
Assembled, Top Side Perspective 2.
Assembled Top Side.
Piece 1, First End Perspective.
Piece 1, Second End Perspective.
Piece 1, Top Side Perspective.
Piece 1, Top Side.
Piece 2, First End Perspective.
Piece 2, Second End Perspective.
Piece 2, Top Side 1.
Piece 2, Top Side 2.
Piece 3, First End Perspective.
Piece 3, Second End Perspective.
Piece 3, Top Side.

\* cited by examiner

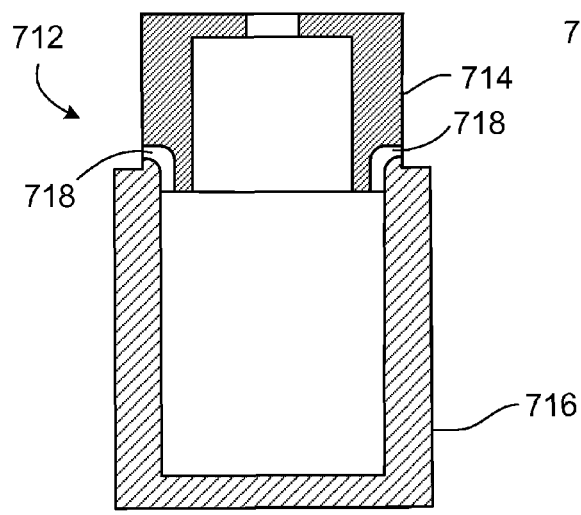
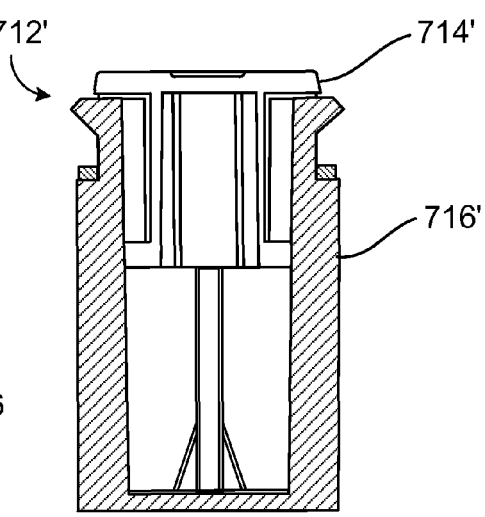
FIG. 1C  FIG. 2B
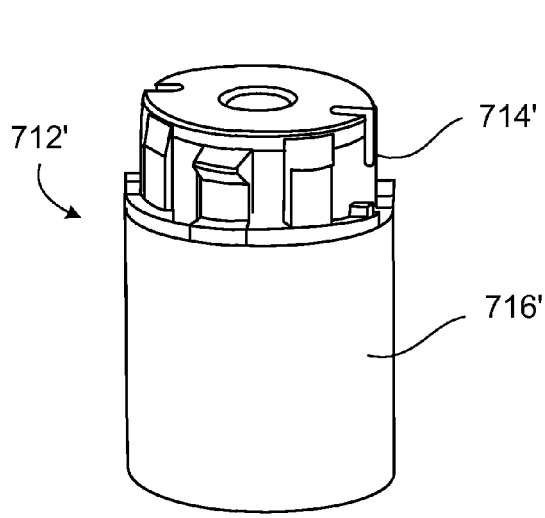
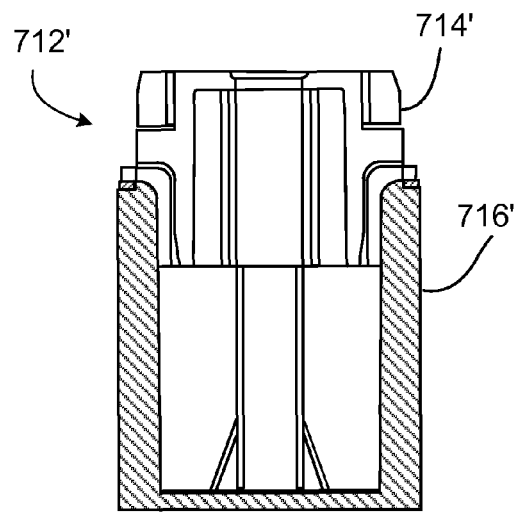
FIG. 2A  FIG. 2C

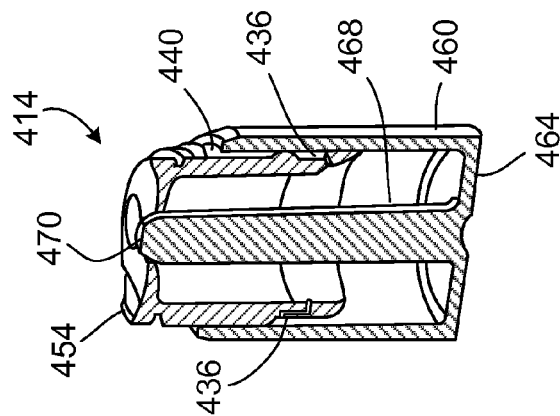
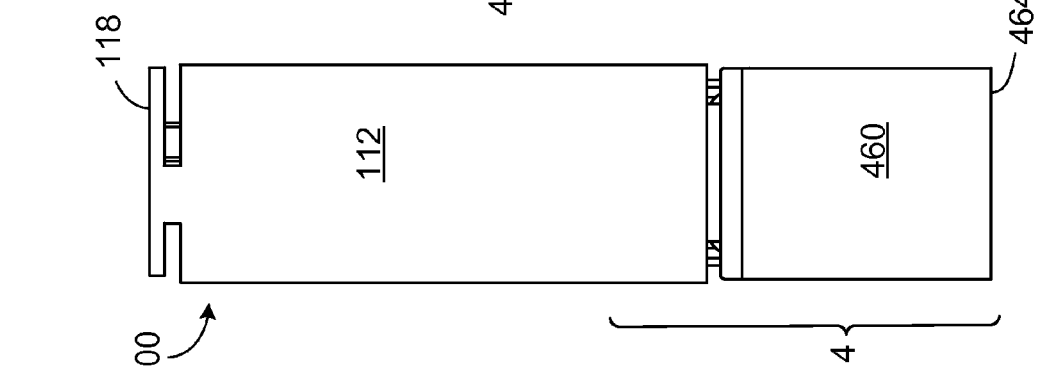
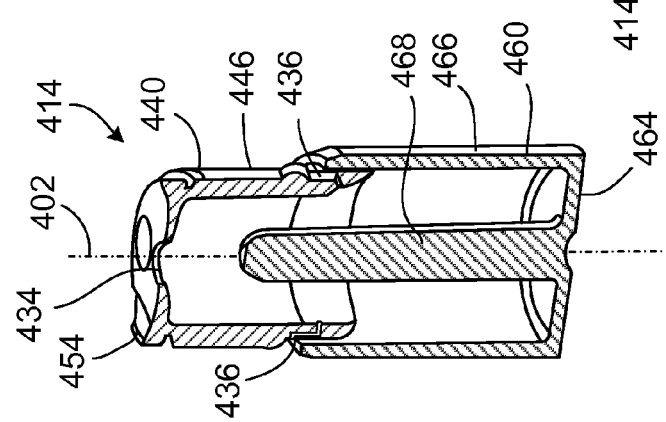
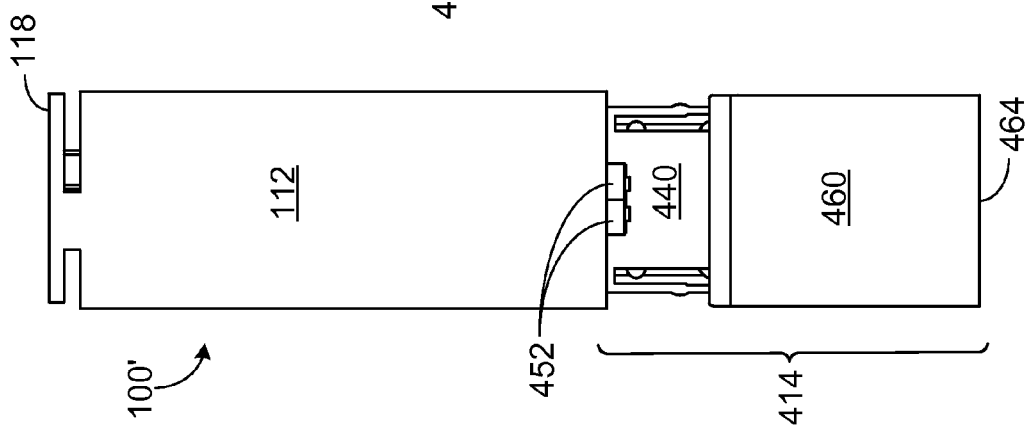

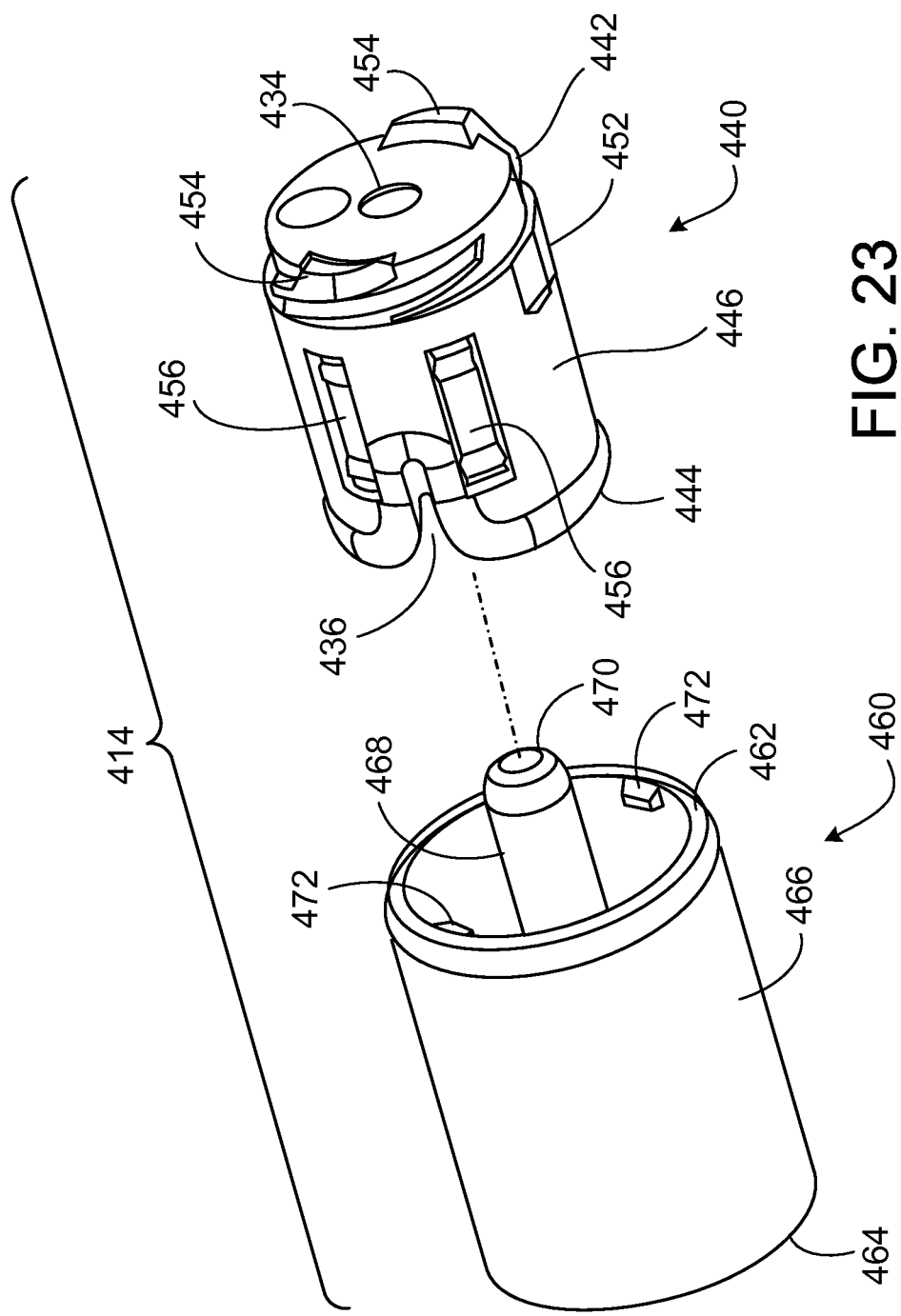

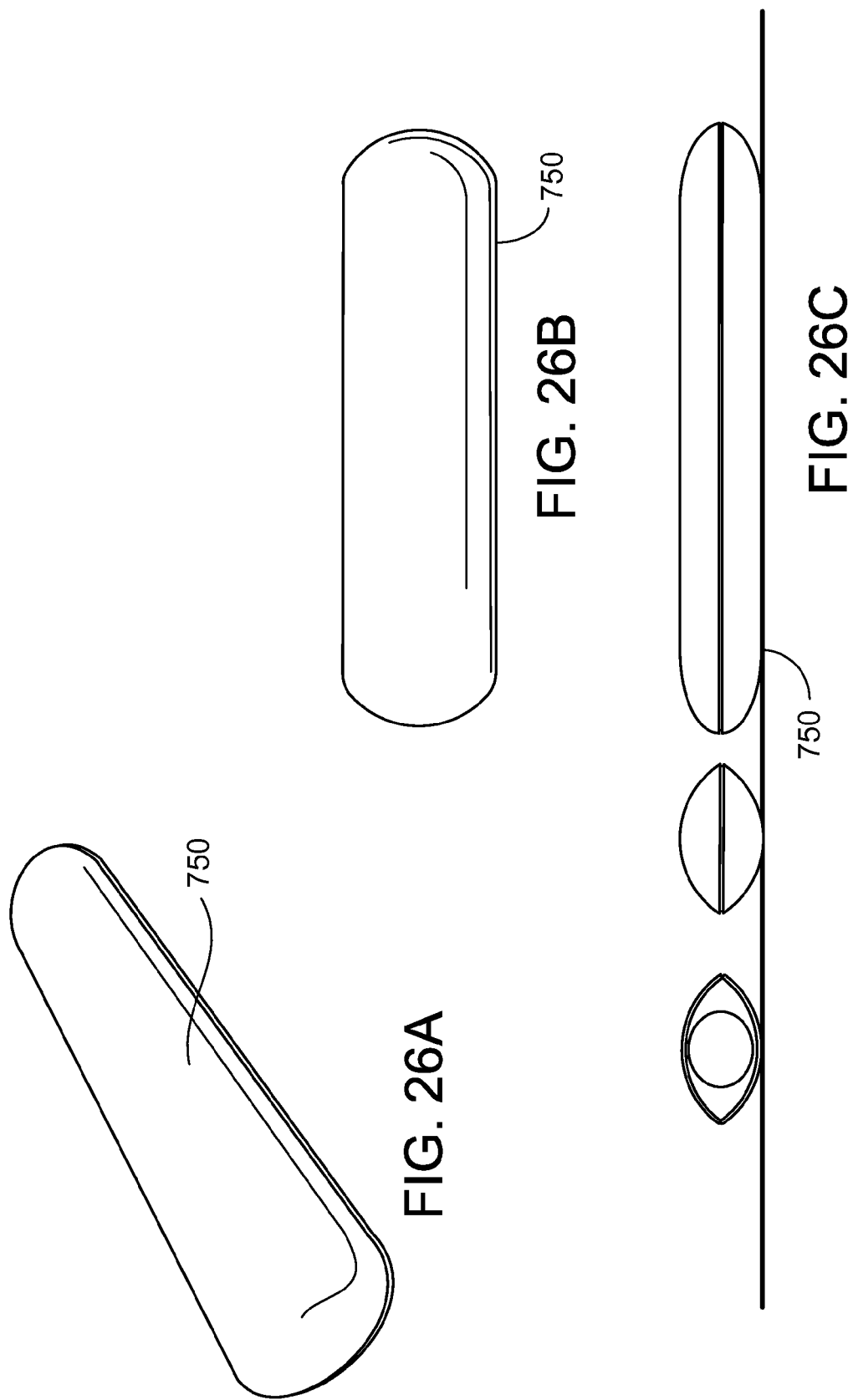

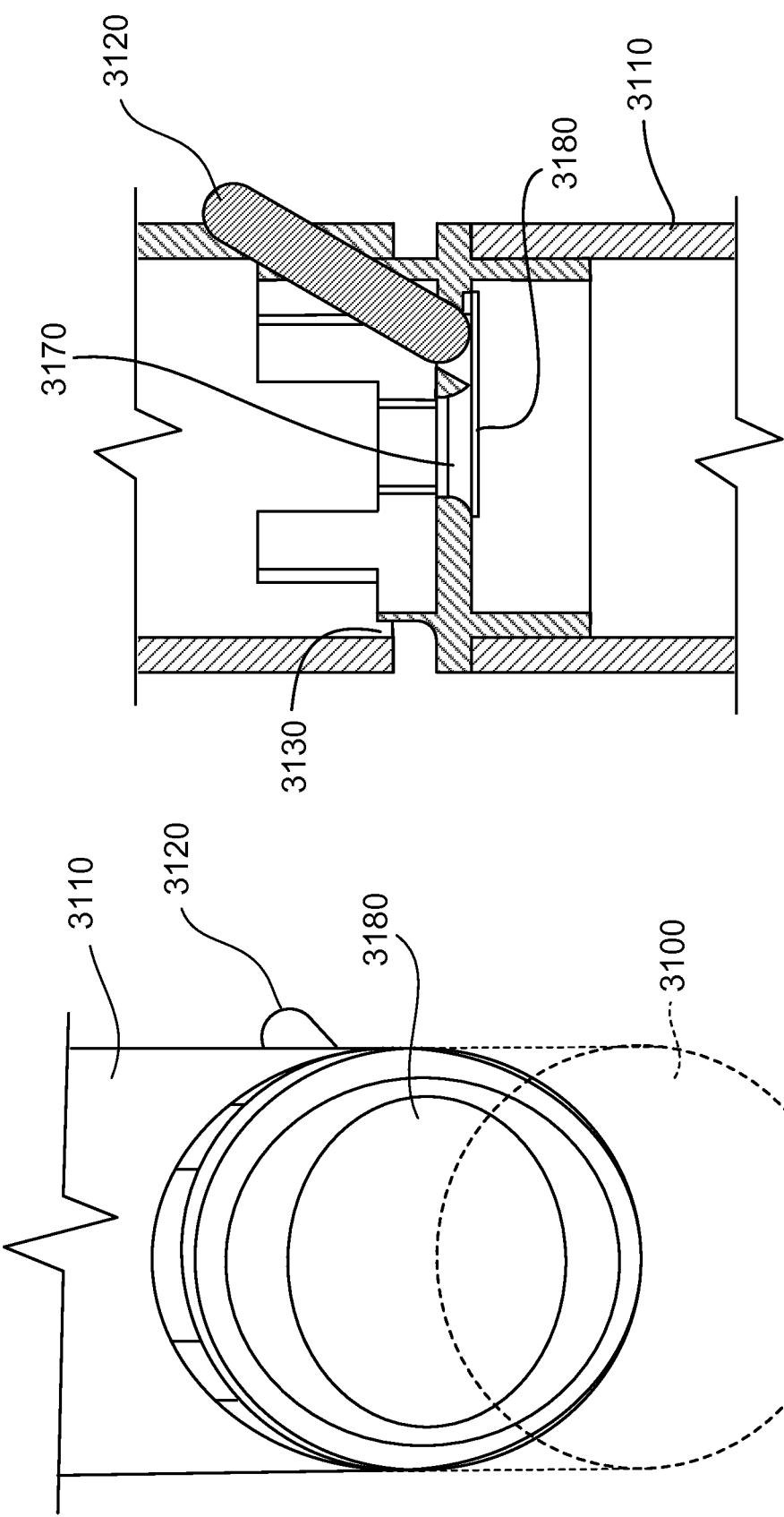

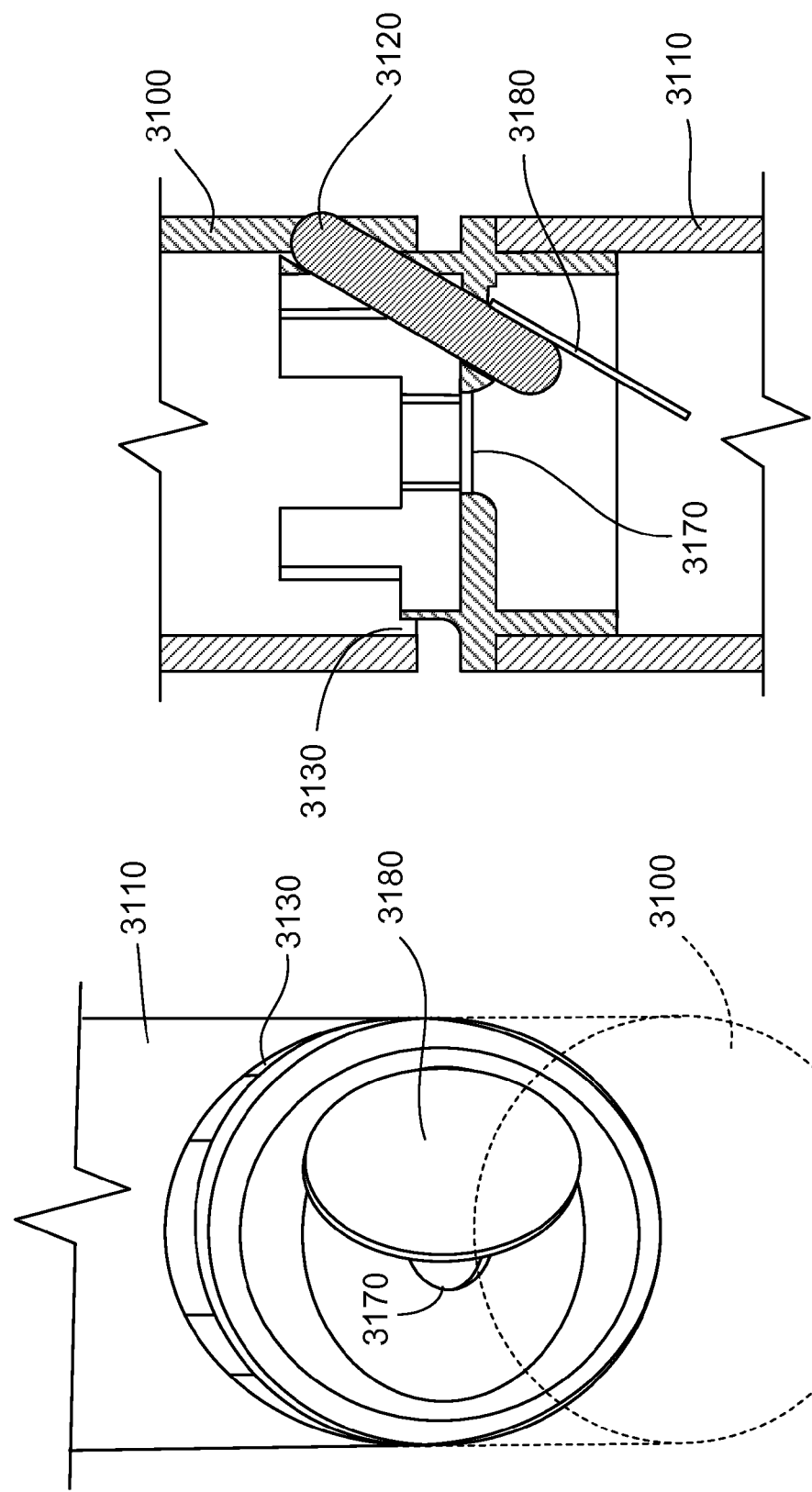

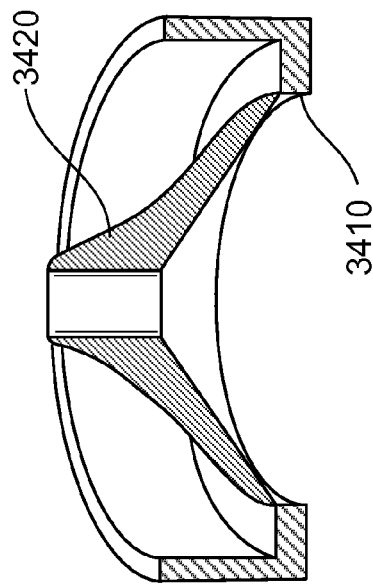
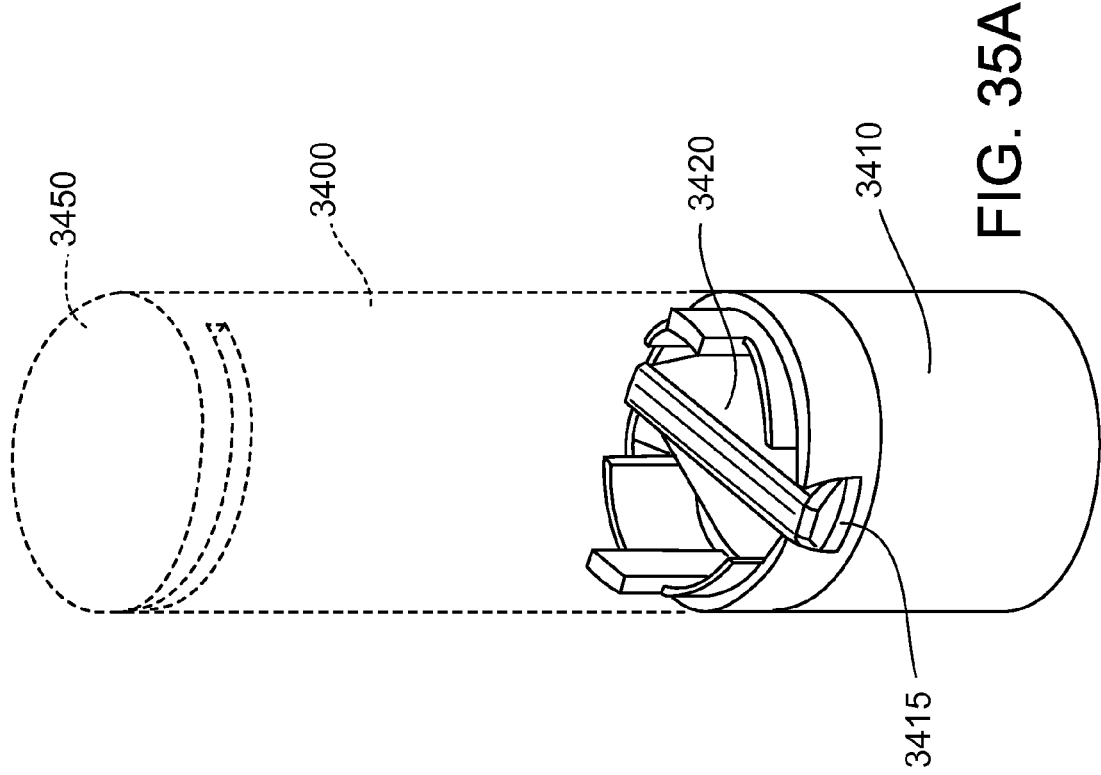
FIG. 35B
FIG. 35A

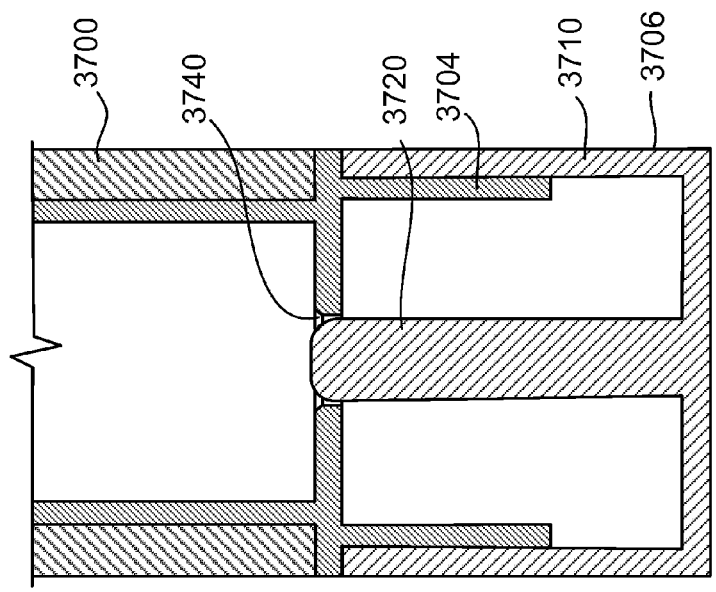
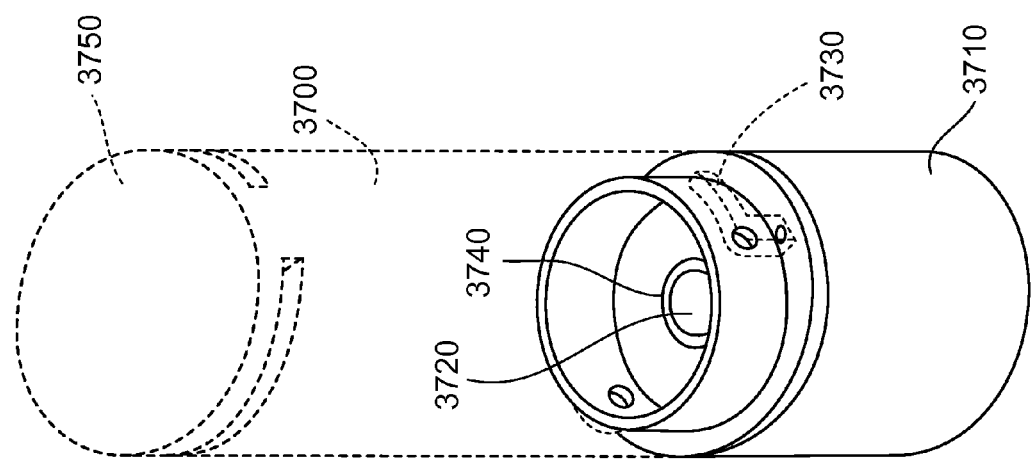
FIG. 37B
FIG. 37A

AEROSOL DISPENSER WITH REPLACEABLE CARTRIDGE

CROSS-REFERENCE TO RELATED APPLICATION

This application claims benefit from U.S. Provisional Application No. 61/656,507, filed Jun. 6, 2012, U.S. Provisional Application No. 61/733,376, filed Dec. 4, 2012, U.S. Provisional Application No. 61/765,259, filed Feb. 15, 2013, U.S. Provisional Application No. 61/781,786, filed Mar. 14, 2013, the complete disclosure of which is incorporated herein by reference.

FIELD OF THE INVENTION

The invention relates generally to aerosolized particles and apparatus for the containment, aerosolization, and/or delivery thereof.

BACKGROUND

Previous researchers have demonstrated that aerosolized particles can be used to deliver substances to various parts of the body. Certain designs have been proposed for utilizing these particles for drug delivery, and devices and methods have been developed for the delivery of aerosolizable products and uses thereof.

SUMMARY

Light, consumable particles can be drawn into a user's mouth for deposition on surfaces of the mouth for consumption through transdermal surfaces and/or through the digestive tract (e.g., ingestion via intake into the stomach and gastrointestinal tract by means of enteral administration). However, when consuming particles that are sufficiently light to be drawn into a user's mouth by inhalation or exhalation, one must address the risk of those particles reaching the back of the mouth or lungs and causing coughing or other adverse events, especially when the goal is, for example, to provide taste, nourishment, dietary supplementation, and/or medicinal delivery, involving the mouth, tongue, etc.

Therefore, approaches to deliver materials to the mouth via the airborne route have largely (if not exclusively) focused on directed, non-breath-actuated delivery, where the force of the air current and size of the particles are such that particle trajectories are primarily limited to within the mouth.

We have developed an approach by which a casual or forced breathing maneuver (such as normal inhalation or exhalation) can lead to the delivery of food, drink, medicinal and/or various other particles to the mouth, in which the transport of these particles with the flowing air, to the back of the throat and to the lungs, is limited. By controlling the inertia and gravity of the particles (e.g., food particles), and by directing deposition forces, we can focus delivery of the particles towards surfaces of the mouth, not reaching the back of the throat and lungs.

In some aspects, a cartridge configured to be detachably connected to a delivery device includes a housing defining a reservoir and a cartridge outlet, and the cartridge outlet is configured to permit fluid communication between the reservoir and an exterior of the cartridge. A surface of the housing is configured to define a bypass port between the housing and a surface of the delivery device when the cartridge is assembled with the delivery device.

The cartridge may include one or more of the following features: When connected to the delivery device, the cartridge outlet is configured to be in fluid communication with an inlet of the delivery device. The housing defines a cartridge inlet that is in fluid communication with air exterior to the device. The cartridge inlet is defined by a junction of the cartridge and a surface of the delivery device. The cartridge inlet is in fluid communication with an interior space of the delivery device. The cartridge comprises a closing mechanism operatively connected to at least one of the cartridge inlet and the cartridge outlet. The closing mechanism is at least one of a post-in-hole structure, a spring-actuated door, a slide lever, a living hinge, a flap valve, a unidirectional valve, or combinations thereof. The cartridge further an actuator operatively connected to the closing mechanism. The cartridge comprises an inner member, and an outer member slidably interconnected to the inner member to define the reservoir. The housing defines a cartridge inlet that is in fluid communication with air exterior to the device, and the inner member is movable relative to the outer member, between a first position wherein at least one of the cartridge air inlet and the cartridge outlet are open, and a second position wherein at least one of the cartridge air inlet and the cartridge outlet are closed. The movement of the inner member relative to the outer member actuates the at least one of an air inlet closing mechanism and an outlet closing mechanism.

The cartridge may also include one or more of the following additional features: The cartridge is detachably connected to the delivery device by a mounting carriage, a press fit, a magnetic retaining mechanism, a twist mechanism, a snap mechanism, a screw mechanism, a bayonet mount mechanism, or combinations thereof. The cartridge reservoir has a volume capacity of between about ten (10) milligrams to about two (2) grams of a product. When connected to the delivery device, the cartridge and delivery device cooperate to permit a flow rate of between about ten (10) liters per minute and about sixty (60) liters per minute at a vacuum pressure of about four kiloPascals. The reservoir has a variable volume. The cartridge further includes a delivery device connection portion and a base portion assembled with the delivery device connection portion. The delivery device connection portion and a base portion defines the reservoir within the cartridge, and the delivery device connection portion is moveable relative to the base portion between a first position in which the reservoir has a first volume, and a second position in which the reservoir has a second volume. When the cartridge is in the first position, the cartridge outlet is open so as to permit fluid communication between the reservoir and the exterior of the cartridge via the cartridge outlet, and when the cartridge is in the second position, the cartridge outlet is closed. The cartridge is at least one of edible or biodegradable. The cartridge is edible and is formed of at least one of a starch, a grain-based food, a vegetable, a meat, a fruit, a dairy product, a sugary food, a nut, a confection, a plant product, processed edible products thereof, synthetic edible products thereof, or combinations of edible products thereof. The cartridge is edible and is formed of at least one of chocolate, bread, fruit, sugar, meat, pasta, processed forms thereof, or combinations thereof. The cartridge is biodegradable and is formed of at least one of a polyester, a polyhydroxyalkanoate, a polyanhydride, a polycaprolactone, a polydiaxonone, a polyglycolide, a polyhydroxybutyrate, a polylactic acid, a polypropylene carbonate, a polylactic-co-glycolic acid, a poly(3-hydroxybutyrate-co-3-hydroxyvalerate), a polyvinyl alcohol, a starch derivative, a cellulose derivative, a cellulose ester, a cellophane, an enhanced biodegradable plastic, compositional variants thereof, or combinations thereof.

In some aspects, a cartridge that is configured to be detachably connected to a delivery device includes a housing defining a reservoir, an outlet configured to permit fluid communication between the reservoir and an exterior of the cartridge, and a closer disposed on the housing, the closer moveable between a first position in which the outlet is open such that fluid communication exists between the reservoir and the exterior of the cartridge, and a second position in which the outlet is closed, wherein a surface of the housing is configured to define a bypass port between the housing and a surface of the delivery device when the cartridge is assembled with the delivery device.

The cartridge may include one or more of the following features: The housing includes a first end configured to be connected to the delivery device, a second end opposed to the first end, and a sidewall extending between the first end and the second end, the outlet is defined in the first end, and the closer comprises a door. The door includes a cover portion that overlies at least a portion of the first end, an actuating portion that extends from the cover portion and protrudes outward from the cartridge in a direction normal to the sidewall, and a spring mechanism disposed between the actuating portion and the sidewall, the spring mechanism biasing the door toward the second position. The closer comprises an umbrella valve that overlies the outlet. The closer comprises a cover plate that overlies the outlet, the cover plate including a cover plate opening, and the cover plate is rotatably connected to the housing in a manner such that when the cover plate is in the first position the cover plate opening is aligned with the outlet, and when the cover plate is in the second position the cover plate opening is not aligned with the outlet. The housing includes a connection portion that is configured to be detachably connected to the delivery device, the connection portion including a first end having the outlet opening, and a first sidewall about the first end, and a base portion including a second end, and a second sidewall about the second end. The closer extends from the second end in parallel with the second sidewall and with at least a portion of the closer inside the second sidewall, the connection portion is engaged with the base portion to define the reservoir, and the connection portion is moveable relative to the base portion between the first position in which the closer is spaced apart from the outlet, and the second position in which the closer resides within the outlet.

In some aspects, a cartridge for a delivery device includes a connection portion configured to be detachably connected to the delivery device. The connection portion includes a first end having an outlet, and a first sidewall disposed about the first end, and a base portion, the base portion including a second end, a second sidewall disposed about the second end, and a post extending from the second end in parallel with the second sidewall so that at least a portion of the post is surrounded by the second sidewall. The connection portion is engaged with the base portion to define a reservoir between the first end and the second end, and the connection portion is moveable relative to the base portion between a first position in which the outlet is open such that fluid communication exists between the reservoir and the exterior of the cartridge, and a second position in which the post is positioned within the outlet so as to close the outlet.

The cartridge may include one or more of the following features: An outer surface of the connection portion is configured to define a bypass port between the connection portion and a surface of the delivery device when the cartridge is assembled with the delivery device. The reservoir has a variable volume. The connection portion is engaged with the base portion such that when the connection portion is in the first position, an air inlet is formed between the connection portion and the base portion.

In some embodiments is an aerosolizing delivery apparatus comprising a first member defining a first interior volume, an inlet, an outlet, and an aerosol flow passage; a deflection member configured to be received in the mouth of a user, spaced apart from a plane that includes the first member outlet, positioned to redirect aerosol flow exiting the outlet toward one or more sides of the user's mouth; and a cartridge defining a second interior volume and detachably connectable to and in fluid communication with the first member, the cartridge defining at least one cartridge air inlet and at least one cartridge outlet, wherein the cartridge air inlet is in fluid communication with the second interior volume, and the outlet is in fluid communication with the second interior volume and the first member aerosol flow passage.

In some embodiments the first interior volume of the aerosolizing delivery apparatus defines the aerosol flow passage.

In some embodiments the of the aerosolizing delivery apparatus, the first member inlet is at least one of an air inlet, a bypass flow inlet, and an aerosol flow passage inlet.

In some embodiments of the aerosolizing delivery apparatus, the cartridge air inlet is in fluid communication with air exterior to the device.

In other embodiments of the aerosolizing delivery apparatus, the cartridge air inlet is defined by a junction of the first member and the cartridge.

In other embodiments of the aerosolizing delivery apparatus, the air inlet from first member is in fluid communication with the air inlet of the cartridge.

In some embodiments of the aerosolizing delivery apparatus, the cartridge is detachably connected to the first member by any one of a mounting carriage, a press fit, a magnetic retaining mechanism, a twist mechanism, a snap mechanism, screw mechanism, bayonet mechanism, or combinations thereof.

In certain embodiments of the aerosolizing delivery apparatus, the connection between the cartridge and the first member is lockable.

In certain embodiments, the aerosolizing delivery apparatus further comprises at least one cartridge bypass port.

In certain embodiments, the aerosolizing delivery apparatus further comprises at least one of a cartridge air inlet closing mechanism and a cartridge outlet closing mechanism.

In certain embodiments of the aerosolizing delivery apparatus, the cartridge air inlet closing mechanism is at least one of a post-in-hole structure, a spring-actuated door, a slide lever, a living hinge, a flap valve, a unidirectional valve, or combinations thereof.

In certain embodiments, the aerosolizing delivery apparatus further comprises an actuating mechanism operable on the cartridge air inlet closing mechanism.

In certain embodiments of the aerosolizing delivery apparatus, the cartridge outlet closing mechanism is at least one of a post-in-hole structure, a spring-actuated door, a slide lever, a living hinge, a flap valve, a unidirectional valve, or combinations thereof.

In certain embodiments, the aerosolizing delivery apparatus further comprises an actuating mechanism operable on the cartridge outlet closing mechanism.

In certain embodiments, the aerosolizing delivery apparatus further comprises at least one actuating mechanism is operable on the at least one cartridge air inlet closing mechanism and the outlet closing mechanism.

In certain embodiments of the aerosolizing delivery apparatus, the cartridge comprises an inner member and an outer member that slidably interconnect to define the second interior volume.

In certain embodiments of the aerosolizing delivery apparatus, the inner member is movable relative to the outer member, between a first position wherein at least one of the at least one of the cartridge air inlet port and the cartridge outlet port are open, and a second position wherein at least one of the at least one of the cartridge air inlet port and the cartridge outlet port are closed.

In certain embodiments of the aerosolizing delivery apparatus, movement of the inner member relative to the outer member actuates the at least one of an air inlet closing mechanism and outlet closing mechanism.

In certain embodiments of the aerosolizing delivery apparatus, the cartridge has a volume capacity of about ten (10) milligrams to about two (2) grams of an aersolizable product.

In certain embodiments the aerosolizing delivery apparatus is configured to permit a flow rate through the apparatus of between about five (5) liters per minute and about sixty (60) liters per minute at a vacuum pressure of about four kiloPascals.

In certain embodiments the aerosolizing delivery apparatus is configured for a flow rate through the apparatus of between about ten (10) liters per minute and about thirty (30) liters per minute at a vacuum pressure of about four kiloPascals.

In certain embodiments the aerosolizing delivery apparatus is configured for a flow rate through the apparatus of between about fifteen (15) liters per minute and about twenty-five (25) liters per minute at a vacuum pressure of about four kiloPascals.

In certain embodiments of the aerosolizing delivery apparatus, the cartridge contains an aerosolizable product.

In certain embodiments of the aerosolizing delivery apparatus, the cartridge contains at least one of a food product, an energy supplement, a pharmaceutical compound, an over-the-counter pharmaceutical compound, a nutraceutical, a sleep-aid compound, a weight-loss compound, or an oral health compound.

In certain embodiments of the aerosolizing delivery apparatus, the apparatus is at least one of edible or biodegradable.

In certain embodiments of the aerosolizing delivery apparatus, at least one of the first member and the deflection member is at least one of edible or biodegradable.

In certain embodiments of the aerosolizing delivery apparatus, the cartridge is at least one of edible or biodegradable.

In certain embodiments of the aerosolizing delivery apparatus, the cartridge is edible is formed of at least one of a starch, a grain-based food, a vegetable, a meat, a fruit, a dairy product, a sugary food, a nut, a confection, a plant product, processed edible products thereof, synthetic edible products thereof, or combinations of edible products thereof.

In certain embodiments of the aerosolizing delivery apparatus, the cartridge is edible and is formed of at least one of chocolate, bread, fruit, sugar, meat, bread, pasta, processed forms thereof, or combinations thereof.

In certain embodiments of the aerosolizing delivery apparatus, the cartridge is biodegradable and is formed of at least one of a polyester, a polyhydroxyalkanoate, a polyanhydride, a polycaprolactone, a polydiaxonone, a polyglycolide, a polyhydroxybutyrate, a polylactic acid, a polypropylene carbonate, a polylactic-co-glycolic acid, a poly(3-hydroxybutyrate-co-3-hydroxyvalerate), a polyvinyl alcohol, a starch derivative, cellulose esters, a cellophane, an enhanced biodegradable plastic, compositional variants thereof, or combinations thereof.

In certain embodiments of the aerosolizing delivery apparatus, an aerosolizing delivery apparatus configured to be connected to a cartridge, comprises: a first member defining a first interior volume, an inlet, an outlet, an aerosol flow passage, and a portion configured to be connected to the cartridge; and a deflection member configured to be received in the mouth of a user, spaced apart from a plane that includes the first member outlet, positioned to redirect aerosol flow exiting the outlet toward one or more sides of the user's mouth.

In certain embodiments of the aerosolizing delivery apparatus, the cartridge defines a second interior volume and detachably connectable to and in fluid communication with the first member, the cartridge defining at least one cartridge air inlet and at least one cartridge outlet, wherein the cartridge air inlet is in fluid communication with the second interior volume, and the outlet is in fluid communication with the second interior volume and the first member aerosol flow passage.

In certain embodiments of the aerosolizing delivery apparatus, the cartridge is detachably connected to the first member by any one of a press fit, a twist mechanism, a snap mechanism, screw mechanism, bayonet mechanism, or combinations thereof.

In certain embodiments of the aerosolizing delivery apparatus, the cartridge further comprises at least one cartridge bypass port.

In certain embodiments of the aerosolizing delivery apparatus, the cartridge has a volume capacity of about ten (10) milligrams to about two (2) grams of an aersolizable product.

In certain embodiments of the aerosolizing delivery apparatus, the cartridge contains an aerosolizable product.

In certain embodiments of the aerosolizing delivery apparatus, the aerosolizable product is at least one of a food product, an energy supplement, a pharmaceutical compound, an over-the-counter pharmaceutical compound, a nutraceutical, a sleep-aid compound, a weight-loss compound, or an oral health compound.

In certain embodiments of the aerosolizing delivery apparatus, the cartridge is edible.

In certain embodiments of the aerosolizing delivery apparatus, the cartridge is edible is formed of at least one of a starch, a grain-based food, a vegetable, a meat, a fruit, a dairy product, a sugary food, a nut, a confection, a plant product, processed edible products thereof, synthetic edible products thereof, or combinations of edible products thereof.

In certain embodiments of the aerosolizing delivery apparatus, the cartridge is edible and is formed of at least one of chocolate, bread, fruit, sugar, meat, bread, pasta, processed forms thereof, or combinations thereof.

BRIEF DESCRIPTION OF THE DRAWINGS

The advantages of the disclosure described below, as well as further advantages of the disclosure, can be better understood by reference to the description taken in conjunction with the accompanying figures, in which:

FIGS. 1A-C illustrate a particle delivery device having a disposable cartridge connected to a mouthpiece.

FIGS. 2A-C are views (perspective, cross-sectional, and cross-sectional, respectively) of a disposable cartridge of particle delivery device.

FIG. 19 is a side view of a particle delivery device including another alternative embodiment cartridge connected to a mouthpiece with the cartridge illustrated in an open configuration.

FIG. 20 is a perspective cross-sectional view of the cartridge of FIG. 19 in an open configuration.

FIG. 21 is a side view of the particle delivery device of FIG. 19 with the cartridge illustrated in a closed position.

FIG. 22 is a perspective cross-sectional view of the cartridge of FIG. 19 in a closed configuration.

FIG. 23 is an exploded perspective view of the cartridge of FIG. 19.

FIGS. 26A-C are views of a case for carrying a mouthpiece and associated capsules.

FIGS. 32A-32D illustrate an aerosolizing delivery apparatus that includes a user-actuated push button for actuating a flexible door to close outlet ports on a replaceable cartridge.

FIGS. 35A and 35B illustrate an aerosolizing delivery apparatus that includes a unidirectional duck bill valve used to close outlet ports on a replaceable cartridge.

FIGS. 37A-37D illustrate an aerosolizing delivery apparatus that includes a twist- or compression-actuated post-in-hole structure used to close inlet and outlet ports on a replaceable cartridge.

DETAILED DESCRIPTION

Figure 1A:
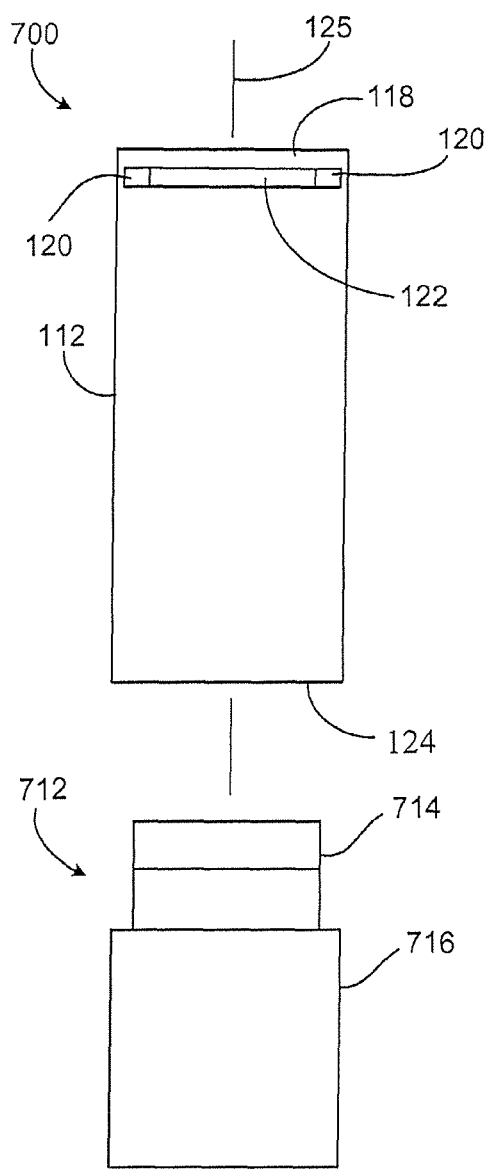
Figure 1B:
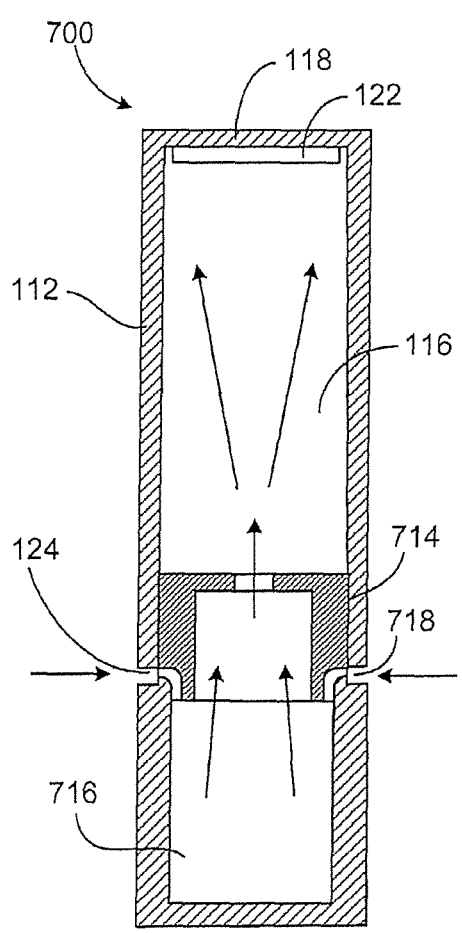
Figures 3A, 3B:
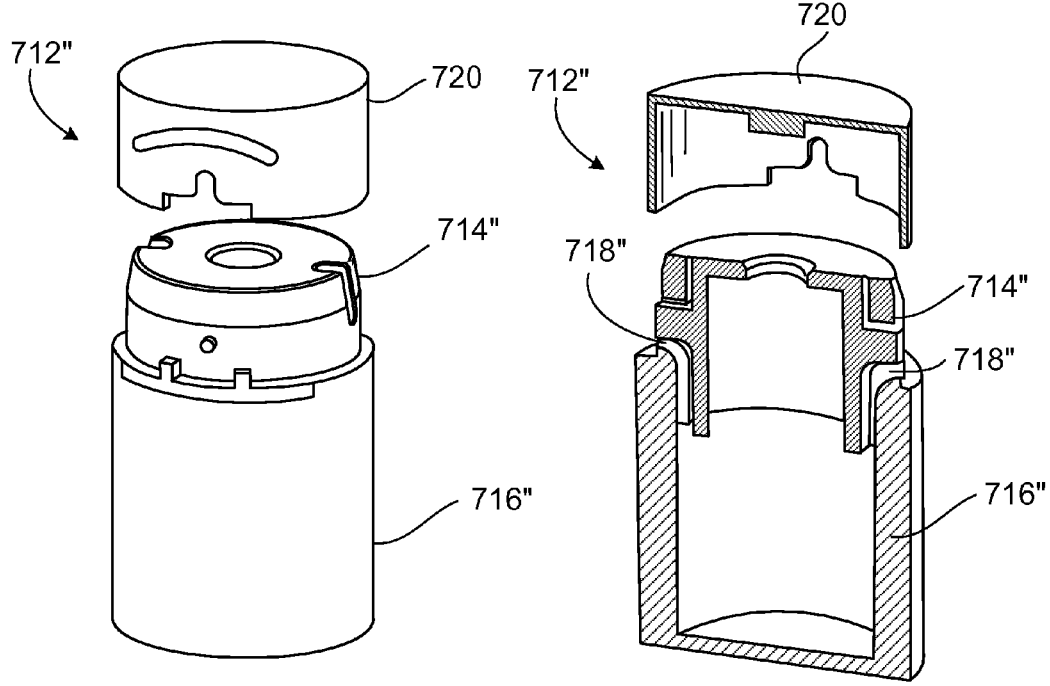
FIGS. 3A-D are views (exploded perspective, exploded cross-sectional, cross-sectional, cross-sectional, respectively) of a consumable-product-containing disposable cartridge with a cover.
Figures 3C, 3D:
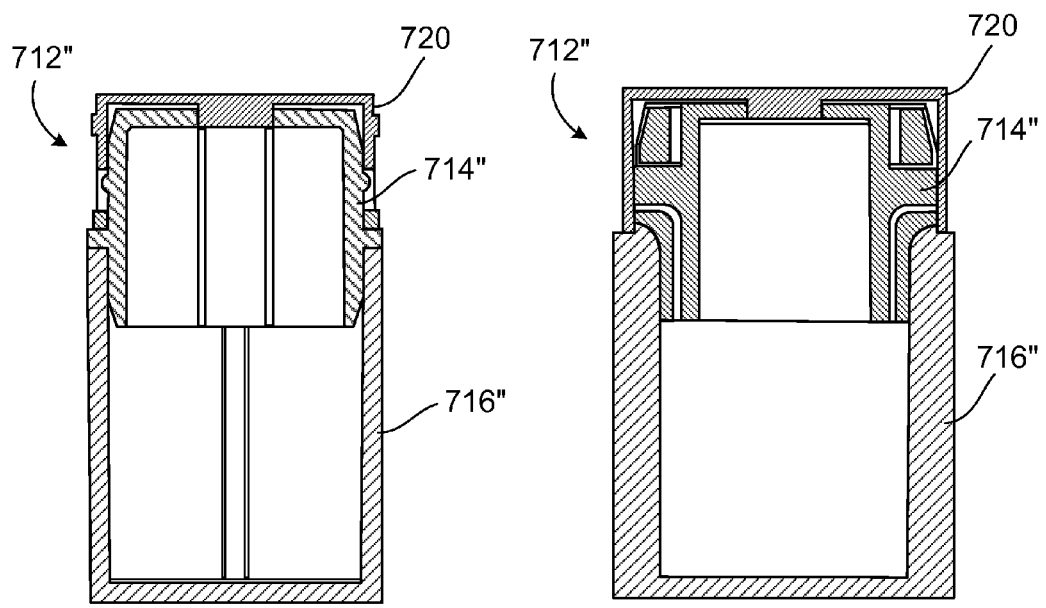
Figure 4:
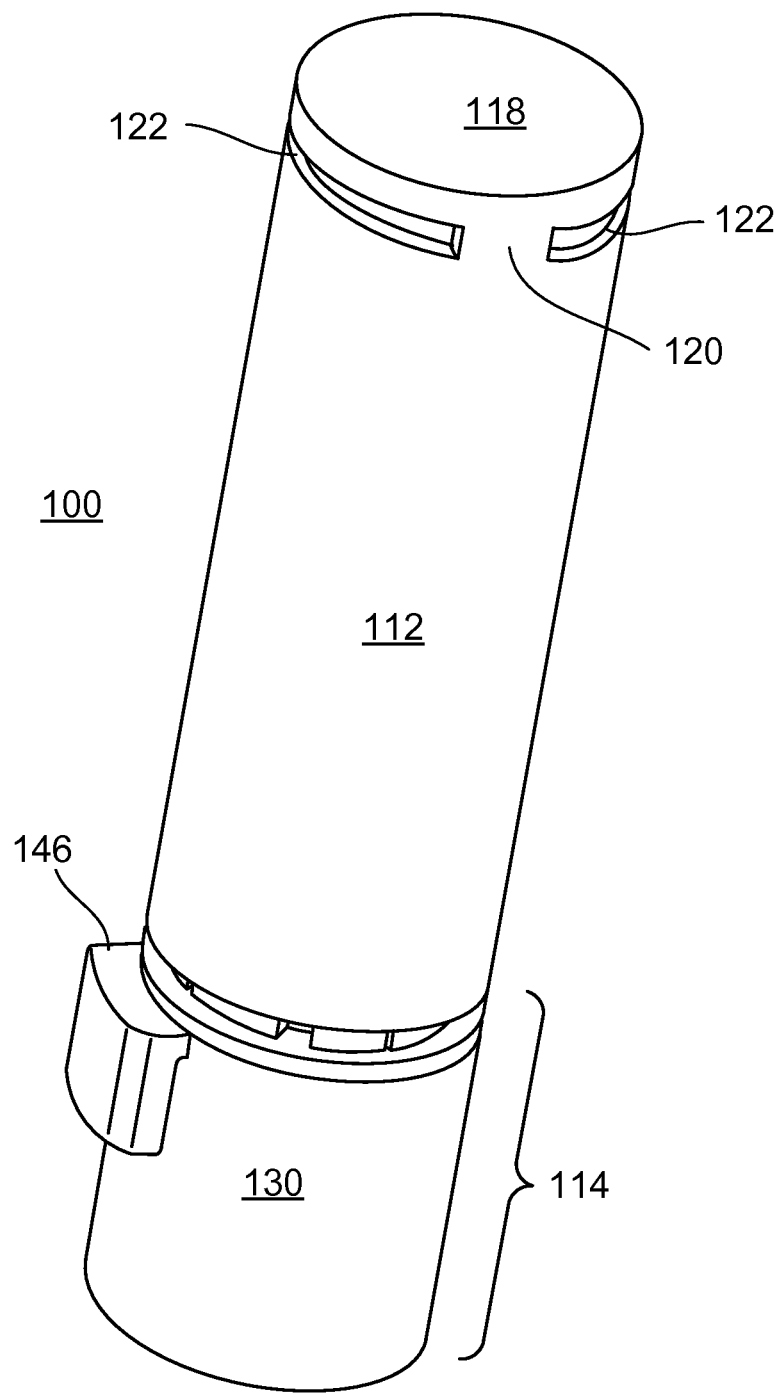
FIG. 4 is a perspective view of a particle delivery device including a cartridge connected to a mouthpiece.
Figure 5:
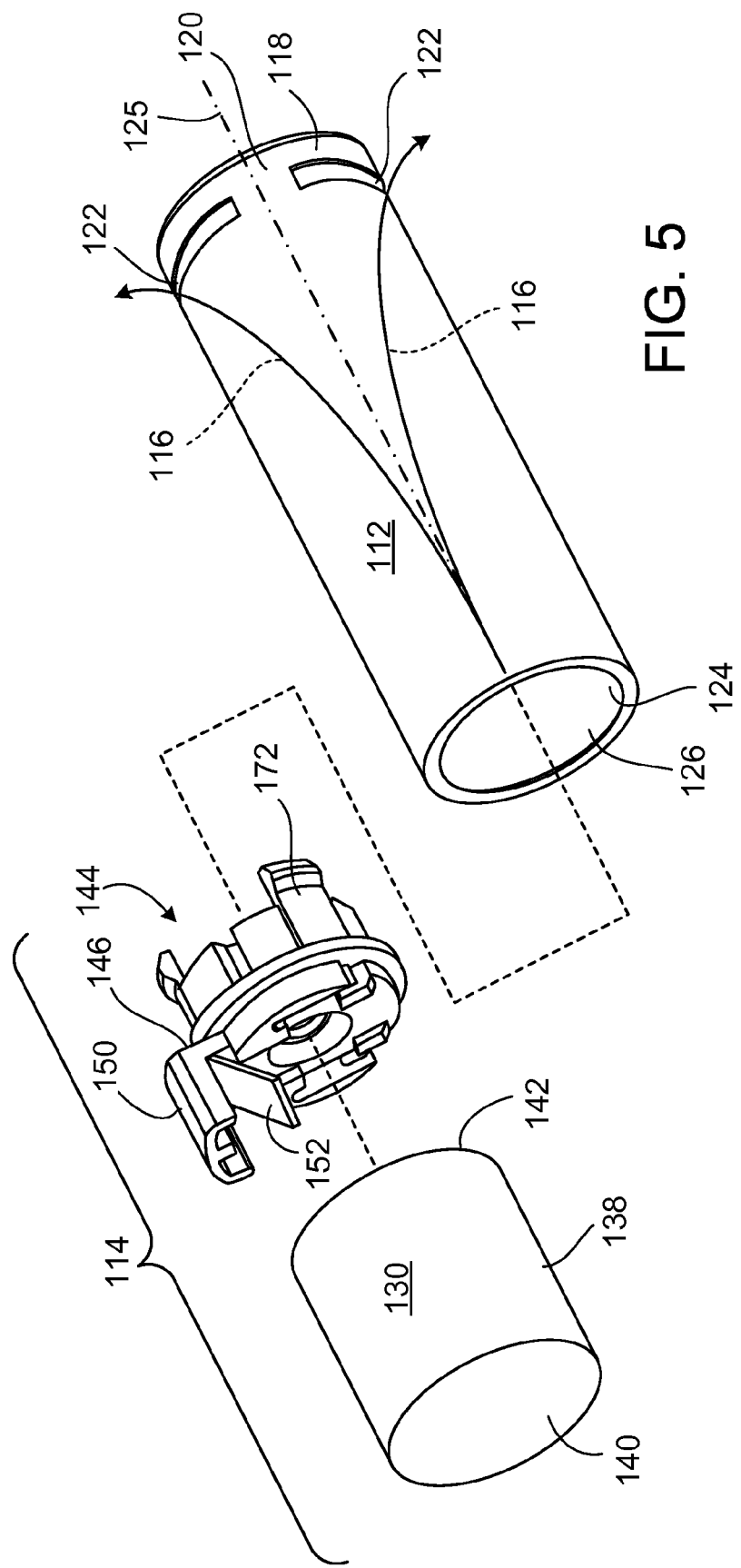
FIG. 5 is an exploded perspective view of the particle delivery device of FIG. 5.

Aerosolized particles small enough to become airborne but too large to be inhaled into the bronchial pathways and lungs retain a sufficient surface area to volume ratio to be solubilized effectively in the mouth. Therefore, a natural breathing process to aerosolize particles can be a particularly effective way to enhance mouth absorption of certain active ingredients. Described herein are various embodiments of an aerosol delivery apparatus designed to use a natural breathing process to aerosolize a consumable product and deliver to the mouth for oral absorption and/or digestive solubilization. Such devices are designed to limit product delivery to the user's throat or lungs, allow for multiple use applications with the same oral delivery device, and provide for enhanced user experience (choice of consumable product to be used with a single device and environmentally low-impact and/or edible devices).

A variety of forces can be used to generate an aerosol from a fluid or dry powder to cause it to move through an aerosol delivery apparatus. These include a user's inhalation/exhalation, aspiration/expiration, shaking or vibration forces, and/or external power sources (e.g., compressed air, electric fans, motors, etc.). Particle size is important to the delivery system. Particles should be small enough to remain airborne during casual breathing, but large enough to be directed and deposited primarily in the mouth while limiting coughing, throat and lung deposition, or other adverse situations. Additionally, it is beneficial that pathways of aerosol particles through the device and out of the mouthpiece are directed away from the back of the throat.

Molecules of consumable, aerosolized products generally absorb in the mouth and the digestive tract via a three-step process. The first step is dissolution or release from a dosage form, the second is diffusion or convection from the site of dissolution to the absorptive mucosa, and the third is active or passive transport across the mucosa into the bloodstream. As used herein, mucosa (or mucosae in plural form) includes mucous membranes that are linings of mostly endodermal origin, covered in epithelium, which are involved in absorption and secretion. Mucosae border cavities, openings and lumen that are exposed to the external environment and internal organs, and can be contiguous with skin in a person's mouth. For those molecules that may absorb across a mucosal barrier at a kinetically effective rate (as determined by hydrophobicity, charge, and molecular size—the more hydrophobic, neutral, and small, the better), the actual rate at the anatomical site of absorption into the bloodstream, once the dosage form is placed in the mouth, is controlled to some degree by the first two steps in the above process, and to some degree by the speed of the digestive process itself.

Consumables (e.g., foods, supplements, or drugs) can be deliverable as chewable solids, liquids, pill, gum, soluble media (e.g., strips) and as a fine powder form that gets distributed on the surfaces of the mouth. Common delivered dosage forms begin to dissolve in the mouth and are swallowed. The active ingredient then diffuses through the mucosa. Depending on the amount of molecule contact with the mucosa, this diffusion may take a significant amount of time in which a user may swallow significant dosage portions of an active ingredient before it has the chance to absorb through the mouth. In cases where the diffusion distance to the tongue is small, and the likelihood of swallowing is small (e.g., with dissolvable strips), mouth-versus-gut absorption is still influenced by the time of dissolution. Increased times for dissolution in your mouth can correlate with more occasions to swallow during the dissolution, and the increased likelihood that dissolved ingredients are swept into the gut and subjected to digestive processes.

Our approach is based, at least in part, on the realization of a new form of aerosolizable product, apparatus for the delivery of aerosolizable products, and methods and uses thereof. More specifically, the delivery technology and approach is directed to aerosolized particles (i.e., food products) and a particle delivery method and apparatus designed to generate and deliver such products to a subject. Such devices can deliver food substances or other particles into the mouth by aerosol wherein the aerosol cloud is generated through a natural inspiration or expiration maneuver and wherein the design of the mouthpiece of the device is such that the airborne particles (e.g., food particles) are diverted away from the back of the throat to limit entry into the respiratory system. Although described with respect to delivery of food products, the devices and methods discussed herein can be used for generation and delivery of other products (e.g., medicinal products, flavorings, nutritional supplements, etc.).

In some embodiments, the combination of appropriate particle size and device-directed aerosol flow path allows for consumable particles (e.g., food particles) being deposited primarily in the mouth (and onto the tongue, palate, etc.) rather than at the back of the throat or into the respiratory tract. In some embodiments, aerosol flow paths are directed to the sides of a user's mouth and not into the lungs, substantially eliminating deposition in regions of the respiratory tract on or near the throat and bronchial airways.

Various embodiments are contemplated and consider certain parameters for effective device function. Physical design differences of the device affect fluid flow properties, such as typical fluid resistances or pressure drops across sections of the apparatus (e.g., a pressure drop over the consumable product, which gives rise to its aerosolization). For particulate or liquid consumables, rates of acceleration, particle velocities, or time of flight durations in sections of the apparatus or upon emission, (e.g., the time for an aerosol to displace from an inlet to an outlet or the velocity it has upon emission) are considered. Also contemplated are aerosol properties, including size, shape, orientation, particle concentration, particle-size distribution, homogeneity, individual particle velocities, and overall (e.g., center-of-mass) aerosol velocities (e.g., the number of consumable-aerosol particles of a given size range, per unit volume of air, upon emission of the aerosol toward a consumer), and/or typical aerosol emission parameters, including the overall flow speed(s) and direction(s) of emitted aerosol and the locations and rates of deposition, relative to the apparatus or consumer (e.g., specific mouth surfaces toward which the aerosol is emitted, on which the aerosol particles are most likely to deposit first).

For any generalized aerosol generation/delivery apparatus, various design parameters and fluid flow properties determine the proportions of the consumable, aerosolizable product emitted from the apparatus. For example, aerosol flow paths that are longer (e.g., between an inlet and an outlet), thinner (e.g., have a smaller cross-sectional area), more tortuous (e.g., have a more sinuous path); and/or more encumbered (e.g., more/larger elements like internal partitions, in closer proximity to the flow path) generally increase the time it takes for an aerosolizable product to reach a user, and generally increase the likelihood that particles (or a proportion of particles) settle before being emitted from the apparatus. This may reduce the proportion of initial product that is ultimately delivered in aerosol form with the desired properties (or decreases the probability that the initial product is ultimately delivered in aerosol form with the desired properties).

A particle delivery apparatus is described that includes features, devices, or elements for containing or receiving aerosolizable particles, and a fluid flow passage extending between an inlet and an outlet. In some embodiments, the apparatus is intended to deliver a consumable aerosolizable product to surfaces within a consumer's mouth. The design of the apparatus, including the shapes, sizes, and orientations of its various components, may have significant impact on a usable consumable product, including the degree of aerosolization, product flow through sections of the apparatus, and emission characterization from the apparatus. In different embodiments, fluid flow passages of the apparatus can be designed with different physical parameters, for example, different air paths, aerosol flow paths, and flow path lengths, different tortuosities (e.g., flow path complexities), different geometries (e.g., inlet or outlet cross-sectional areas and lengths), air flow bypass ports to optimize performance and flow characteristics of the device, and/or different orientations and positions of aerosol flow, bypass port and air inlets and outlets relative to each other and/or the user. The apparatus design parameters thus determine, at least in part, the effectiveness of the system overall in delivering a desired substance to a consumer.

The design of the apparatus can be limited by the rate of aersolization upon actuation and time to transfer to the user's mouth. If, for example, the apparatus design requires an aerosolization time and/or aerosol transfer time outside of a predetermined threshold adequate for the device, the qualities of the aerosolized product may be suboptimal. As particle size and quality are relatively limited by natural physical characteristics of aerosolizable powders and liquids generally, design constraints are more likely to be imposed on the parameters of the apparatus. Nevertheless, for certain relationships among the design parameters and the associated impact on apparatus function, changes may be made to other design parameters to improve function. In general, embodiments described herein appropriately balance the design constraints in such a way as to allow for practical emission of an aerosol product for consumption.

An aerosol delivery apparatus can include a "reusable" mouthpiece and "disposable" cartridges. FIG. 1A illustrates an aerosol delivery apparatus 700 comprising a mouthpiece 112 that can be releasably coupled to a cartridge 712.

The mouthpiece 112 is a rigid, hollow, cylindrical member (FIGS. 1A, 1B, 4 and 5). The mouthpiece 112 defines a fluid flow passage 116 extending from an inlet 124 to the outlet 122 of the mouthpiece 112. In some embodiments, the mouthpiece 112 can have a non-circular cross-section. For example, some mouthpieces have, for example, square, rectangular, or oval cross-sections.

An airflow directing or deflection member 118 is supported at an end of the mouthpiece 112 (e.g., an outlet end of the mouthpiece 112) using bridges 120. The bridges 120 position the airflow directing member 118 in a location spaced apart from a plane of an outlet 122 of the mouthpiece 112.

In some embodiments, the airflow directing member 118 is a deflection member that may take any of a variety of forms (not necessarily that of a disc), in order to divert the airflow exiting the mouthpiece 112 and entering the mouth, away from a straight trajectory toward the throat and lungs. For example, there may be one or more openings near the top of a mouthpiece 112, which may be offset relative to each other, at different heights, of different sizes, of different areas, etc., which maintain the general blockage of the direct linear path toward the back of the mouth, and generally divert the airflow and aerosol such that it goes in more lateral directions.

In some embodiments, airflow directing member 118 is a thin disc with a flat surface that is generally perpendicular to the longitudinal axis 125 of the mouthpiece 112 and in opposition to the general airflow direction (e.g., along the longitudinal axis 125) in the mouthpiece 112. In some implementations, the airflow directing member 118 changes the airflow direction of air exiting the mouthpiece 112 to a direction that is angled relative to the longitudinal axis 125. For example, in some implementations, the airflow directing member 118 redirects air exiting the mouthpiece to a direction that is substantially transverse to the longitudinal axis 125 (e.g., directing the flow toward the sides of the mouth). In some cases, the disc may be mounted to the mouthpiece via one or more "bridges" 120, which may, for example, hold the disc slightly above, below, or at the same level as the edge of the mouthpiece, allowing air, and the aerosolized product to pass around the disc. In various embodiments, the disc may have a diameter smaller, equal to, or larger than the opening of the mouthpiece. Additionally, the disc may be of any desired shape, for example, an elliptical shape or round shape. The airflow directing member 118 redirects the aerosol to the sides of the mouth (e.g. top, bottom, left, and right surfaces within the mouth), thereby limiting flow of the aerosol toward the throat where it might elicit a coughing reflex. Instead, the aerosolized product deposits on the tongue or other parts of the mouth where it can be sensed and appreciated rather than carried deeper into the respiratory tract. In some embodiments, airflow directing member 118 is of a different shape, size, and/or design but similarly serves to redirect the aerosolized product so as to limit the coughing reflex and/or to enhance the taste experience. Testing of a variety of disc sizes and positions has shown that these two parameters can impact likelihood of coughing. For example, it was found in preliminary tests that a disc whose diameter is roughly equal to that of the external diameter of the mouthpiece, and that is placed close to the mouthpiece, is generally more effective in redirecting the aerosol and limiting coughing, than one whose diameter is roughly equal to that of the internal diameter of the mouthpiece (thus smaller) and that is placed at a greater distance from the mouthpiece (leaving a larger space for the aerosol to pass through).

In this embodiment, the mouthpiece 112 is made of a durable material, such as stainless steel, and is intended for multiple deliveries of consumable product (e.g., about 50 or more). The mouthpiece 112, in this example, is also intended to be cleaned by hand or by dishwasher, to facilitate longer-term use with minimal hygienic risk.

The cartridge 712 receives and stores a consumable, aerosolizable product. When connected to the mouthpiece 112, the cartridge 712 supports the aerosolizable product in a desired position relative to the mouthpiece 112. The cartridge 712 cannot be readily opened to access the consumable product inside. This is advantageous for instances in which it is preferable that the user have limited direct access to the consumable product (i.e., access other than by delivery via the mouthpiece as intended). This may be the case when the consumable product is a controlled substance, a sensitive substance, or a substance that requires a very precise dose. This may also reduce the risk of a user inserting other materials into the device.

In this embodiment, cartridge 712 includes upper element 714 and lower element 716. While a consumer is not able to readily separate elements 714 and 716, the two elements were initially separate so as to permit filling of cartridge 712 during the manufacture of the overall product. In this embodiment, element 716 is filled with the consumable product during the manufacture of the overall product, and shortly thereafter, element 714 is affixed to element 716, for example by a snap fit. The snap fit can be designed to resist being taken apart once the two elements are affixed. In some embodiments, other methods of attachment such as, for example, press fits and ultrasonic welding can be used to attach element 714 is affixed to element 716.

The overall product can be used by coupling a mouthpiece 112 to cartridge 712. Multiple deliveries of consumable product are possible in this configuration. When a user draws in air via the mouthpiece outlet 122, air is forced into the cartridge via air inlets 718. Flowing air aerosolizes the consumable product in cartridge 712 and delivers the aerosolized product toward the user via mouthpiece 112.

Mouthpiece 112 can then be detached from cartridge 712, and a new cartridge 712 may be attached to the same mouthpiece 112. In certain embodiments an air bypass port is formed at a junction or interface between cartridge 712 and mouthpiece 112.

FIGS. 2A-2C show an embodiment of a cartridge 712' with upper element 714' and lower element 716'. In this example, features on upper element 714' allow for releasable coupling to a mouthpiece, as well as for airflow to enter the cartridge during use of the apparatus. For example, when the mouthpiece and cartridge are coupled, these features of upper element 714' "latch onto" the mouthpiece 112, holding it securely to the cartridge 712', while small spacers maintain a distance between the bottom edge of the mouthpiece and the cartridge, preserving airflow passages into the cartridge.

In some embodiments, upper elements 714" are configured to engage a cover 720 as shown in FIGS. 3A-3D. The cover 720 can include a central protrusion sized to close the outlet of the upper element 714" and side surfaces configured to cover the air inlets defined between upper element 714" and lower element 716".

Referring to FIGS. 4-10, an example particle delivery device 100 includes the mouthpiece 112 and a detachable cartridge 114 that receives and stores aerosolizable particles. The particle delivery device 100 is sized such that a user can easily hold the device in one hand while using the device 100 to generate and deliver an aerosolized product.

The cartridge 114 is detachably connected to an opposed end (e.g., an inlet end) of the mouthpiece 112 relative to the airflow directing member 118. The cartridge 114 can be detached from the mouthpiece and reattached, or replaced with a different cartridge.

The cartridge 114 includes a hollow, cylindrical housing 130 that defines an internal reservoir 132 that receives and stores the aerosolizable product. The housing 130 includes an annular sidewall 138 having a closed first end 140 and open second end 142 opposed to the first end 140. The housing 130 also includes a cover 144 disposed on the open second end 142. The cover 144 includes a central opening (e.g., cartridge outlet) 134 and at least one peripheral opening (e.g., cartridge inlet) 136 that is disposed between the cartridge outlet 134 and a peripheral edge of the cover 144 and is configured to permit fluid communication between the reservoir 132 and an exterior of the cartridge 114. In the illustrated embodiment, the cover includes two cartridge inlets 136 that are spaced apart from each other.

Figure 10:
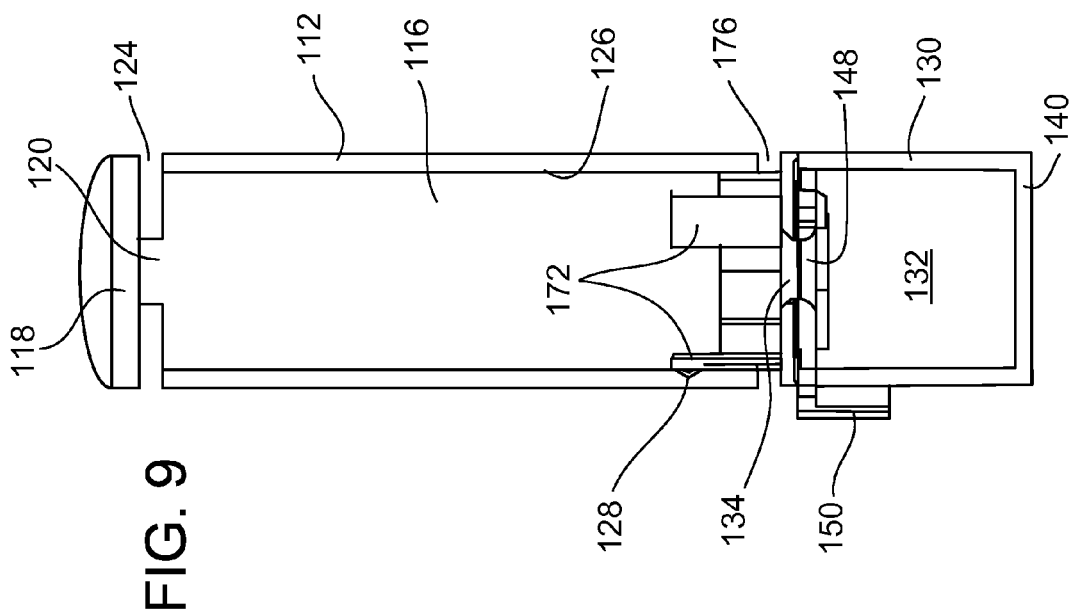
FIG. 10 is a side sectional view of the particle delivery device of FIG. 5 with the cartridge in a closed configuration.

In addition, the cover 144 includes features that permit selective opening and closing of the cartridge outlet 134. In particular, the cover 144 is provided with a tab 146 that is slidably connected to the cover 144 so as to be movable (e.g., slidable along an axis transverse to a longitudinal axis of the device 100) between a first position in which an opening 148 of the tab 146 is aligned with the cartridge outlet 134 (FIG. 9), and a second position in which a portion of the tab 146 overlies and substantially completely obstructs the cartridge outlet 134 (FIG. 10). When the cartridge 114 is assembled with the mouthpiece 112, and the tab 146 is in the first (e.g., open) position, fluid communication is permitted between the reservoir 132 and the mouthpiece fluid flow passage 116 via the cartridge outlet 134. When the cartridge 114 is assembled with the mouthpiece 112, and the tab 146 is in the second (e.g., closed) position, fluid communication is substantially prevented between the reservoir 132 and the mouthpiece fluid flow passage 116 via the cartridge outlet 134. The tab 146 extends outward from the housing 130, and includes a flange (e.g., an actuator) 150 that can be manipulated by a user to control the tab position. A spring 152 protrudes from tab 146 so as to reside between the flange 150 and the housing sidewall 138. The spring 152 serves to bias the tab 146 to the second (e.g., closed) position.

The cover 144 includes a pair of rails 162 are formed on a first side 160 of the cover 144. An inner edge 166 of the rails 162 support the tab 146 as it slides between the first position and the second position. The outer peripheral edges 164 of the rails 162 are curved, and are sized to engage (e.g. form a press fit connection with) an inner diameter of the housing sidewall 138, whereby the cover 144 is connected to the housing 130.

Figure 6:
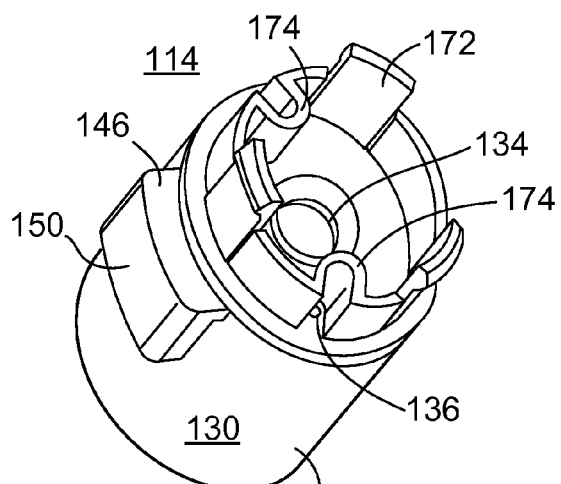
FIG. 6 is a perspective view of the cartridge of FIG. 5.
Figure 7:
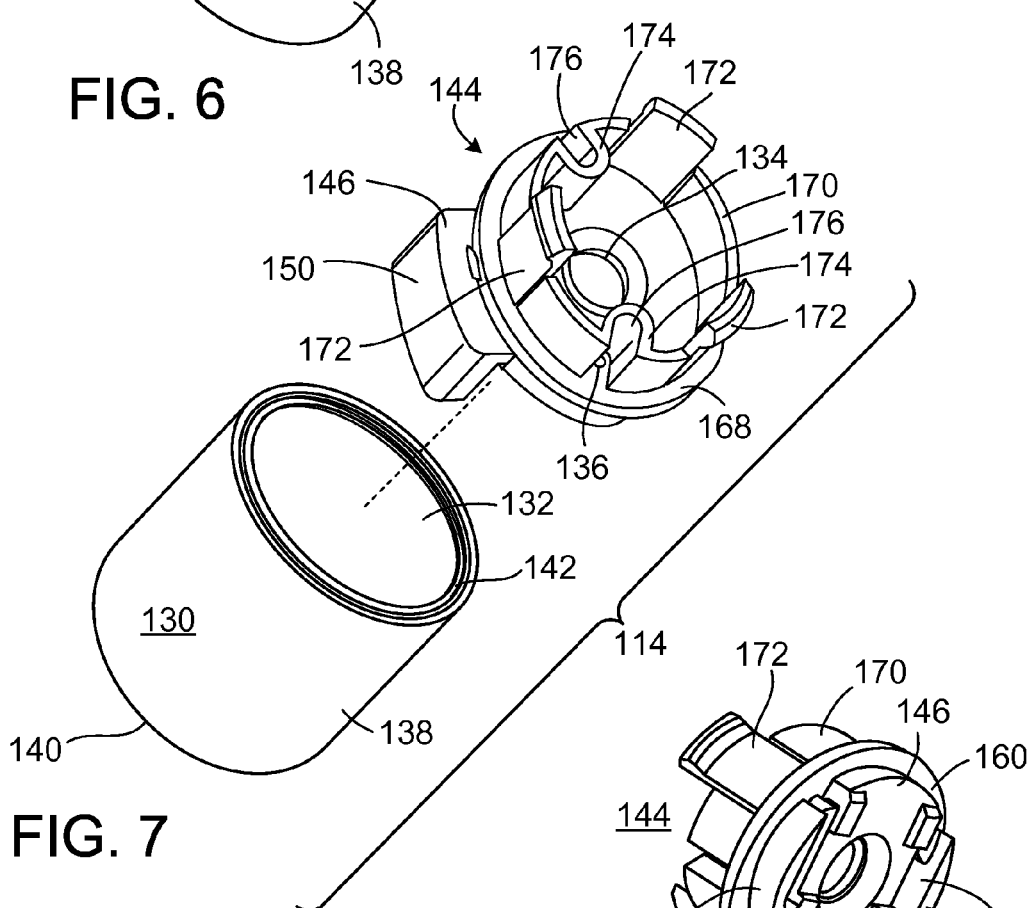
FIG. 7 is an exploded view of the cartridge of FIG. 5 including a housing and a cover.
Figure 8:
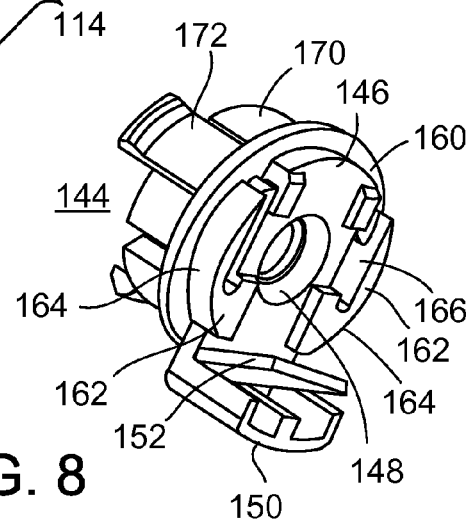
FIG. 8 is a perspective view of the cover of FIG. 7.
Figure 9:
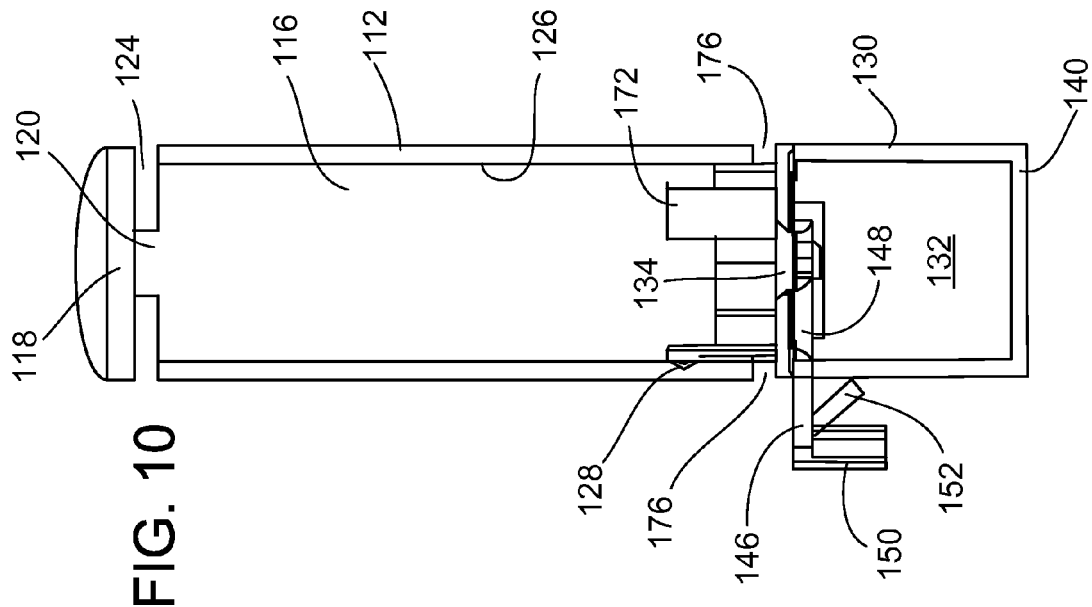
FIG. 9 is a side sectional view of the particle delivery device of FIG. 5 with the cartridge in an open configuration.

In addition, the cover 144 includes a connection portion 170 that protrudes outward from a second side 168 of the cover 144. The connecting portion 170 is dimensioned to be received within an inner diameter of the mouthpiece 112, and includes arms 172 that are configured to form a snap fit engagement with corresponding grooves 128 formed in an inner surface of the mouthpiece 112. In addition, the connection portion 170 includes partitions 174 that form a generally semi-circular wall that partially surround each cartridge inlet 136. As seen in FIG. 6, the partitions 174 are arranged so that the cartridge inlets 136 are located on an outer side of the connection portion 170. In particular, when the mouthpiece 112 is assembled with the cartridge 114, each partition 174 cooperates with an inner surface 126 of the mouthpiece 112 to form an air bypass port 176 that permits air flow into the mouthpiece fluid flow passage 116.

When the cartridge 114 is connected to inlet end of the mouthpiece 112, and the tab 146 is in the first (e.g., open) position, the mouthpiece 112 and the cartridge 114 together define a flow path through the device 100. Thus, when a user places the outlet 122 of the mouthpiece 112 in his or her mouth and inhales, air flows into the reservoir 132 through cartridge inlets 136. Air then flows from the reservoir 132 through the cartridge outlet 136 and into the inlet 124 of the mouthpiece 112. Air is drawn into the mouthpiece 112 through both the mouthpiece inlet 124, and also through the air bypass port 176. The air flows along the fluid flow passage 116, and exits the mouthpiece 112 via the mouthpiece outlet 122. Contact with the airflow directing member 118 deflects the air flowing out of the mouthpiece 112. In the illustrated embodiment, the airflow directing member 118 deflects the air flowing out of the mouthpiece 112 to a direction substantially perpendicular to a longitudinal axis 125 of the mouthpiece 112.

A user operates a particle delivery device 100 by loading the device 100 (e.g., placing areosolizable particles in the reservoir 132 and/or connecting the cartridge 114 to the mouthpiece 112), bringing the device 100 to the user's mouth, and inhaling through the mouthpiece 112 thereby causing air to enter the cartridge 114 and mouthpiece 112 through the air passageways. The air aerosolizes the powder present in the reservoir 132, and the aerosol subsequently enters the user's mouth via the mouthpiece 112.

In some embodiments, a user places his/her tongue near an outlet (or inhaler orifice), for example outlet 122, in order to alter the speed and/or direction of the aerosol emitted from the apparatus. In some cases, the user may position the outlet such that the aerosol is emitted toward the sublingual area. In some cases, the user may position the outlet such that the aerosol is emitted toward to lower side of the tongue, with the tongue in an elevated position (i.e. with the tip of the tongue generally closer to the top of the mouth than a region of the tongue closer to the throat). In some cases, an inspiratory or sipping maneuver under such conditions will cause aerosol particles to enter the mouth and divert to a desired surface or material within the mouth (e.g., the sides of the mouth, the top of the tongue, saliva, taste buds). In some cases, such conditions will limit undesirable side effects, such as coughing.

In some embodiments, a user places his/her teeth near an outlet (or inhaler orifice), for example outlet 122, in order to alter the speed and/or direction of the aerosol emitted from the apparatus. In some cases, under such conditions, aerosol particles with hygienic, "freshening", or other qualities are thus diverted toward surfaces where these particles can be most beneficial (e.g., gum surfaces).

In some embodiments, other physiological members are used to favorably alter the speed and/or direction of the aerosol emitted from the apparatus.

In some embodiments, an aerosol is generated by an expiratory breathing maneuver, in which air emitted by a user either directly or indirectly causes a consumable product to aerosolize.

In some embodiments, the aerosol is generated at a particular point in time or over a small interval of time corresponding to a specific activation step, and/or the aerosol is generated by a user-dependent step. For example, in some cases aerosol generation is associated with one or more inhalation maneuvers by the user. In many of these embodiments, the product is in a solid state, and may be a substantially dry powder.

Figure 11:
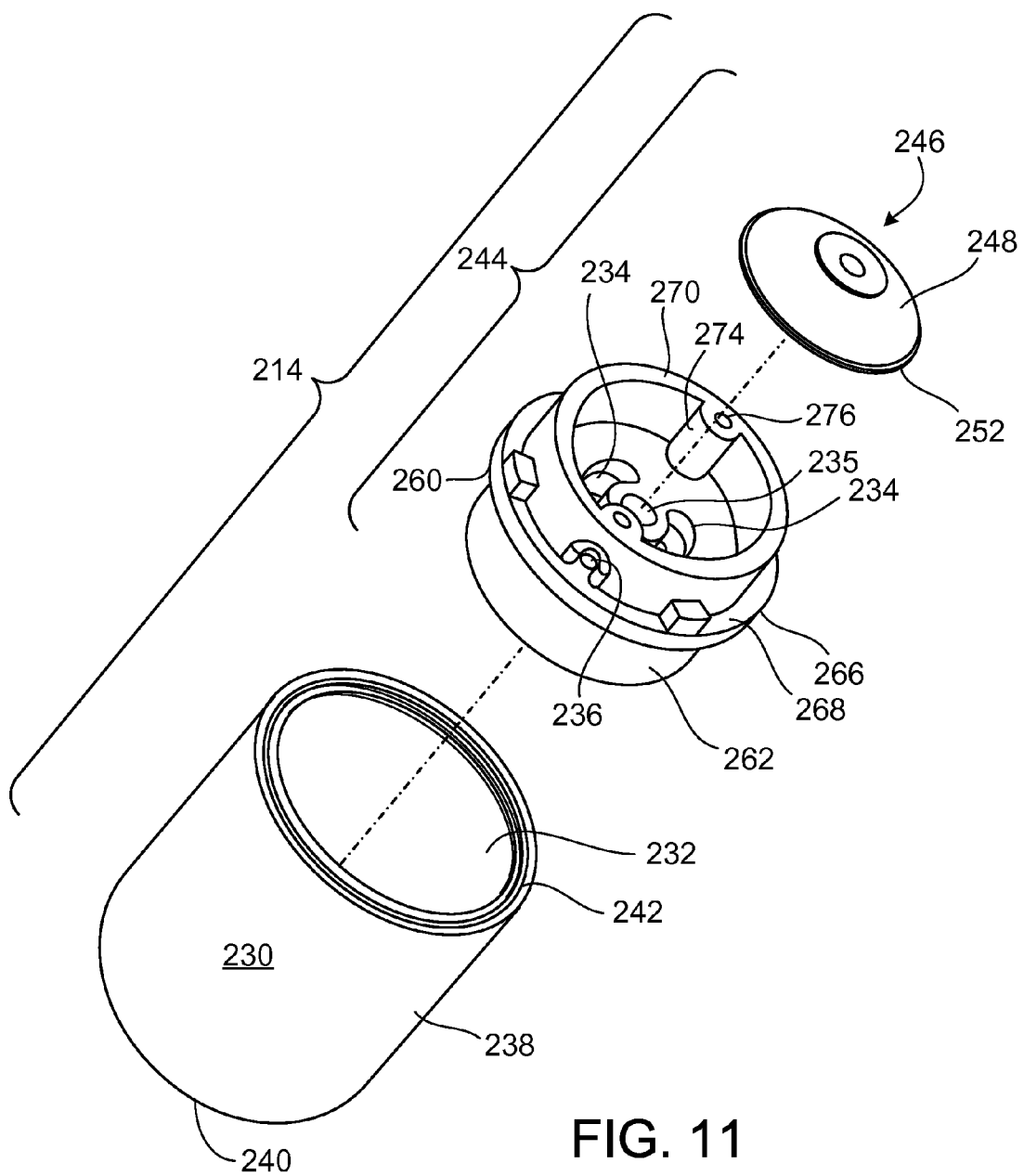
FIG. 11 is an exploded perspective view of an alternative embodiment cartridge, including a housing, a cover, and an umbrella valve.
Figure 12:
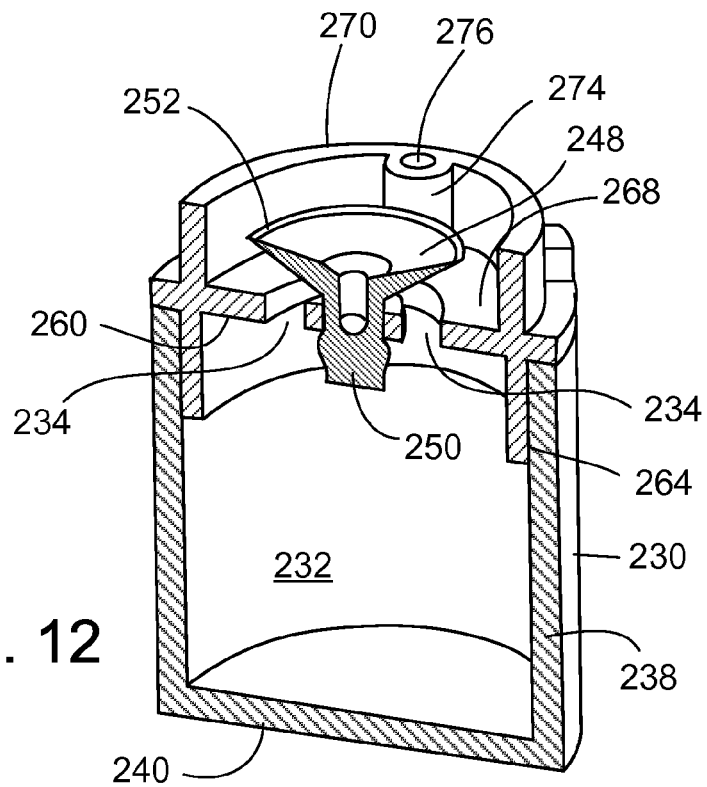
FIG. 12 is a perspective cross sectional view of the cartridge of FIG. 11 illustrating the umbrella valve in an open position.
Figure 13:
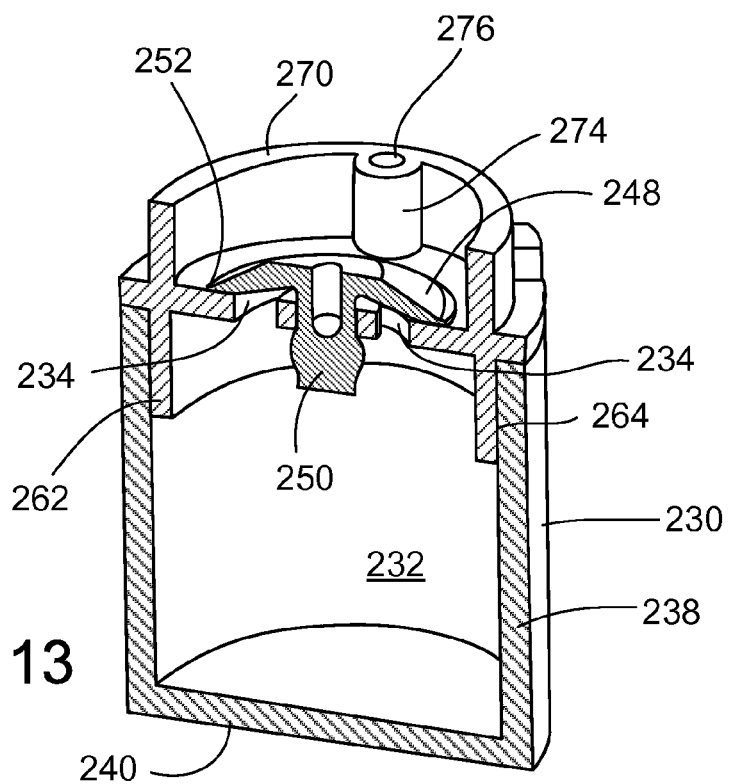
FIG. 13 is a perspective cross sectional view of the cartridge of FIG. 11 illustrating the umbrella valve in a closed position.
Figure 14:
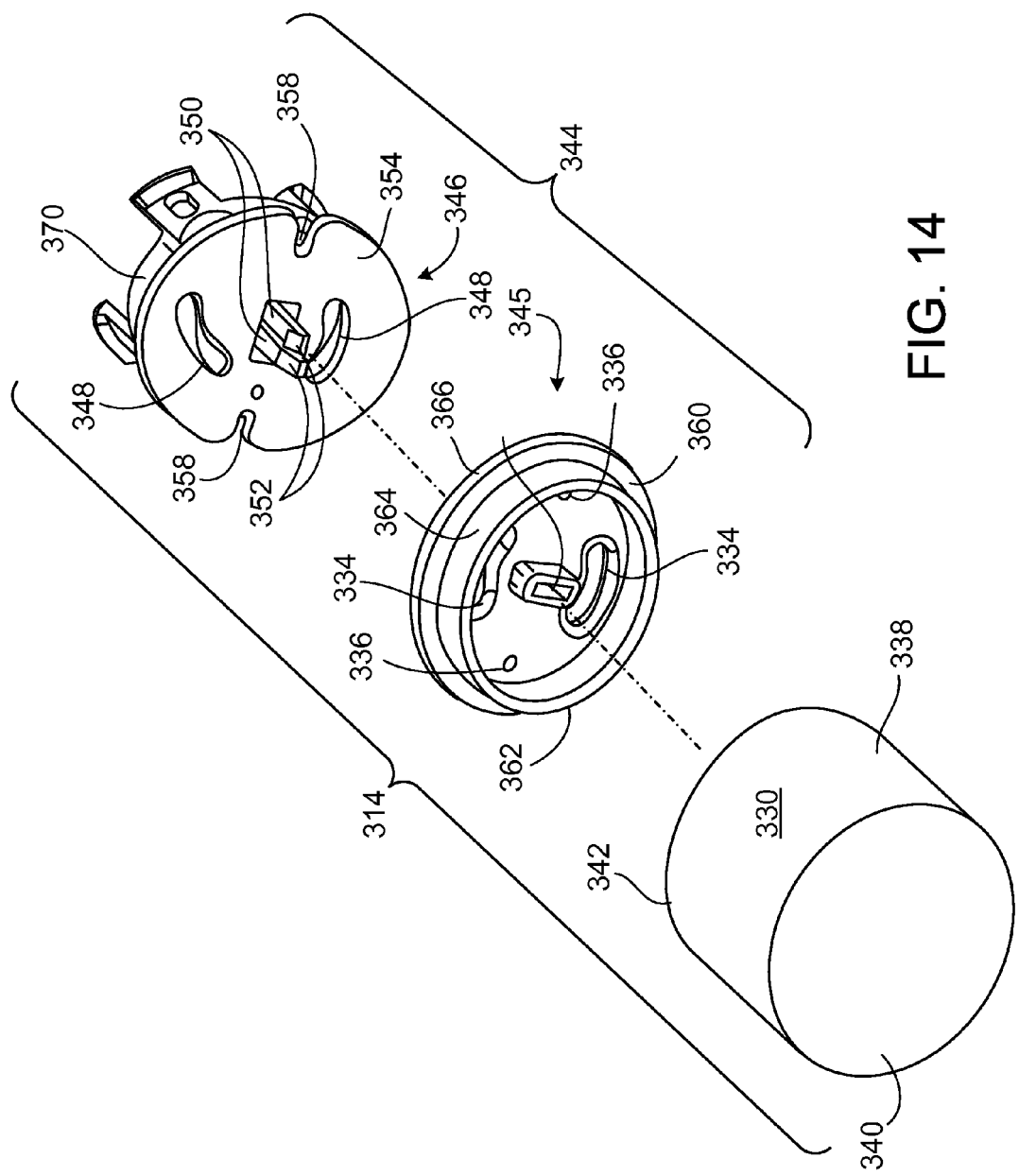
FIG. 14 is an exploded perspective bottom-end view of another alternative embodiment cartridge, including a housing, a cover, and a plate valve.
Figure 15:
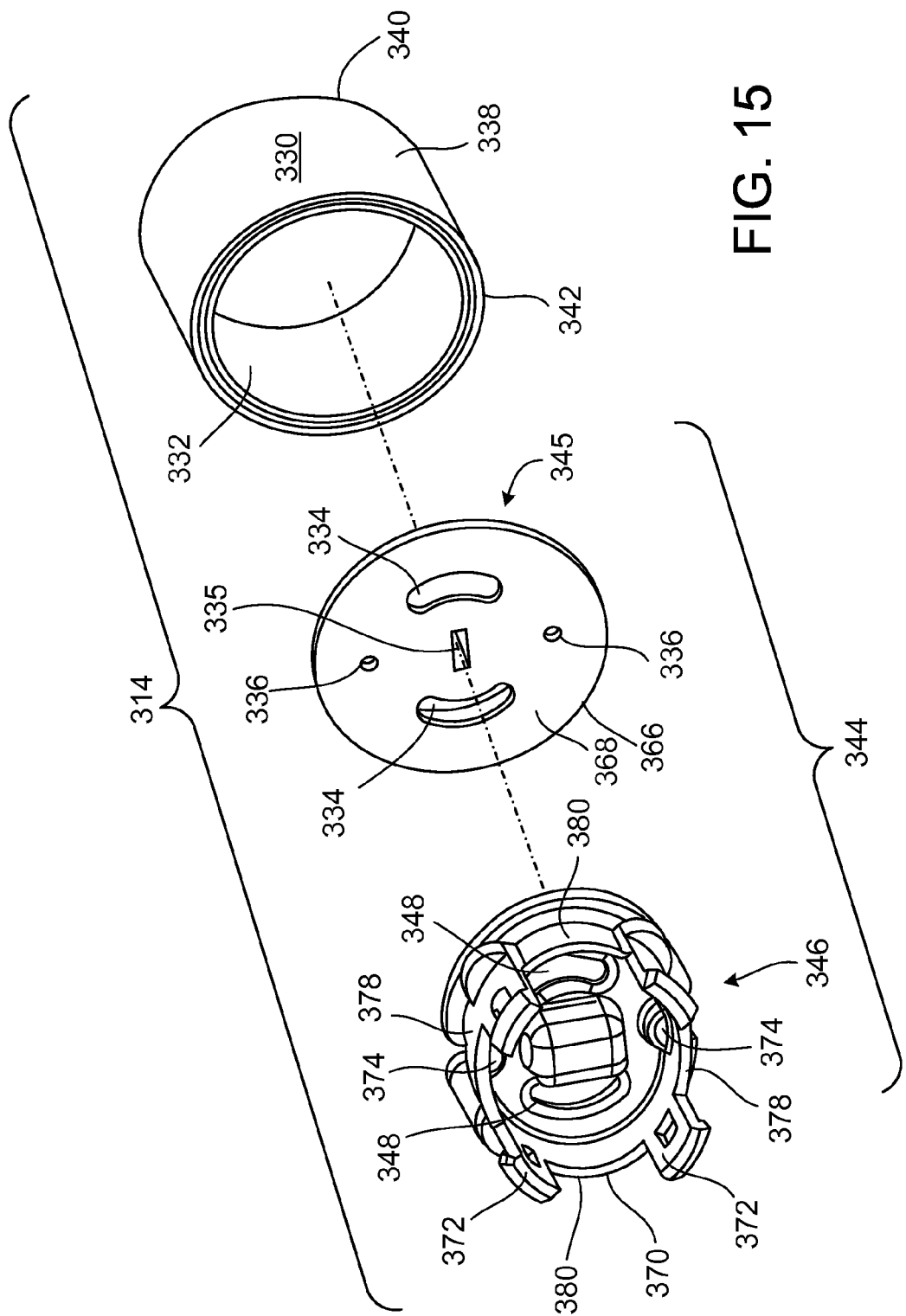
FIG. 15 an exploded perspective top-end view of the cartridge of FIG. 14.

Referring to FIGS. 11-13, another embodiment cartridge 214 can be used with the mouthpiece 112 and includes a sealing or closing device operable on the cartridge to permit selective opening and closing of the cartridge inlets and outlets. In this embodiment, the cartridge 214 is configured such that inspiration or expiration by the user activates the device 100 for open airflow and payload aerosolization without the need for manual or digital actuation of the sealing or closing mechanism.

The cartridge 214 includes a hollow, cylindrical housing 230 that defines an internal reservoir 232 that receives and stores the aerosolizable product. The housing 230 includes an annular sidewall 238 having a closed first end 240 and open second end 242 opposed to the first end 240. The housing 230 also includes a cover 244 disposed on the open second end 242. The cover 244 includes a central opening 235 that is sized to receive and support a stem 250 of an umbrella valve 246, as discussed further below. The cover includes a pair of openings (e.g., cartridge outlets) 234 that are disposed between the central opening 235 and a peripheral edge 266 of the cover 244. The cartridge outlets 234 are elongated and extend around the central opening 235 in a bean-shaped configuration that maximizes outlet size. In addition, the cover 244 includes at least one peripheral opening (e.g., cartridge inlet) 236 that is disposed between the cartridge outlets 234 and the cover peripheral edge 266 and configured to permit fluid communication between the reservoir 232 and an exterior of the cartridge 114. In the illustrated embodiment, the cover 244 includes two cartridge inlets 236 (only one is shown, in FIG. 11) that are spaced apart from each other.

In addition, the cover 244 includes features that permit selective opening and closing of the cartridge outlets 234. In particular, the cover 244 is provided with an umbrella valve 246. The umbrella valve 246 includes a flexible, hollow, conical valve body 248 and a stem 250 that protrudes from an inside apex of the valve body 248. The stem 250 is fixed within in the cover central opening 235, and supports the valve body 248 in a position that overlies a second side 268 of the cover 244. The valve body 248 is dimensioned so that the valve body 248 overlies the cartridge outlets 234. When the valve 246 is in a closed position (FIG. 13), the peripheral edge 252 of the valve body 248 contacts the second side 268 of the cover 244 in the region between the cartridge outlets 234 and the cartridge inlets 236. As a result, the valve body 248 substantially completely obstructs the cartridge outlet 234 when in a closed position. When the valve is in an open position (FIG. 12), the valve body 248 is inverted relative to the stem 250 so that the peripheral edge 252 of the valve body 248 resides above (e.g., spaced apart from) the cover second side 268, and air can flow through the cartridge outlet 236. The valve 246 is movable between the first (e.g., open) position and the second (e.g., closed) position by forming a differential pressure on one side of the valve. In this embodiment, when the cartridge 214 is connected to the mouthpiece 112 and a user inhales with the mouthpiece outlet 122 in the user's mouth, a region of low pressure is formed in the mouthpiece 112 that causes the valve body to invert as shown in FIG. 12. Upon release of the low pressure (e.g., when the user stops inhaling), the valve body 248 resiliently returns to its original, non-inverted configuration as shown in FIG. 13.

When the cartridge 214 is assembled with the mouthpiece 112, and the valve 246 is in the first (e.g., open) position, fluid communication is permitted between the reservoir 232 and the mouthpiece fluid flow passage 116 via the cartridge outlet 234. When the cartridge 214 is assembled with the mouthpiece 112, and the valve 246 is in the second (e.g., closed) position, fluid communication is limited (e.g., substantially or entirely prevented) between the reservoir 232 and the mouthpiece fluid flow passage 116 via the cartridge outlet 234.

The cover 244 includes an annular protrusion 262 that is formed on a first side 260 of the cover 244. An outer peripheral edge 264 of the annular protrusion 262 is sized to engage (e.g. form a press fit connection with) an inner diameter of the housing sidewall 138, whereby the cover 244 is connected to the housing 230.

In addition, the cover 244 includes a connection portion 270 that protrudes outward from the second side 268 of the cover 244. The connecting portion 270 is dimensioned to be received within an inner diameter of the mouthpiece 112 and to engage (e.g. form a press fit connection with) the inner surface of the mouthpiece 112. In addition, the connection portion 270 includes partitions 274 that form a generally circular wall that surrounds each cartridge inlet 236. Each partition 274 has an open upper end and thus forms an air bypass port 276 that permits air flow into the mouthpiece fluid flow passage 116. Alternatively, an air bypass port can be developed at the junction formed between an outer diameter surface feature of the connection portion 270 and an inner diameter surface of the mouthpiece 112 when assembled, with or without air bypass port 276.

When the cartridge 214 is connected to inlet end of the mouthpiece 112, and the valve 246 is in the first (e.g., open) position, the mouthpiece 112 and the cartridge 214 together define a flow path through the device 100. Thus, when a user places the outlet 122 of the mouthpiece 112 in his or her mouth and inhales, air flows into the reservoir 232 through cartridge inlets 236. Air then flows from the reservoir 232 through the cartridge outlet 236 and into the inlet 124 of the mouthpiece 112. Air is drawn into the mouthpiece 112 through both the mouthpiece inlet 124 and the air bypass port 276. The air flows along the fluid flow passage 116, and exits the mouthpiece 112 via the mouthpiece outlet 122. Contact with the airflow directing member 118 deflects the air flowing out of the mouthpiece 112. In the illustrated embodiment, the airflow directing member 118 deflects the air flowing out of the mouthpiece 112 to a direction substantially perpendicular to a longitudinal axis 125 of the mouthpiece 112.

In some embodiments, the umbrella valve 246 may be replaced with a different type of valve. For example, in some embodiments, the cartridge 214 includes a one-way (clack, check, non-return, etc.) valve including, but not limited to, a duckbill valve, a ball-check valve, a diaphragm check valve, a swing check valve, a stop-check valve, lift-check valve, an in-line check valve, etc.

Referring to FIGS. 14-18, another cartridge 314 can be used with the mouthpiece 112 and includes a sealing or closing device operable on the cartridge to permit selective opening and closing of the cartridge inlets and outlets. In this embodiment, the cartridge 314 includes a manually actuated "twist-to-open" port covering mechanism.

The cartridge 314 includes a hollow, cylindrical housing 330 that defines an internal reservoir 332 that receives and stores the aerosolizable product. The housing 330 includes an annular sidewall 338 having a closed first end 340 and open second end 342 opposed to the first end 340. The housing 330 also includes a cover assembly 344 disposed on the open second end 342. The cover assembly 344 includes a cover plate 345 having a central opening 335 that is sized to receive and support resilient legs 350 of a valve plate 346, as discussed further below. The cover plate 345 includes a pair of openings (e.g., cartridge outlets) 334 that are disposed between the central opening 335 and a peripheral edge 366 of the cover plate 345. The cartridge outlets 334 are elongated and extend around the central opening 335 in a bean-shaped configuration that maximizes outlet size. In addition, the cover plate 345 includes two peripheral openings (e.g., cartridge inlets) 336 disposed between the central opening 335 and a peripheral edge 366 of the cover plate 345, and configured to permit fluid communication between the reservoir 332 and an exterior of the cartridge 314.

In addition, the cover assembly 344 includes features that permit selective opening and closing of the cartridge outlets 334. In particular, the cover assembly 344 is provided with a plate valve 346. The plate valve 346 has a pair of elongated openings 348 that are shaped, dimensioned and positioned to match the cartridge outlets 334. In addition, a peripheral edge of the plate valve 346 is formed having cut outs 358 arranged to overlie the cartridge inlets 336 when the openings 348 are aligned with the cartridge outlets 334. A pair of resilient legs 350 protrude outward from a first side (e.g., cover-facing side) 354 of the valve plate 346. The legs 350 are arranged side-by-side and have a length sufficient to protrude through the central opening 335 of the cover plate 345. The legs 350 include a hooked tip 352 that prevents axial separation of the valve plate 346 from the cover plate 345 once assembled. The legs 350 are flexible and resilient, whereby the plate valve 346 is permitted to rotate relative the cover plate 345 about a longitudinal axis of the device 100.

Figure 16:
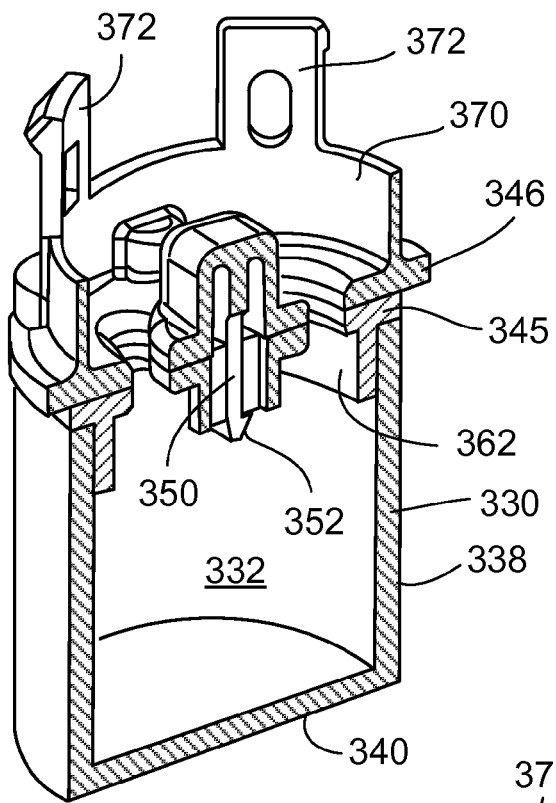
FIG. 16 is a perspective cross sectional view of the cartridge of FIG. 14 illustrating the plate valve in an open position.
Figure 17:
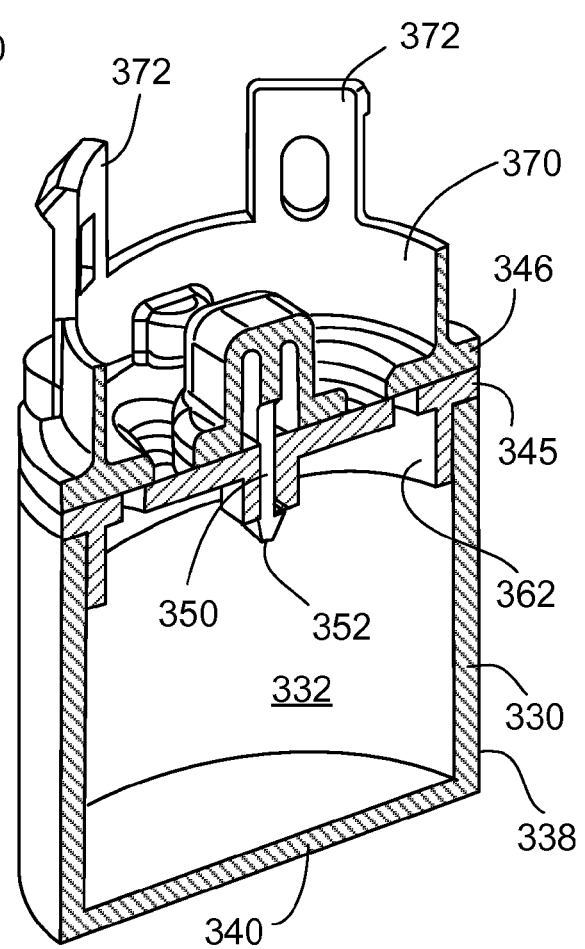
FIG. 17 is a perspective cross sectional view of the cartridge of FIG. 14 illustrating the plate valve in a closed position.

The plate valve 346 is rotatably connected to the cover plate 345 so as to be movable (e.g. rotatable about a longitudinal axis of the device 100) between a first position in which the plate valve openings 348 are aligned with corresponding cartridge outlets 334 and the plate valve cut outs 358 are aligned with the cartridge inlets 336 (FIG. 16), and a second position in which a first portion of the plate valve 346 overlies and substantially completely obstructs the cartridge outlets 334 and a second portion of the plate valve 346 overlies and substantially completely obstructs the cartridge inlets 336 (FIG. 17). When the cover assembly 344 is connected to the mouthpiece 112, and the plate valve 346 is in the first (e.g., open) position, fluid communication is permitted between the reservoir 332 and the mouthpiece fluid flow passage 116 via the cartridge outlet 334. In the first position, due to the rotation of the valve plate 346 relative to the cover 344, the legs 350 of the plate valve are slightly stretched and twisted about each other. Due to their resiliency, the legs 350 apply a biasing force that urges the plate valve 346 toward the second position. When the cartridge 114 is assembled with the mouthpiece 112, and the plate valve 346 is in the second (e.g., closed) position, fluid communication is limited (e.g., substantially or entirely prevented) between the reservoir 332 and the mouthpiece fluid flow passage 116 via the cartridge outlet 334.

The cover plate 345 includes an annular protrusion 362 that is formed on a first side 360 of the cover 344. An outer peripheral edge 364 of the annular protrusion 362 is sized to engage (e.g. form a press fit connection with) an inner diameter of the housing sidewall 338, whereby the cover 344 is connected to the housing 330.

Figure 18:
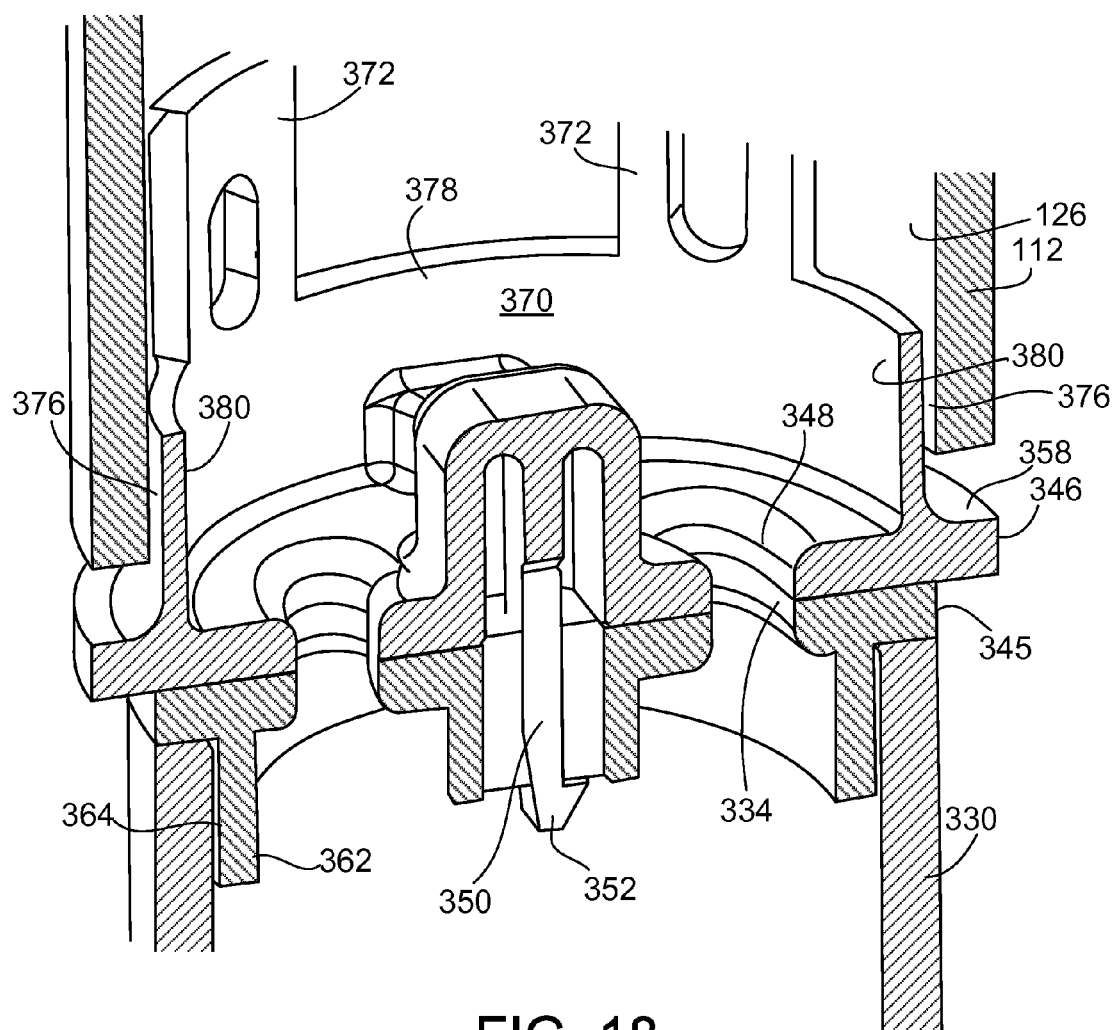
FIG. 18 is an enlarged cross-sectional view of a portion of the cartridge of FIG. 14 when connected to a mouthpiece.

Referring to FIG. 18, the plate valve 346 includes a connection portion 370 that protrudes outward from the valve plate second side 358. The connecting portion 370 is dimensioned to be received within an inner diameter of the mouthpiece 112, and includes first portions 378 that are sized and shaped to engage (e.g. form a press fit connection with) the inner surface of the mouthpiece 112. The connecting portion also includes second portions 380 that are sized and shaped to be spaced apart from the inner surface 126 of the mouthpiece 112 when assembled therewith. The space between the outer surfaces of the second portions 380 of the connection portion 370 and the mouthpiece inner surface 126 provide an air bypass port 376, permitting air flow into the mouthpiece fluid flow passage 116. In addition, the connection portion 370 includes arms 372 that are configured to form a snap fit engagement with corresponding grooves 128 formed in an inner surface of the mouthpiece 112, and partitions 374 that form a generally semi-circular wall. When the plate valve 346 is in the first position, a partition 374 partially surrounds each cartridge inlet 336, directing air flow into the reservoir 332 of the housing 330. As in the previous embodiment, the partitions 374 are arranged so that the cartridge inlets 336 are located on an outer side of the connection portion 370.

When the cartridge 314 is connected to inlet end of the mouthpiece 112, and the plate valve 346 is in the first (e.g., open) position, the mouthpiece 112 and the cartridge 314 together define a flow path through the device 100. Thus, when a user places the outlet 122 of the mouthpiece 112 in his or her mouth and inhales, air flows into the reservoir 332 through cartridge inlets 336. Air then flows from the reservoir 332 through the cartridge outlet 336 and into the inlet 124 of the mouthpiece 112. Air is drawn into the mouthpiece 112 through both the mouthpiece inlet 124 and the air bypass port 376. The air flows along the fluid flow passage 116, and exits the mouthpiece 112 via the mouthpiece outlet 122. Contact with the airflow directing member 118 deflects the air flowing out of the mouthpiece 112. In the illustrated embodiment, the airflow directing member deflects the air flowing out of the mouthpiece 112 to a direction perpendicular to a longitudinal axis 125 of the mouthpiece 112.

Referring to FIGS. 19-24, another disposable and/or replaceable cartridge 414 can be used with the mouthpiece 112 and includes a sealing or closing device operable on the cartridge to permit selective opening and closing of the cartridge inlets and outlets. In this embodiment, the cartridge 414 includes a housing that is an assembly of two components 440, 460 that are slidably connected in a telescoping manner to permit selection between the open and closed configuration as discussed further below.

The cartridge 414 includes a connection portion 440, and a base portion 462 that is slideably connected to the connection portion so as to be movable relative to the connection portion along a longitudinal axis 402 of the cartridge 414, while remaining engaged with the connection portion 440.

The connection portion 440 is a hollow cylindrical member having a closed first end 442, an open second end 444 opposed to the first end 442, and an annular sidewall 446 that extends between the first and second ends 442, 444. The closed first end 442 is formed having a central opening (e.g., cartridge outlet) 434. The outer surface of the sidewall 446 includes a pair of grooves (e.g., cartridge inlets) 436 that extend along an axial direction of the connection portion 440. The cartridge inlets 436 begin at the connection portion second end 444 and end midway between the connection portion first end 442 and second end 444. The cartridge inlets 436 have a depth that is less than the sidewall thickness, except in the region adjacent the second end 444, where the cartridge inlets 436 extend through the thickness of the sidewall 446.

Figure 24:
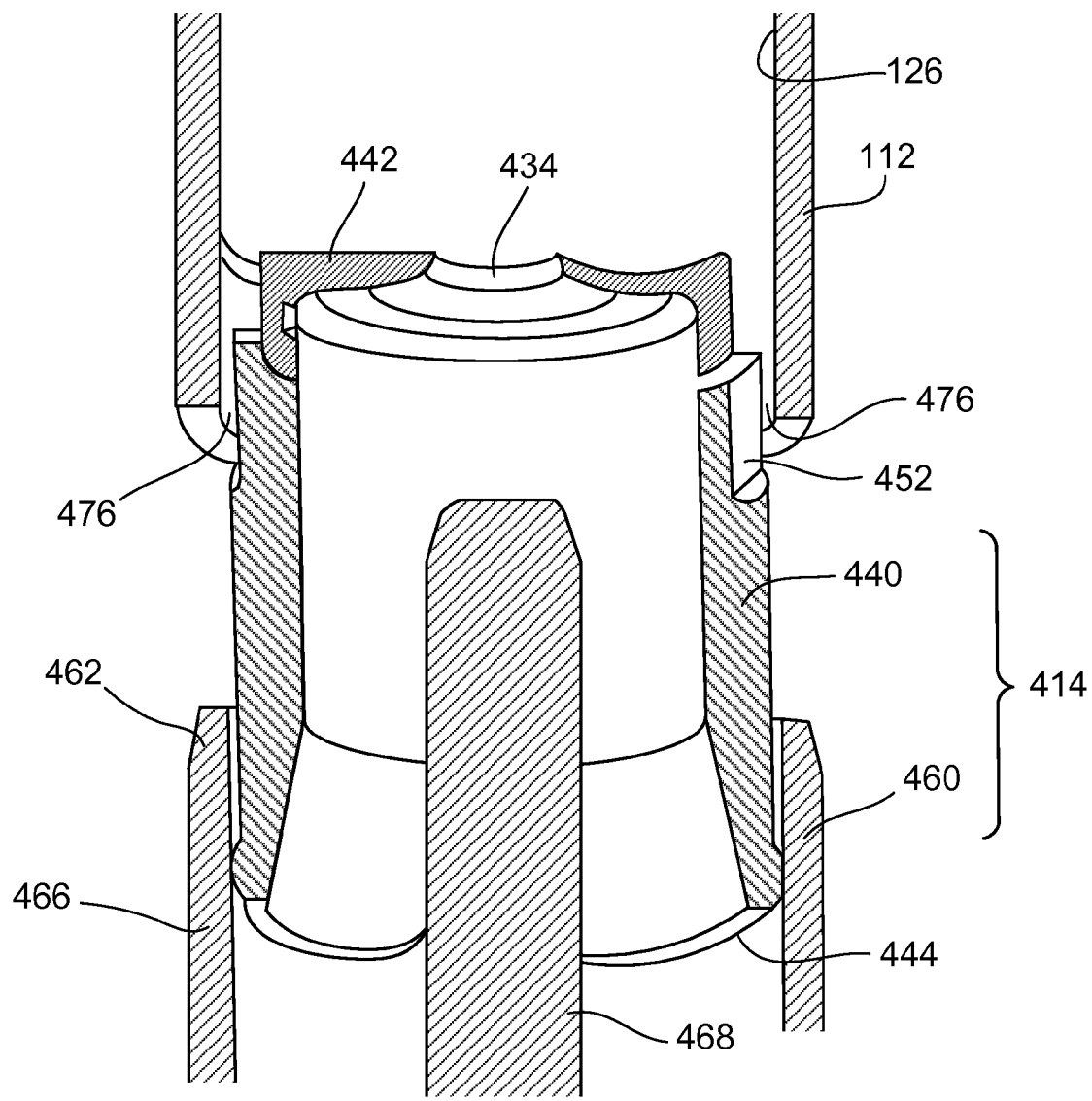
FIG. 24 is an enlarged cross-sectional view of a portion of the particle delivery device of FIG. 19.

The connection portion 440 includes external screw threads 454 provided at the first end 442 that are configured to engage corresponding screw threads (not shown) formed on the inner surface 126 of the mouthpiece 112. In addition, flat regions 452 are formed in the outer surface of the connection portion 440 adjacent to the screw threads 454 at the connection portion first end 442. When the cartridge 414 is connected to the mouthpiece 112 via the screw threads 454, a space is formed between the mouthpiece interior surface 126 and the flat regions 452, forming an air bypass port 476 that permits air flow into the mouthpiece fluid flow passage 116 (FIG. 24).

The base portion 460 is a hollow cylindrical member having an open first end 462, a closed second end 464 opposed to the first end 462, and an annular sidewall 466 that extends between the first and second ends 462, 464. The base portion 460 includes a post 468 that protrudes from a center of the inside surface of the second end 464 toward the base first end 462 and is surrounded by the sidewall 466. The post 468 has an axial length that is greater than the axial length of the sidewall 466 so that post 468 extends through the base open first end 462 and the terminal end 470 of the post 468 resides outside the base portion 460. In addition, tabs 472 are formed on an inner surface of the base portion sidewall 466 at the first end 462 that are configured to be received in and engage with corresponding axially-extending channels 456 formed on an outer surface of the connection portion 440.

The outer dimension of the connection portion sidewall 446 is sized so that the connection portion second end (e.g., open end) 444 is received within the base portion first end (e.g. open end) 462, and an outer surface of the connection portion sidewall 446 contacts an inner surface of the base portion sidewall 466. In particular, the connection portion 440 is engaged with the base portion 460 to define a reservoir 432 that extends between the connection portion first end 442 and the base portion second end 464. When the connection portion 440 is assembled with the base portion 460, the base portion tabs 470 engage the axially-extending channels 456 formed on an outer surface of the connection portion 440, permitting the connection portion 440 to move axially (e.g., telescope) relative to the base portion 460. In this regard, the engagement between the tabs 470 and the channels serves to prevent separation of the connection portion 440 from the base portion 460, and the channels 456 serve as guides that determine the extent of axial movement of the connection portion 440 relative to the base portion 460.

The connection portion 440 telescopes relative to the base portion 460 between a first (e.g., open) position (FIGS. 19 and 20) and a second (e.g., closed) position (FIGS. 21 and 22). In the first (open) position, the connection portion 440 is moved outward relative to the base portion 460 such that a space exists between the connection portion first end 442 and the post terminal end 470, such that the cartridge outlet is open and fluid communication exists between the reservoir 432 and the exterior of the cartridge 414. In addition, in the first position, the cartridge inlets 436 are positioned relative to the base portion 460 so that at least a portion of the cartridge inlets 436 protrude beyond the base portion second end 472, permitting air flow into the reservoir 432 via the cartridge inlets 436, which form a passageway between an inner surface of the base portion 460 and an outer surface of the connection portion 440. In the second (closed) position, the connection portion 440 is moved inward relative to the base portion 460 such that the post terminal end 470 resides within and substantially fully obstructs the cartridge outlet 434. In addition, in the second position, the cartridge inlets 436 are positioned relative to the base portion 460 so that the cartridge inlets 436 reside within the base portion whereby the base portion sidewall 466 substantially fully obstructs the cartridge inlet 436. Moreover, since the connection portion 440 telescopes relative to the base portion 460, the reservoir 432 has a variable volume. In particular, the reservoir has a first volume when the cartridge 414 is in the first (open) position, and a second volume when the cartridge 414 is in the second (closed) position, where the first volume is greater than the second volume.

In the embodiment illustrated in FIGS. 4-10, the cartridge 114 is connected to the mouthpiece via a snap fit connection, but the cartridge 114 is not limited to a snap fit connection. Various strategies are contemplated for attaching the reusable and/or replaceable cartridges 114, 214, 314, 414, 712, 712', 712" described herein to the mouthpiece 112. In some embodiments, a first end 128 of the cartridge 114 has an outer surface that is sized and configured to provide a snap-fit engagement with the inner surface of the corresponding end of the mouthpiece 112. In some embodiments, other forms of engagement are used instead of or in addition to snap-fit engagement to attach the cartridge 114 to the mouthpiece 112. In certain configurations, the cartridge 114 is held or locked into position through mechanical tension and/or frictional forces from the particular mounting design. For example, in some embodiments, the end cap 114 and the mouthpiece 112 have threads and are screwed together (see for example FIGS. 19-24). In another example, cartridges are slidably and reversibly interference or press fit pressed into position within the inlet end of the mouthpiece 112. In some embodiments, the inlet end of the mouthpiece 112 is of a slightly larger diameter than the diameter of the corresponding mating end of the cartridge 114, creating a press-fit configuration between the pieces (see for example FIGS. 11-13). In other embodiments, the mouthpiece and cartridge are locked into position with spring tension locating pins, dowels, ball bearings, living hinge positioners, etc. In still other embodiments, the cartridge 114 is held into place with the mouthpiece via magnetic holders and a ferrous and/or magnetic counterpiece. Other alternative structures for connecting the cartridge 114 to the mouthpiece 112 embodied in the present invention include, but are not limited to, a screw fit, twist fit, snap fit, press fit and turn, bayonet mount, etc.

In some embodiments, the cartridge 114, 214, 314, 414, 712, 712', 712" is formed of a resilient material.

In some embodiments, the components constituting the cartridge 114, 214, 314, 414, 712, 712', 712" are manufactured from a plastic. In certain embodiments, the plastic is biodegradable. In other certain embodiments, the components constituting the cartridge 114, 214, 314, 414, 712, 712', 712" are manufactured from a polyester, a polyhydroxyalkanoate, a polyanhydride, a polycaprolactone, a polydiaxonone, a polyglycolide, a polyhydroxybutyrate, a polylactic acid, a polypropylene carbonate, a polylactic-co-glycolic acid, a poly(3-hydroxybutyrate-co-3-hydroxyvalerate, a polyvinyl alcohol, a starch derivative, cellulose esters, a cellophane, an enhanced biodegradable plastic, compositional variants thereof, combinations thereof, etc.

In certain embodiments the cartridge 114, 214, 314, 414, 712, 712', 712" is edible and manufactured from a starch, a grain-based food, a vegetable, a meat, a fruit, a dairy product, a sugary food, a nut, a confection, a plant product, processed edible products thereof, synthetic edible products thereof, combinations of edible products, etc.

In certain embodiments the cartridge 114, 214, 314, 414, 712, 712', 712" is edible or biodegradable, and manufactured from chocolate, bread, fruit, sugar, meat, bread, pasta, processed forms thereof, combinations thereof, etc.

In some embodiments, the body of the entire device 100 is manufactured from a starch, a grain-based food, a vegetable, a meat, a fruit, a dairy product, a sugary food, a nut, a confection, a plant product, processed edible products thereof, synthetic edible products thereof, combinations of edible products, etc.

In some embodiments, the device 100 may be similar to an inhaler or inhalation device, such as a dry powder inhaler (DPI) or metered dose inhaler (MDI); a "pot" that holds an ultrasound source and confines somewhat the aerosol cloud produced by the source; a "fountain" that ejects and/or circulates the aerosol; a hand-held pump device; a compressed air device; a food straw device; a multi-person, communal device; a tabletop device. A variety of materials may be used to form the device, or parts thereof, including: plastics (e.g. polycarbonates, which are relatively strong, polypropylene, acrylonitrile butadiene styrene, polyethylene, etc.), various metals, glass, cardboard, rigid paper, etc.

In some embodiments, the device 100 includes an aerosol generating device, for example, an airflow disrupting "grating," through which air and powder flows, thereby yielding an aerosol for delivery to the user. In certain embodiments, the airflow grating functions to allow passage of particles having a desired size, range of desired sizes (mean volume distribution), or otherwise delimits flow of particles to the user that are outside of a desired mean volume size distribution range.

In certain embodiments, the aerosolizing device 100, 700 includes a disposable and/or replaceable cartridge (i.e., cartridge 114, 214, 314, 414, 712, 712', 712"). For example, the reusable or replaceable cartridge is selectively detachable from the mouthpiece and has a volume separate from the mouthpiece and includes an inlet and/or outlet port that can be closed or sealed. This is advantageous in the event that not all the payload has been delivered, since the device can be selectively placed in a closed configuration until further usage at a later time. In addition, a closable or sealable device is advantageous in situations wherein the user exchanges one cartridge for another cartridge without having expended all payload in the first cartridge. The partially used, sealed first cartridge can be reconnected to the mouthpiece at a later time for further use.

The cartridge 114, 214, 314, 414, 712, 712', 712" may not be readily opened to access the consumable product inside. This is advantageous for instances in which it is preferable that the user have limited direct access to the consumable product (i.e., access other than by delivery via the mouthpiece as intended). This may be the case when the consumable product is a controlled substance, a sensitive substance, or a substance that requires a very precise dose. This may also reduce the risk of a user inserting other materials into the device.

In some embodiments, the cartridge 114, 214, 314, 414, 712, 712', 712" is an assembly of multiple components that together define concave inner spaces, and, after powder is filled into either or all of the components, the components snap or screw together to form a largely closed interior chamber. In some embodiments, the cartridge 114 further include an aerosol generating device, for example, an airflow-disrupting "grating" (not shown), through which air and powder flow, thereby yielding an aerosol for delivery to the user. The cartridge typically includes air passageways, for example, on the respective ends of the enclosed compartments, so as to allow air to flow through upon inhalation. The design, for example, the size or shape of the air passageways, should provide sufficient airflow while minimizing powder loss.

In the illustrated embodiments, the cartridge 114, 214, 314, 414, 712, 712', 712" includes upper element (e.g., cover or cover assembly) and lower element (e.g., housing). While a consumer is not able to readily separate the upper and lower elements, the two elements may initially separate so as to permit filling of the cartridge 114, 214, 314, 414, 712, 712', 712" during the manufacture of the overall product. In this embodiment, the housing is filled with the consumable product during the manufacture of the overall product, and shortly thereafter, the cover or cover assembly is affixed to the housing, for example by a snap fit. The snap fit can be designed to resist being taken apart once the two elements are affixed. In some embodiments, other methods of attachment such as, for example, press fits and ultrasonic welding can be used to attach the cover and the housing.

In some embodiments, the mouthpiece and cartridge are designed for single use (perhaps disposable) or, alternatively, designed for multiple use. For example, in some embodiments, the cartridge may be disposable, and, optionally, available with a variety of aerosolizable powders, while the mouthpiece may be reusable. In some cases, prefilled cartridges could be punctured, torn, cut or broken by design elements within the housing or mouthpiece (for example, sharp points, blades, compressing the device, or twisting the device etc.). In certain embodiments, pre-filled standard-sized capsules, for example, a gel capsule, blister pack, or sealed capsule of another form, can be used by placing them in the cartridge reservoir 132. Such embodiments allow for easier filling, substitution, cleaning, and disposal. In addition, such embodiments allow for manufacture of multiple dose capsules. Such pre-filled capsules could be punctured, torn, cut or broken by design elements within the housing (for example, sharp points, blades, compressing the device, or twisting the device etc.) prior to use. In some cases, a sealing member is removed; for example, a sealing plastic or metal foil initially adhering to the capsule (or cap) can be peeled off. In some cases, the capsule can be protected or sealed with a cover. The product may thus be released into the reservoir 132, for example, and become more susceptible to airflow generated during inhalation or activation. In another embodiment, the aerosolizable product may remain substantially within the original container but now be in fluid communication with, and thus now susceptible to, airflow generated during inhalation and/or activation, etc. After activation and use, the emptied capsule could be removed from the reservoir 132. Alternatively, the cartridge can be designed for multiple uses. For example, the cartridge may be refillable. In some cases, the cartridge may be designed for one or more uses, and not be itself refillable. In some cases, used (e.g., empty) cartridge can be readily removed from contact, or removed from fluid communication, with the mouthpiece 112. In some cases, new (e.g., filled) cartridge can be readily brought into contact or fluid communication with the mouthpiece 112. In some cases, such fluid communication can be achieved using clean or sterile components.

Figure 25A:
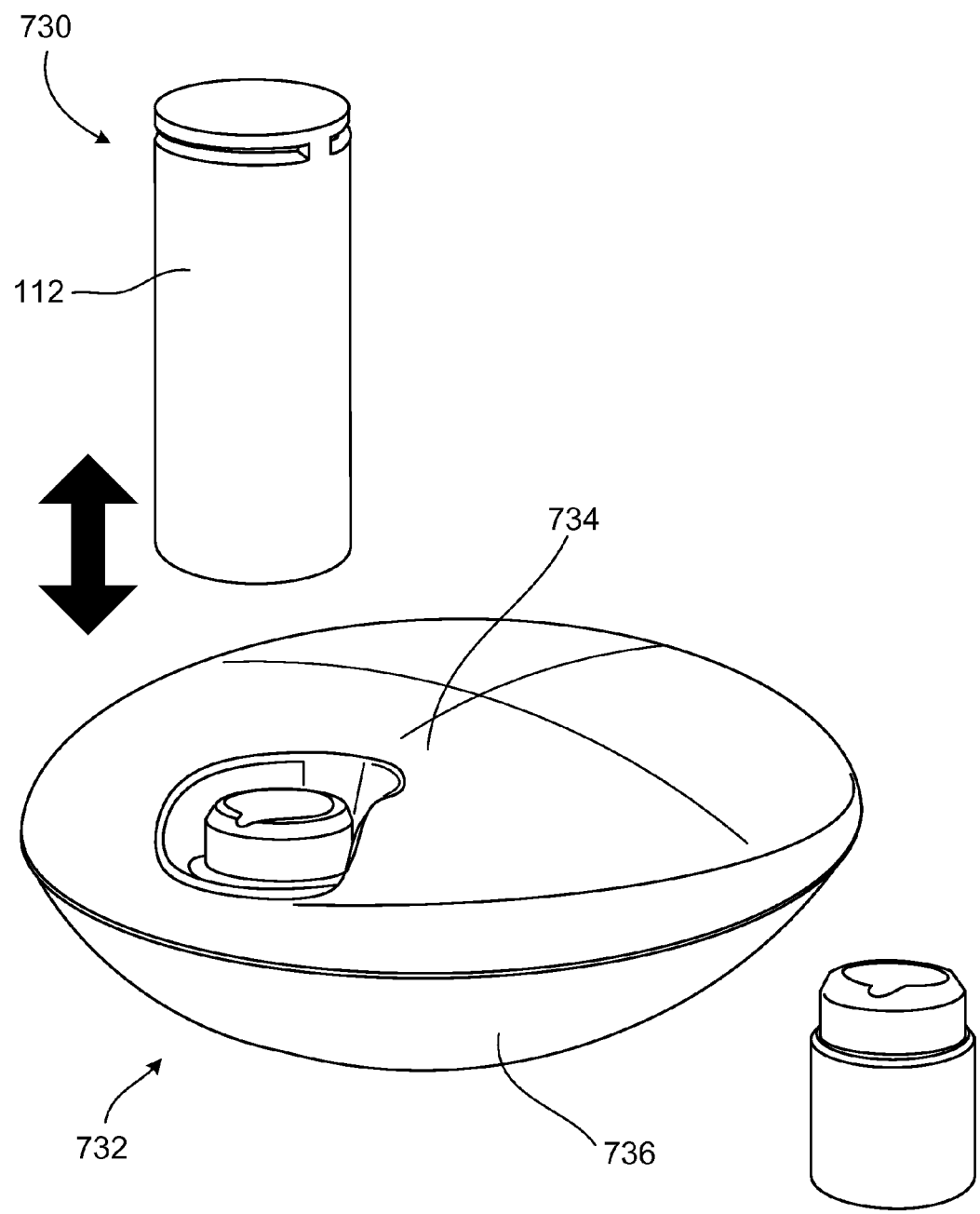
FIGS. 25A-C are schematics of a particle delivery apparatus with multiple capsules or cartridges and a reusable mouthpiece.
Figure 25B:
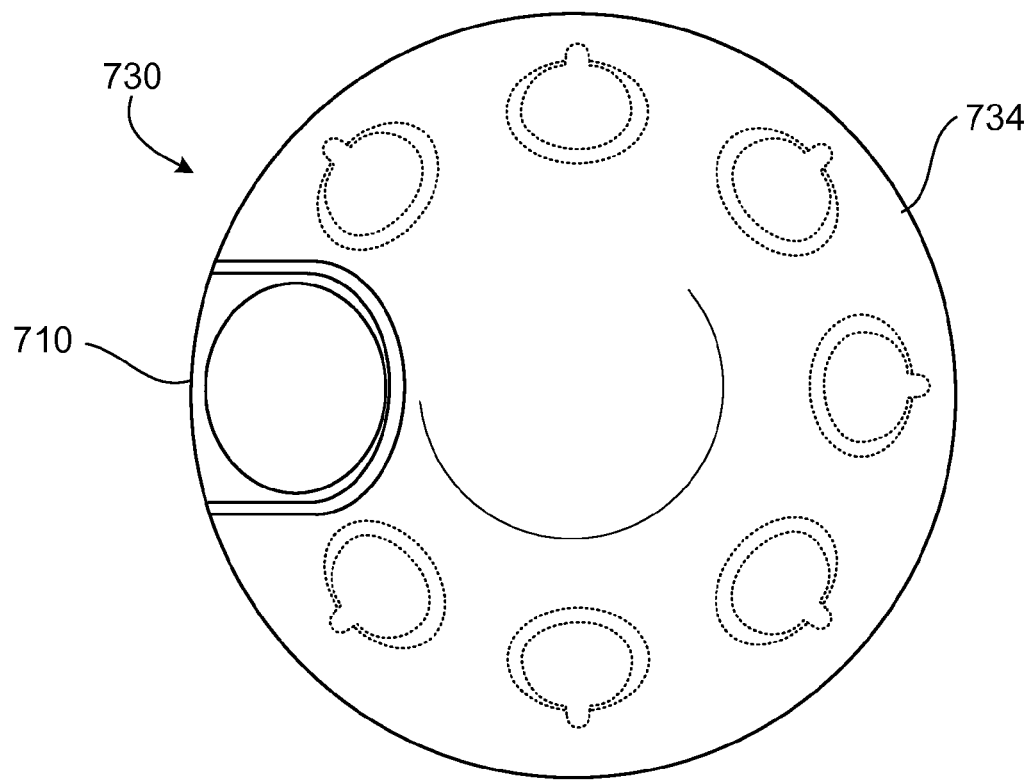
Figure 25C:
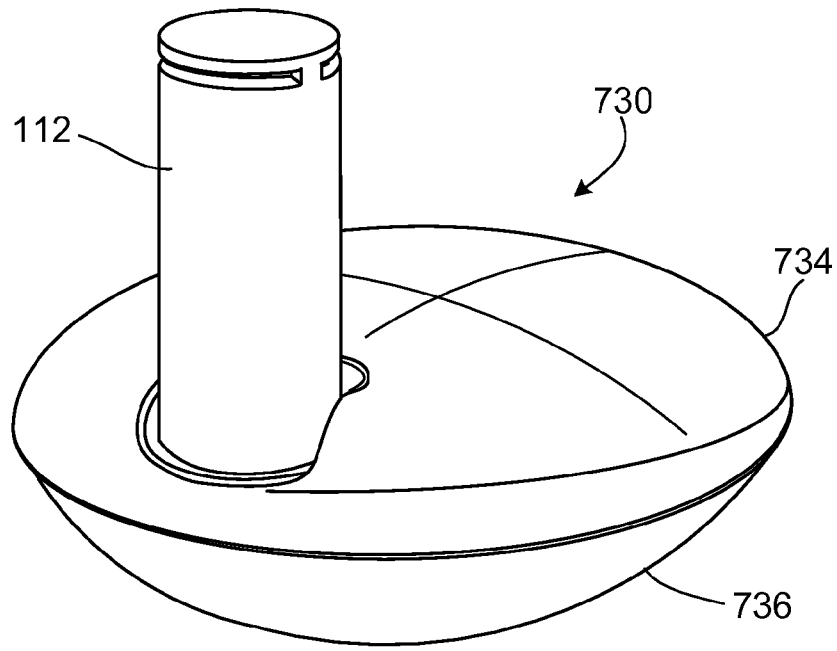

In some embodiments, a cartridge can contain more than one dose. For example, in some embodiments, multiple doses are contained within a single larger cartridge, in which different doses are physically separated from each other. In some embodiments, a mouthpiece 112 is in fluid communication with only one of these doses at a given time during use. Once the dose is delivered, it is possible for the mouthpiece 112 to be put in fluid communication with a different dose container within the cartridge, containing a new dose of consumable product. As such, a single mouthpiece 112, and a single cartridge 114, can be used to deliver multiple doses. After consuming all doses within a cartridge element, the cartridge element may be replaced or refilled. In some embodiments, the housing 130, 230, 330, 430 is designed to allow for the incorporation of at least 2, for example, 3, 4, 5, 6, 7, 8, 9 or 10, cartridge, thereby allowing, for example, the user to mix and match a variety of flavors in various amounts as desired. In some embodiments, the housing 130 could be designed to allow for the loading of a set of multiple cartridges to be activated one at a time, thus reducing the frequency of removing and replacing spent cartridges. A particle delivery apparatus can contain a cartridge element that comprises more than one dose of consumable product. The mouthpiece and cartridge element can both be reusable, while individual dose containers can be disposable and/or replaceable. In FIG. 25A, apparatus 730 comprises a reusable capsule and/or cartridge element 732, in which 8 doses of consumable product are physically isolated. Some embodiments are configured with a different maximum capacity of a cartridge. Reusable mouthpiece 112 can be releasably coupled to cartridge element 732 on the upper side 734 of the cartridge element 732. Upper side 734 can rotate relative to lower side 736, sequentially exposing different individual dose containers within cartridge element 734. Reusable mouthpiece 112 can be coupled to each of these doses one at a time, and thus used to deliver, sequentially, all doses contained in cartridge element 734. In this embodiment, once all doses are used, upper side 734 can be separated from lower side 736, and new dose containers can be added into cartridge element 732. In some cases, new dose containers can be added individually without the need to separate upper side 734 from lower side 736, by sequentially rotating upper side 734 relative to lower side 736.

In some cases, each individual dose container is sealed by a thin member that must be peeled off before coupling with the mouthpiece 112.

In some embodiments, cartridge element 732 is itself entirely disposable, and can be replaced with a new cartridge element 732 when the doses are all used.

In some embodiments, the device 100 is designed for use by at least 2, for example, 3, 4, 5, 6, 7, 8, 9 or 10, users. For example, the device could be designed with multiple branches, each designed with an airflow directing element, so as to allow for simultaneous use by multiple users.

In certain aspects, the device 100, 700 may include a housing, a cartridge and a cap. In alternative aspects, a device includes the housing and a cap, wherein both the housing and the cap are designed for use with cartridges, for example, disposable or refillable cartridges. In other aspects, the device encompasses disposable or refillable cartridges. In other aspects, the device encompasses mouthpieces, used with a variety of aerosolizable products, aerosolizable product sources, and/or aerosolizable product containers.

Figure 27:
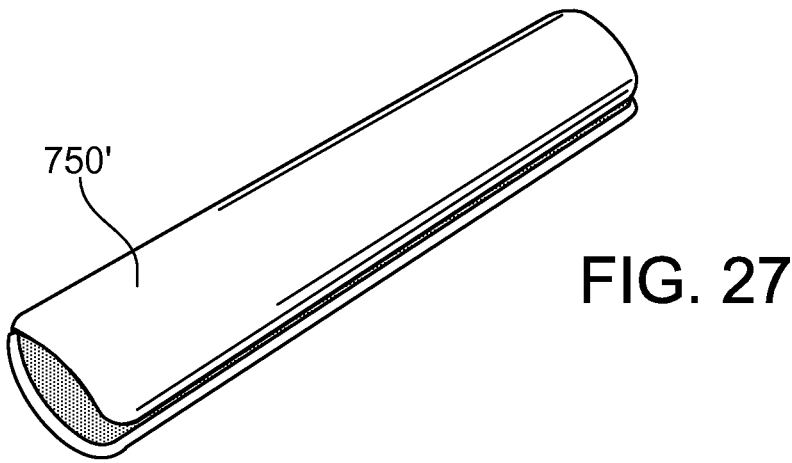
FIG. 27 is a perspective view of a carrying case embodiment.
Figure 28:
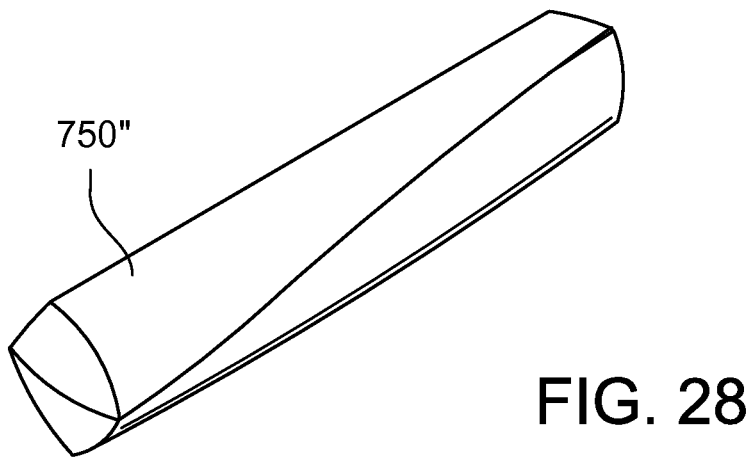
FIG. 28 is a perspective view of a carrying case embodiment.
Figure 29:
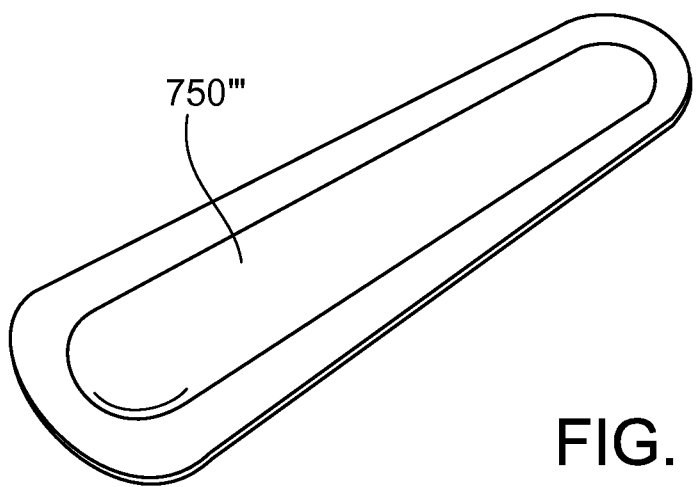
FIG. 29 is a perspective view of a carrying case embodiment.

In certain aspects is a carrying case for transporting the device and a plurality of cartridges. FIGS. 26A-26C are views of a case 750 for carrying a mouthpiece and associated cartridges. FIGS. 27-29 are perspective views of other carrying case embodiments 750', 750", 750'".

It should be noted that the functionalities (i.e., aerosolizable product containment, aerosol generation, aerosol delivery, airflow (and aerosol) direction, etc.) of the mouthpiece, cartridge, cap, grating, mouthpiece disc, etc. may, in some embodiments, be associated with one or more potentially different physical units, while maintaining the same overall functionality. For example, in some embodiments, a single device unit may incorporate all functional aspects. In some embodiments, a mouthpiece may contain an aerosol-generating device, an aerosol delivery device, and an airflow- (and aerosol-) directing device, and the aerosolizable product container may be separate. In some embodiments, as previously described, food product may be contained within a cartridge, an aerosol generating device may be part of a cartridge, and a mouthpiece with airflow-directing elements may be used to deliver the aerosol from the cartridge to the user.

The device 100, 700, or parts of the device, may be designed for single use (for example, disposable). In some embodiments, certain parts of the device, including the mouthpiece 112 or the cartridge 114, may be disposable.

The device 100, 700 itself, or parts of the device, may be designed for multiuse. In some embodiments, for example, the dosage cartridge is replaceable or the reservoir 132 may be refilled. In other embodiments, a reusable mouthpiece may be used with a disposable cartridge element, the latter containing more than one dose, with all doses intended to be delivered using the reusable mouthpiece. In still other embodiments, a reusable mouthpiece may be used with a disposable and/or replaceable cartridge that contains the aerosolizable product, as discussed further below.

In some embodiments, cartridge or cartridge elements contain a single dose. In some embodiments, cartridge or cartridge elements contain more than one dose. In some embodiments, cartridges (e.g., consumable-product-containing elements) may be disposable and designed to deliver a consumable product dosage 1, 2, 5, 10, 15, 30, or more times, before being discarded.

In some embodiments, each dose is physically separated from the others, while contained in the cartridge or cartridge element. In other embodiments, multiple doses of a consumable product are contained within a single physical device, device element or cartridge, and dosing is regulated by the user or by some other means, as needed.

In some embodiments, the device may incorporate a force-generating mechanism, such as a pump or compressed air source, to aerosolize the product. In some embodiments, the device may incorporate a propellant.

In some embodiments, the device may be designed for "single action", "repeated action", or "continuous action" aerosolization and/or delivery, depending on whether it is intended to aerosolize and/or deliver the product in a single, short-term step (e.g., one inhalation on an inhalation-triggered apparatus), in multiple discrete steps (e.g., multiple inhalations on an inhalation-triggered apparatus), or over a longer-term continuous step (e.g., maintaining an aerosol cloud in open air), where "step" can refer to any combination of simultaneous and/or sequential processes by which the device aerosolizes and/or delivers the product. Many factors, including whether the device is intended for use by one subject or multiple subjects at a time, will help determine which of these step sequences (if any) is appropriate for any particular embodiment.

In the illustrated embodiments, the mouthpiece 112 is formed having a circular or oval cross section, but it is not limited to these cross-sectional shapes. For example, the mouthpiece can have a square or rectangular cross-sectional shape.

In the illustrated embodiment, the mouthpiece 112 is a monolithic structure (e.g., formed of a single piece). However, in other embodiments, the mouthpiece 112 can be an assembly of at least two substructures. For example, the mouthpiece can be an assembly of an end piece with a deflection member designed for oral placement and a body that connects the mouthpiece to a consumable particle cartridge and/or capsule. In another example, the mouthpiece can be an assembly of three separate components including an end piece for oral placement, a deflector which may or may not be detachable from the end piece, and a body that connects the end piece to a consumable particle cartridge and/or capsule. Other configurations of a mouthpiece with equivalent function to that as described herein are contemplated. Other mouthpieces can be used with aerosolized particle delivery devices.

In some embodiments, the mouthpiece 112 is manufactured from a plastic. In certain embodiments, the plastic is biodegradable. In other certain embodiments, the mouthpiece 112 is manufactured from a polyester, a polyhydroxyalkanoate, a polyanhydride, a polycaprolactone, a polydiaxonone, a polyglycolide, a polyhydroxybutyrate, a polylactic acid, a polypropylene carbonate, a polylactic-co-glycolic acid, a poly(3-hydroxybutyrate-co-3-hydroxyvalerate, a polyvinyl alcohol, a starch derivative, cellulose esters, a cellophane, an enhanced biodegradable plastic, compositional variants thereof, combinations thereof, etc.

In some implementations, the mouthpiece 112 is intended to be reused, for example, for 2, 5, 10, 50, 100, or more deliveries of consumable product. In certain embodiments, reusable parts of the device can be used indefinitely (e.g., they can be readily cleaned, in a dishwasher, by hand, etc.). For example, a mouthpiece made of a durable and cleanable material, such as certain metals (i.e., stainless steel), plastics, ceramic or glass, may be used in conjunction with many cartridges over time.

In other implementations, the mouthpiece 112 can be re-used, for example, with multiple cartridges of the same type (e.g., of the same embodiment), or in another example, with cartridge of different types (e.g. of a different embodiment).

In other implementations, the other mouthpieces may be used with the cartridge 114, 214, 314, 414, 712, 712', 712".

In some implementations, the delivery device 100 comprises a disposable and/or replaceable cartridge 114, 214, 314, 414, 712, 712', 712". For example, the reusable or replaceable cartridge is selectively detachable from the mouthpiece 112, and has a reservoir 132 separate from the mouthpiece 112 that includes an inlet and/or outlet port that can be closed or sealed. This is advantageous in the event that not all the payload has been delivered, since the device can be selectively placed in a closed configuration until further usage at a later time. In addition, a closable or sealable device is advantageous in situations wherein the user exchanges one cartridge for another cartridge without having expended all payload in the first cartridge. The partially used, sealed first cartridge can be reconnected to the mouthpiece at a later time for further use.

In the cartridge 114 illustrated in FIGS. 4-10, the cartridge inlet and outlet ports can be selectively sealed or closed to prevent aerosolizable product from leaking or spilling out of the cartridge without requiring connectivity to remainder of the device (e.g., the mouthpiece). In the illustrated embodiment, the spring-loaded tab 146 was used to provide control of the flow through the cartridge inlets and outlet, but the cartridge is not limited to this control device. Other control devices may be used, including mechanical devices wherein manual (digital) manipulation of the device open or closes the air inlet and/or payload outlet ports. In particular embodiments, spring-activated doors or levers are opened through actuation of a lever, handle, button or other functionally similar member to open the air inlet and/or outlet ports. In some embodiments, actively holding the member in an open position retains the device in a conformation for which an air expiration or inspiration aerosolizes and delivers a payload product. Releasing the member will result in the ports being closed by a spring tension wherein the port door, lid, flap, cover and the like close the ports to prevent air flow through the device and/or spillage of the product. In certain embodiments, a spring member is attached to the door or covering. In other certain embodiments, the spring member is attached to a lever, handle, button or other functionally similar member, which in turn actuates a port door or cover to seal or close the port(s). In still other embodiments, the members of the closing mechanism are comprised of a material and/or composition having a spring tension either in the handle/lever/button, the door/lid/flap/seal/cover, or both. Living hinges such as these do not require a separate but connected spring member for actuation of the living hinge sealing/closing mechanism, and decrease the total number of separately manufactured and assembled device members. In certain embodiments, the actuating mechanism for a spring tension device may be opened and placed into a locked position, wherein the air flow through the device is achieved without holding the actuating mechanism. Maneuvering the actuating mechanism will unlock the mechanism, wherein spring tension (and not the device user) closes the door/lid/flap/seal/cover. In some embodiments, a lever, button or handle is actuated to maneuver a door/seal/lid/flap/cover to overlay one or more ports. In certain embodiments, a mechanism like this can be locked into an open and/or closed position, and requires a device user to actively switch the device between an open and closed conformation.

In the cartridge 414 illustrated in FIGS. 19-24, the cartridge inlet and outlet ports can be selectively sealed or closed to prevent aerosolizable product from leaking or spilling out of the cartridge without requiring connectivity to remainder of the device (e.g., the mouthpiece). In the embodiment illustrated in FIGS. 19-24, the structure of the housing itself, including the post and features of the external surface, were used to control fluid flow through the cartridge inlets and outlet, but the cartridge is not limited to this control device. Alternative embodiments are contemplated for the cartridge including, for example, the cartridge being comprised of a single member or more than one member to define the inner volume. In a particular embodiment, the replaceable/reusable cartridge inner volume is a single member molded with one or more components into a single functional cartridge. In another particular embodiment, the replaceable/reusable cartridge is comprised of two components that are slidably connected, wherein each component defines a cylindrical or elongated closed end, an open end, wall, etc. The slidably connected members thus define the cartridge (second) volume. One advantage to such a configuration is that the one member of the slidably connected members can be configured to connect with the mouth piece (first member), and slidably separating or pushing together the other member of the slidably connected members actuates a sealing mechanism. In certain embodiments, o-rings, rubber, silicon, etc. seals, edge geometry (for example, a bevel), or cartridge material is pliable between the interconnected members to sufficiently seal the cartridge from powder leakage at the inner and outer cartridge member interface.

In many instances, variations of some embodiments may be designed without, in many instances, affecting the function of the overall device. For example, the cylindrical nature of the device may be modified, for example, for aesthetic effect, as may the overall length of the device. Alternatively, or in addition, the aerosol generating device, for example, the airflow disrupting element such as a grating, may be incorporated into the cylindrical mouthpiece unit. In some embodiments, the aerosol generating device may include more than one component. For example, a grating and/or the airflow passageways in the cap may play individual roles in generating turbulence that leads to aerosolization, or both may be needed. In general, there may also be multiple configurations of gratings, airflow passageways, dimensions etc, to produce the right aerosolization airflow.

In some embodiments, the dimensions of the device may be selected so that, while preserving the appropriate airflow dynamics, aerosolizable product may be provided as capsule that is placed within the cartridge 114, 214, 314, 414, 712, 712', 712". For example, standard medical capsules may be placed within the cartridge 114, 214, 314, 414, 712, 712', 712", or may to some extent replace the previously described aerosolizable particles, or in another way simplify the process of loading, storing, and releasing the powder.

The embodiments of the disposable and/or replaceable cartridge 114, 214, 314, 414, 712, 712', 712" described herein each include a sealing or closing device operable on the cartridge to permit selective opening and closing of the cartridge inlets and outlets. The open and closed configurations can affect either the airflow through the cartridge, and/or close the cartridge to prevent payload spillage when the device is not in use. In the described implementations, the sealing device is operable on the cartridge, independent of the mouthpiece. However, in other implementations, the sealing device may require both the mouthpiece and the cartridge either to engagably seal/close/cover or allow an open configuration of the cartridge. For example, in a particular embodiment, the mouthpiece terminal edge slidably abuts the cartridge edge. When the two edges are contacting, the air inlet ports are sealed or closed with the edge or other device articulations, thereby preventing payload spillage out of the air intake ports, aerosol flow outlet ports, bypass ports, etc. Such a configuration can also utilize, for example, an internal endcap or similar conformation on the mouthpiece that will slidably abut the payload outlet port of the cartridge. In a closed position, therefore, the any or all of the various ports will be closed when the mouthpiece is slidably abutted to the replaceable cartridge, thereby minimizing or eliminating payload spillage from the internal cartridge payload volume. In certain embodiments, o-rings, rubber, silicon, etc. seals, edge geometry (for example, a bevel), or cartridge material is pliable between the interconnected members to sufficiently seal the cartridge from powder leakage at the inner and outer cartridge member interface.

Activation of Aerosolization and Delivery of Consumable Product

The aerosol generating device is any device capable of producing an aerosol of desired characteristics (i.e., particle size, airborne time/suspension duration, emitted dose, etc.). In addition to the aerosol generating device, there may be a delivery device, such as an additional airflow constraining device, a confined space in which the aerosol is contained, an air passage in an inhaler, a mouthpiece, airflow-directing elements, or other devices or structures, that enable, facilitate, or optimize the delivery of the aerosol to the subject's mouth. For example, FIGS. 4-10 illustrate the cartridge 114, which in many embodiments serves as an aerosolizable food product container. In some implementations, the cartridge 114 also incorporates an aerosol-generating device consisting primarily of a grating (not shown). In many embodiments, the cartridge 114 is connected to the mouthpiece 112 with airflow-directing elements, where the mouthpiece serves as a delivery device.

By controlling gravitational and inertial forces, the airflow-directing elements found in some embodiments enable delivery of the aerosol cloud substantially to surfaces within the mouth (i.e., tongue, cheeks, etc.) rather than into the respiratory tract. This aspect of the technology is highly relevant to a number of potential applications of aerosolizable products. Indeed the same such delivery device can make possible delivery of a wide range of aerosol products, generated in a number of different ways, to a consumer, while minimizing or eliminating coughing and potential interactions with surfaces of the respiratory system beyond the mouth.

The design of any of the devices described herein is configured for the reduction of the tendency to cough, gag, or otherwise react unfavorably to an aerosolized product, and can be embodied in a variety of designs achieving the same function; The devices described herein are meant to be exemplary.

Aerosolization and delivery of a product may occur by a variety of means including, but not limited to, acts of respiration, device activation, bodily displacement, aerosol displacement and a combination thereof. For example, such acts may include the following: inhalation on a mouthpiece, resulting in exposure of the aerosolizable product to the aerosol generating device and delivery of the aerosolized product to the mouth; the activation of an ultrasound source, the actuation of a pump, the activation of a compressed air source, the activation of an impeller, the puncturing of a container, the opening of an air passage, that at least in part causes or helps to cause a product to aerosolize (the aerosol thus formed may be in a substantially confined space (e.g., a spacer), or a substantially open space (e.g., as a "cloud" in air or in a confined structure)); respiration directed "on" or "toward" an aerosol (e.g., that is contained in a spacer device, freely floating as a cloud or contained within a larger structure), and that may be facilitated by the use of a straw, mouthpiece, or other apparatus, thereby leading to product deposition substantially in the mouth; an act of bodily displacement, such as walking or leaning (possibly in conjunction with a particular placement or positioning of the mouth, tongue, or other body part in a specific way), that exposes a subject's mouth to an aerosol cloud, or portion thereof, thereby leading to particle deposition substantially in the mouth; an act of aerosol displacement caused by, for example, an air current, a thermal or pressure gradient, inertial impaction, diffusion, or gravity, that brings an aerosol cloud, or portion thereof, to a position so as to expose a subject's mouth to the aerosol cloud, thereby leading to particle deposition substantially in the mouth (even where aerosol displacement results in dilution of the particle concentration and spreading out the cloud); an additional act of device activation, device use, space constraining, airflow confinement, etc., or of placement or positioning of the mouth, lips, tongue, jaw, head, or other body part in a particular configuration, shape, etc.; other actions that help produce the proper aerosolization and/or delivery and/or tasting of the aerosolized product (e.g., use of a food straw, opening/closing of a containing chamber, lifting of the tongue to divert airflow, etc.). Such acts may be used to help reduce a tendency to cough, gag, or otherwise react unfavorably to the aerosolized product.

Air flow of the device is moderated for user comfort and aerosolizing capacity of the device. Optimal airflow can be dependent on factors including payload, device design, air inlet port size and configuration, air bypass size and configuration, and overall size of the device. Generally, the device is designed for hand held use. In certain embodiments the aerosolizing delivery apparatus is configured to permit a flow rate through the apparatus of between about five (5) liters per minute and about sixty (60) liters per minute at a vacuum pressure of about four kiloPascals. In certain embodiments the aerosolizing delivery apparatus is configured for a flow rate through the apparatus of between about ten (10) liters per minute and about thirty (30) liters per minute at a vacuum pressure of about four kiloPascals. In certain embodiments the aerosolizing delivery apparatus is configured for a flow rate through the apparatus of between about fifteen (15) liters per minute and about twenty-five (25) liters per minute at a vacuum pressure of about four kiloPascals. It may also be desirable to achieve flow rates that deliver a portion, or all of, the powder contained in the cartridge reservoir or volume in one, two, three, four, five, six, seven, eight, none, ten or more actuations, wherein an actuation is about a one to two second inhalation at about 4 kiloPascals of applied vacuum pressure. In certain embodiments, the payload of delivered powder per actuation at 4 kiloPascals applied vacuum pressure for about 1 to 2 seconds of inhalation, is between five and 10 percent of the starting quantity of powder contained in the cartridge reservoir. In certain embodiments, the payload of delivered powder per actuation at 4 kiloPascals applied vacuum pressure for about 1 to 2 seconds of inhalation, is between ten and twenty percent of the starting quantity of powder contained in the cartridge reservoir. In certain embodiments, the payload of delivered powder per actuation at 4 kiloPascals applied vacuum pressure for about 1 to 2 seconds of inhalation, is between twenty and thirty percent of the starting quantity of powder contained in the cartridge reservoir. In certain embodiments, the payload of delivered powder per actuation at 4 kiloPascals applied vacuum pressure for about 1 to 2 seconds of inhalation, is between thirty and forty percent of the starting quantity of powder contained in the cartridge reservoir. In certain embodiments, the payload of delivered powder per actuation at 4 kiloPascals applied vacuum pressure for about 1 to 2 seconds of inhalation, is between forty and fifty percent of the starting quantity of powder contained in the cartridge reservoir. In certain embodiments, the payload of delivered powder per actuation at 4 kiloPascals applied vacuum pressure for about 1 to 2 seconds of inhalation, is between fifty and sixty percent of the starting quantity of powder contained in the cartridge reservoir. In certain embodiments, the payload of delivered powder per actuation at 4 kiloPascals applied vacuum pressure for about 1 to 2 seconds of inhalation, is between sixty and seventy percent of the starting quantity of powder contained in the cartridge reservoir. In certain embodiments, the payload of delivered powder per actuation at 4 kiloPascals applied vacuum pressure for about 1 to 2 seconds of inhalation, is between seventy and eighty percent of the starting quantity of powder contained in the cartridge reservoir. In certain embodiments, the payload of delivered powder per actuation at 4 kiloPascals applied vacuum pressure for about 1 to 2 seconds of inhalation, is between eighty and ninety percent of the starting quantity of powder contained in the cartridge reservoir. In certain embodiments, the payload of delivered powder per actuation at 4 kiloPascals applied vacuum pressure for about 1 to 2 seconds of inhalation, is between ninety and one hundred percent of the starting quantity of powder contained in the cartridge reservoir.

All references to a powder, liquid, aerosol, cloud, particle, etc. made herein may equivalently refer to some fraction or portion of the total amount of the powder, liquid, aerosol, cloud, etc.

In some embodiments, the aerosolized product should be of a determined size, i.e., of sufficient size to limit entry into the respiratory tract but of small enough size to allow for suspension in the air. In some embodiments, particle size may be a manufacturing requirement of pre-atomized, generally solid products, for example the products placed inside the capsule/cap of certain embodiments, or certain dry products used in association with an air pump or compressed air source. In some embodiments, particle size may be a requirement of the aerosol-generating device, for (generally liquid) products that are only atomized upon aerosol generation, for example the products used in association with ultrasound sources to produce an aerosol cloud.

In some embodiments, the predetermined, mean size of the aerosolized product is at least 1, 2, 3, 4, 5, 10, 15, 20, 25, 30, 35, 40, 45, 50, 55, 60, 70, 75, 80, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 325, 350, 375, 400, 425, 450, 475, or 500 microns. In some embodiments, the predetermined, mean size of the aerosolized product is less than 500, 450, 400, 350, 325, 300, 275, 250, 245, 240, 235, 230, 225, 220, 215, 210, 205, 200, 195, 190, 185, 180, 175, 150, 140, 130, 120, 110, 100, 90, 80, 70, 60, 50, 40, 30, 20, or 10 microns in size. Ranges intermediate to those recited above, e.g., about 50 microns to about 215 microns, are also intended to be part of this disclosure. For example, ranges of values using a combination of any of the above recited values as upper and/or lower limits are intended to be included.

Especially, but not exclusively, in some embodiments in which intake is by inspiration or expiration, minimum particle size is an important feature of the approach. The food aerosol particles are designed to be substantially delivered and deposited into the mouth, for example by the forces of gravity or inertial impaction, but to not be easily delivered and deposited substantially further into the respiratory tract, for example the trachea or lungs. Such consumable particles would thus possess a size larger than that which focuses penetration into the lungs (i.e., larger than about 10 microns). For example, breath-activated aerosolizing devices, such as the devices shown (in part or in whole) in the figures, generate an aerosol that would fairly easily follow the inspired air toward the lungs were it not for the aerosol particles' larger size (and the delivery device's airflow-directing elements).

Especially, but not exclusively, in embodiments in which intake is by displacement of the subject or of the aerosol (e.g., with an aerosol cloud), maximum particle size is an important feature of the approach. Indeed, the aerosol cloud must remain suspended in air for at least a brief time so that displacement into the mouth can occur. Thus the particles must not be so large such that they rapidly settle from the air. This will greatly depend on the force(s) and/or mechanism(s) by which the particles are held in the air (e.g., by "natural" forces alone, such as inertia, diffusion, etc., or by additional forces, such as an impeller, air currents, convection, etc.). Accordingly, in some embodiments, the particles should be less than about 500 microns under typical suspension forces and mechanisms. For example, ultrasound sources in liquid products can produce a standing aerosol cloud that, so long as convection is minimal, balances gravity, diffusion, inertial impaction, and other forces, to stay suspended in the air.

The specific parameters of the apparatus and intake method will in part determine whether the subject is inhaling/exhaling or eating/sipping when intake of the aerosol occurs. This generally corresponds to (1) whether the aerosol is entering the subject's mouth and/or throat via breathed air (physiologically, while the epiglottis is directing the air into the trachea toward the lungs) or whether the aerosol is entering the subject's mouth by another method (such as displacement of the aerosol or of the subject), and (2) whether the subject's manoeuver or expectation is equivalent to the consumption of a food product to be (eventually) swallowed (e.g., with the use of a drinking straw while drawing fluid into the mouth, before swallowing; physiologically, while the epiglottis is blocking passage to the trachea). In any case, it should be further noted that the product, after deposition in the mouth, may be eventually swallowed and consumed essentially as any other typical ingestible product.

In some cases, the aerosol may be carried via inhaled air that flows all the way to the lungs, for example, like the inhalation a smoker may have, which carries air and smoke through/from the cigarette, into the lungs. In some cases, the aerosol may be carried via sucked air that stops in the mouth, more like the approach used with a typical straw and beverage, or with cigars. In some cases, elements of both approaches may be suitable. This potential distinction may have important implications for an aerosolizing device. For example, in the case in which the particles are carried by air that continues directly to the lungs, preventing deposition of particles too far into the respiratory tract is more dependent on the physical parameters of the particles, airflow, etc. In the case in which the particles are carried by air that is sucked into the mouth, it may be possible to carry particles of mean sizes, or with other properties, that would normally allow them to extend further than desirable into the respiratory system, but that, by virtue of the airflow stopping before the lungs, have them fall substantially into the mouth anyway.

In some embodiments of the devices described herein, relatively dry, solid powders of appropriate size can be used as the product. Preliminary tests have shown that the water-solubility of the dry powders used plays a role in the taste and potential coughing reflex resulting from intake of the aerosolized product. For example, powders of particles that tend to be more rapidly water-soluble, such as ground chocolate bars, or certain chocolate-based powders, give rise to a generally pleasing reaction upon contact of the particles with the tongue and other surfaces within the mouth. In the case of ground chocolate bars, for example, the effect is in some cases similar to that of sensing chocolate melt very rapidly in one's mouth. Conversely, particles that are less water-soluble, such as certain ground-cocoa-based powder products, tend to be considered harsher and more likely to elicit less pleasurable reactions, such as a dry-mouth sensation or coughing. However, in some instances, a combination of both kinds of powders, in varying proportions, provides interesting flavor complexity.

Aerosol Powders

By designing a product payload form that can be aerosolized (particles much larger than 500 microns fall quickly out of the air unless supported by an external force) and yet has sufficiently large particles (greater than approximately 1, 2, 3, 4, 5, 10, 15 or 20 microns) such that few or no particles enter the lungs on inspiration, our technology results in oral deposition and oral/buccal delivery. Ideally, the particles would be engineered and produced such that, for example, at least about 50%, at least about 60%, at least about 70%, at least about 80%, at least about 90%, at least about 95%, at least about 97%, or at least about 99% of the particles deposit in the mouth and do not extend further into the respiratory tract.

Particle engineering can also account for reducing any tendency to cough, gag, or otherwise react unfavorably to the aerosol. For example, some payload formulations may result in a mouth feel/oral sensation that is more pleasant with a range of particle sizes greater than about 50 microns but less than 100 microns. Therefore, in particular embodiments, the range of particle sizes is engineered to the specific particle payload formulation to optimize aerosolizablity, solubility, and membrane transport.

Additionally, particle payload median size distribution can be engineered for good performance in a particular aerosolizing device. For example, in certain embodiments a particle size distribution of a particular formulation for use in a disposable device may be numerically larger or smaller than the same formulation for use in a disposable cartridge and/or than for use in an edible cartridge or device. In other embodiments, the particle size distribution is chosen for required, maximal and/or consistent payload delivery per actuation of a particular device. For example, a single device or cartridge may be designed for carrying any class of formulations (i.e., a pharmaceutical, an OTC, an energy supplement, etc.), but the particle size distribution and formulation of different payloads results in different payload delivery amounts per actuation of the same device.

Dry powder particles can be created through a number of different methods. For example, certain products including food products be dehydrated, freeze dried, lyophilized, etc. Alternatively or in addition, where the food is a more malleable or liquid based food, the food may be frozen first to facilitate subsequent grinding or chopping. The food product may subsequently be ground to form particles (e.g., food particles) of the appropriate size. Grinding of the products can be performed by use of a mortar and pestle. Alternatively or in addition, products may be chopped, for example using a mechanical or electrical grinder, knives, etc. The resulting ground or chopped particles can subsequently be filtered through sieves (for example by hand, using an electrical or mechanical sieve shaker, by an air classification system, by a screening system, etc.) to achieve the appropriate particle size. Another approach is to use a powder mill that grinds down larger particles into pre-defined sizes. Spray drying, in which a mixture of water and the material to be dried is forced through a nozzle into a high-temperature drum, instantly evaporating the water droplets clinging to the material, may also be utilized. These methods, in addition to others, would allow for the creation of specifically sized particles capable of being aerosolized, but large enough not to pass easily through the mouth and throat and continue into the respiratory tract.

These dry powder particles could be created from a single product or ingredient of a composition, such as chocolate, coffee, or truffles, or from a combination of foods or ingredients, such as combinations representative of an entire dish or meal (e.g., mixed fruits, pizza, pastry, meat and potatoes, etc.). In the case of chocolate, chocolate bars, chocolate powder, cocoa powder, and other forms and varieties of foods derived from the cocoa plant may be used. In addition, in some cases, spices and other (natural or artificial) flavorings may be used alone or in combination with such food ingredients to create other tastes or sensations (e.g., natural or artificial chocolate, raspberry, mango, mint, vanilla, cinnamon, caramel, and/or coffee flavors). Additionally, the apparatus may contain a single dose of food product or multiple doses/portions of the food product. In addition, they may be made from largely liquid products, for example by extracting dissolved solids or using other solid components. In some embodiments, flavors can be experienced while using less of the actual product compared to normal ingestion. In addition, by mixing different powders, new flavors can be created.

Depending on the food product(s) and device(s) used, the food product may be stored and/or contained in the form of a tablet or pill, in a blister pack, within a capsule, as simply a powder in a jar-like container, and/or in a tray, box, container, thermos, bottle, etc.

In some embodiments, it is possible to deliver odors using appropriately designed and appropriately sized particles, which may be utilized independently or in addition to embodiments described herein, i.e., in addition to delivery of aerosolized food product so as to enhance the aesthetic experience.

"Food product", "aerosol", "particle", and other similar terms are used throughout this document, and though they may typically refer to small solid particles derived from foods, these terms may in some cases refer to any of the other edible products including, but not limited to, a food product, an energy supplement, a pharmaceutical compound, an over-the-counter pharmaceutical compound, a nutraceutical, a sleep-aid compound, a weight-loss compound, an oral health compound, etc.

Applications

Our apparatus can transform how ingestible aerosolizable payloads are experienced, allowing for an enhanced delivery and performance of ingestible products. For example, medicines can be delivered more effectively, and by having larger surface area to volume in the aerosolized payload, are likely to be transported through membrane barriers at higher kinetic efficiencies. Additionally, for food-based payloads, the aerosolizing apparatus can allow subjects to experience food either individually with hand held devices, or expose themselves to, for example, rooms filled with aerosolized clouds of various flavorings. The devices described herein can be applicable for compounds used for weight loss, OTC and pharmaceutical compound delivery (for example, allergy medicines, cold and flu medicines, etc.), nutraceuticals, dietary supplements, energy supplements, etc.

In some embodiments, the devices and methods described can allow subjects to experience food by exposing themselves to aerosolized food via individual, hand-held, and/or portable devices. In some embodiments, our technology may be used in and/or associated with social contexts similar to candy eating or cigarette smoking. For example, some embodiments may be carried about and used at various points throughout the day, or used simultaneously by multiple users.

In addition, the apparatus can serve to provide nutrition to subjects either who are incapable of chewing or for whom delivery of food is not convenient. For example, the particle delivery apparatus may be useful for elderly or young children, for whom chewing or feeding is inconvenient. In addition, individuals with medical conditions that require them to be fed in particular ways (e.g., by a feeding tube or intravenously) may use certain embodiments of this invention as a way to experience and taste food again.

In certain embodiments, the aerosolizing apparatus can serve to facilitate the intake of medication that may not be of a pleasurable taste. If used in conjunction with delivery of the medication, e.g. orally, the apparatus can provide an additional flavor that masks the flavor of the medication.

In some embodiments, the aerosolizing apparatus described herein may be used for weight control or addiction mitigation applications. For example, the aerosolizing apparatus can allow for subjects to consume relatively small or negligible quantities of food products or certain unhealthy or addictive substances, and the exposure to the particles (e.g., food particles, weight loss, nutraceuticals, etc.) via the apparatus may provide a sensation or satisfaction normally associated with the consumption of a larger quantity of the food or substance in question, thereby potentially satisfying hunger or addictive urges without the (potentially negative) consequences of actually consuming larger amounts of the substance(s). In some cases, this may be due to the higher surface area of the food product exposed to surfaces of the mouth, for example exposed to taste receptors, relative to the overall quantity (e.g., mass) of food product. Indeed, the particle delivery apparatus may form a basis for dieting, weight control and healthy eating programs (for example, by satisfying cravings for sweets, fatty foods, chocolate and caffeine) and addiction treatment (for example, by satisfying urges for alcohol, smoking, drugs but in much smaller, less harmful amounts).

Additionally, the particle delivery apparatus can serve as a means for taste-testing a number of items in a simple and efficient way. For example, a patron at a restaurant can taste test various dishes on the menu before making a selection. Additionally, chefs may use the particle delivery apparatus to test combinations of foods while cooking or designing a recipe. Similarly, the apparatus may serve as an aid in cooking lessons, as an international "dining" experience for a subject, as a way to teach children about food, etc. In addition, the particle delivery apparatus may be used to improve quality of life, for example, with respect to individuals subject to special dietary restrictions Other useful applications of the particle delivery apparatus include, but are not limited to hunger relief (e.g., in the emergency conditions of a famine) and for animal feedings.

Terms and phrases including "inhalable", "exhalable", "inhalation", "exhalation", "breathable", "respiration", "respirable", "aspiration", "inspiration", "expiration", "sip", "sipping", "sucking", and others, have been used throughout this disclosure—or could have been used, as exact or approximate equivalents—to describe certain aspects of the disclosed embodiments. It should be noted that the definitions of each of these terms and phrases must be understood based on context and other relevant information herein. The precise definitions as understood in certain fields (e.g., medicine, anatomy, mechanical engineering, etc.) may not always be applicable in part or in whole.

Throughout the disclosure, "mouthpiece" and "first member" have been used interchangeably to describe function and/or structure of the components of the aerosolizing device described herein, and should be understood as being interchangeable for the descriptions as provided.

In addition, throughout this disclosure, "aerosol", and similar terms (including singular and plural usages), are intended to refer to "a gaseous suspension of fine solid or liquid particles" ("aerosol" as defined in the American Heritage Dictionary online, 2011). For example, a dry powder that can be suspended in an air flow and transported via the airflow, as with the devices and payloads described herein, is considered to be within this definition. As another example, a plurality of liquid droplets substantially suspended in air as the result of ultrasonic agitation of a liquid, is also considered to be within this definition. Other examples of aerosols, and other relevant uses of such terms, would be evident to those skilled in the art; these examples and definition are therefore meant as clarification and in no way are intended to limit the scope or applicability of the terms as used herein.

EXAMPLES

Example 1

Figure 30:
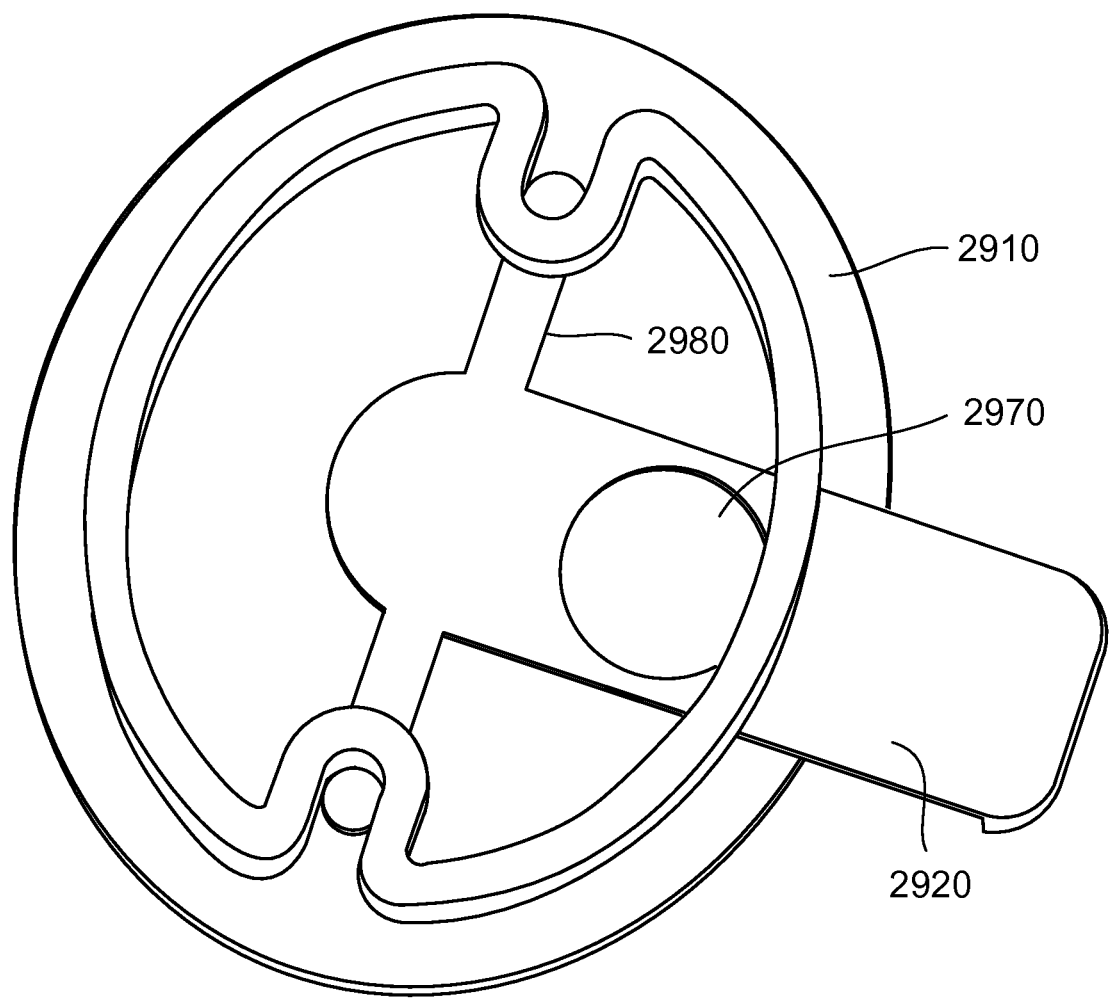
FIG. 30 illustrates a sprung door used to close air inlet ports and aerosol flow outlet ports on a replaceable cartridge for an aerosolizing delivery apparatus.

FIG. 30 shows a sprung door covering element 2910 which is used to enclose a replaceable, edible and/or biodegradable cartridge and serve as the abutting member to the first member or mouthpiece of an aerosolizing apparatus. Lever 2920 comprises a hole 2970 which is off center (e.g., not aligned with the outlet port of the cartridge) when the lever is in the unactuated, closed position. When pressed towards the body of the cartridge 2910 (acutated), lever member 2920 aligns the hole 2970 with the outlet port of the cartridge. Members 2980 can be separate spring members or spring portions integral with the lever 2920 as would be found with a living hinge.

Example 2

Figure 31B:
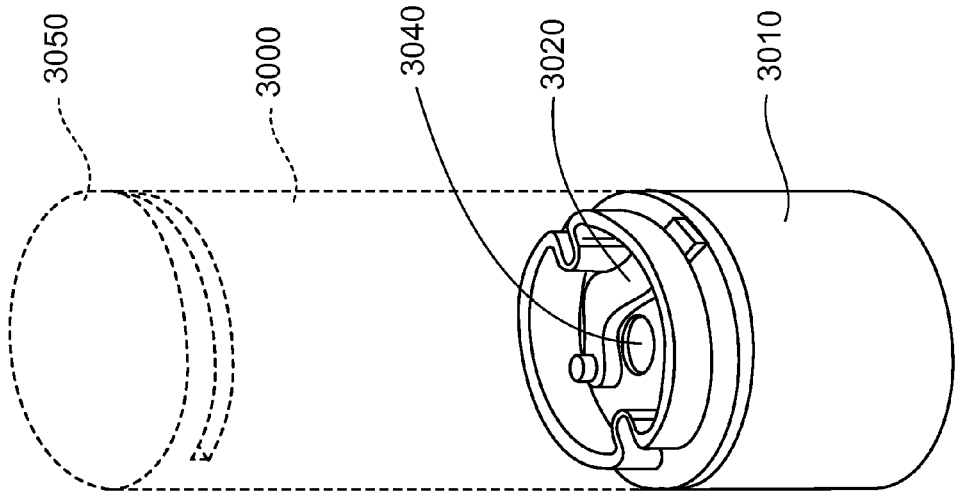
FIGS. 31A and 31B illustrate an aerosolizing delivery apparatus that includes a user-actuated slide lever used to close outlet ports on a replaceable cartridge.
Figure 31A:
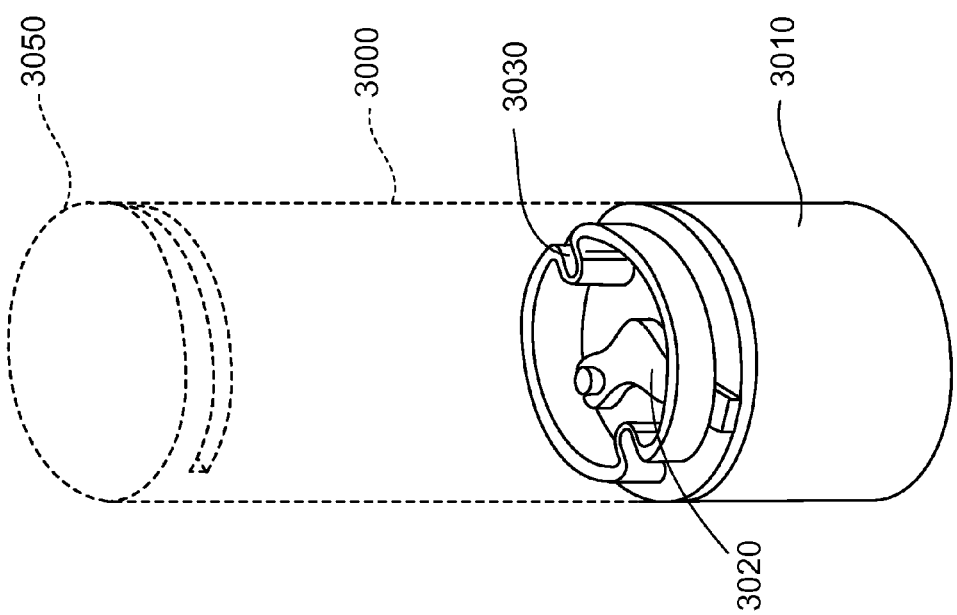

FIGS. 31a and 31b illustrate a replaceable cartridge 3010 with a sealing or closing mechanism 3020 in an aerosolizing delivery apparatus. The apparatus comprises a first member (or mouthpiece) 3000 detachably connected to a replaceable, edible and/or biodegradable cartridge 3010 that contains aerosolizable powder. A deflection member 3050 is located on an end of the first member 3000 opposed to the cartridge 3010 and is configured to redirect aerosolized particles to the sides of a user's mouth upon actuation of the apparatus. The air intake ports 3030 and aerosol flow outlet port 3040 direct aerosolized powder towards the deflection member 3050. In the closed configuration shown in FIGS. 30 a and b, the slide lever 3020 covers the outlet port, preventing air from flowing into the chamber through air intake port 3030, and prevents powder from becoming aerosolized and exiting the cartridge through outlet port 3040. FIG. 30 b shows a cartridge and slide lever in the open position, with outlet port 3040 uncovered. Slide lever 3020 is designed to be sprung or passive, and has an end that protrudes outward from the apparatus to permit manual actuation between the closed configuration and the open configuration.

Example 3

FIGS. 32a-32d illustrate a replaceable cartridge 3110 with a sealing or closing door 3180 actuated by a separate lever mechanism 3120 in an aerosolizing delivery apparatus. The apparatus comprises a first member (or mouthpiece) 3100 detachably connected to a replaceable, edible and/or biodegradable cartridge 3110 that contains aerosolizable powder. The air intake ports 3130 and aerosol flow outlet port 3170 direct aerosolized powder towards the mouthpiece 3100. In the closed configuration shown in FIGS. 32 a and 32b, the door or cover 3180 overlies the cartridge outlet port 3170 and prevents air from flowing into the first member chamber through air intake port 3130 and prevents powder from becoming aerosolized and exiting the cartridge through outlet port 3170. FIGS. 32 c and 32d shows the cartridge 3110 with the door 3180 in the open position, in which the door is pushed away from the cartridge outlet port 3170 by the lever mechanism 3120, leaving the outlet port 3170 uncovered. The door 3180 may pivot or bend to achieve the configuration shown in FIGS. 30c and 30d. The closing/opening lever 3120 is designed to be sprung or passive, and lockable in the open position. An end of the lever 3120 protrudes outward from the apparatus to permit manual actuation between the closed configuration and the open configuration.

Example 4

Figure 33B:
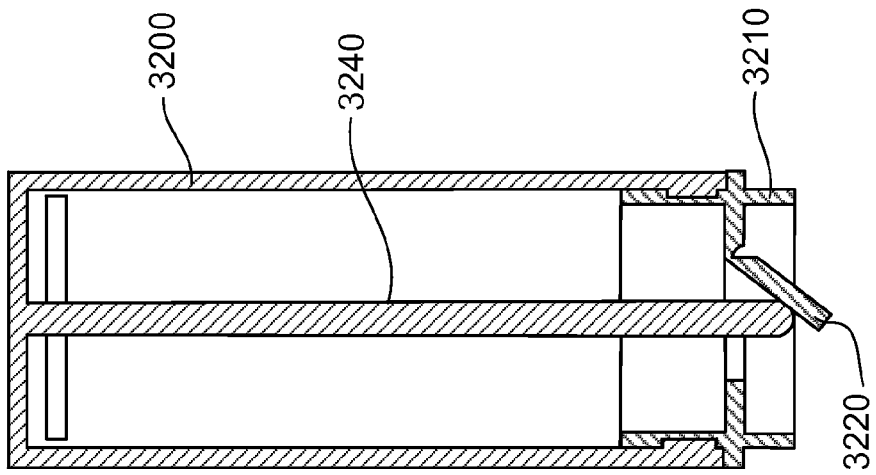
FIGS. 33A and 33B illustrate an aerosolizing delivery apparatus that includes a twist- or compression-actuated flexible door used to close outlet ports on a replaceable cartridge.
Figure 33A:
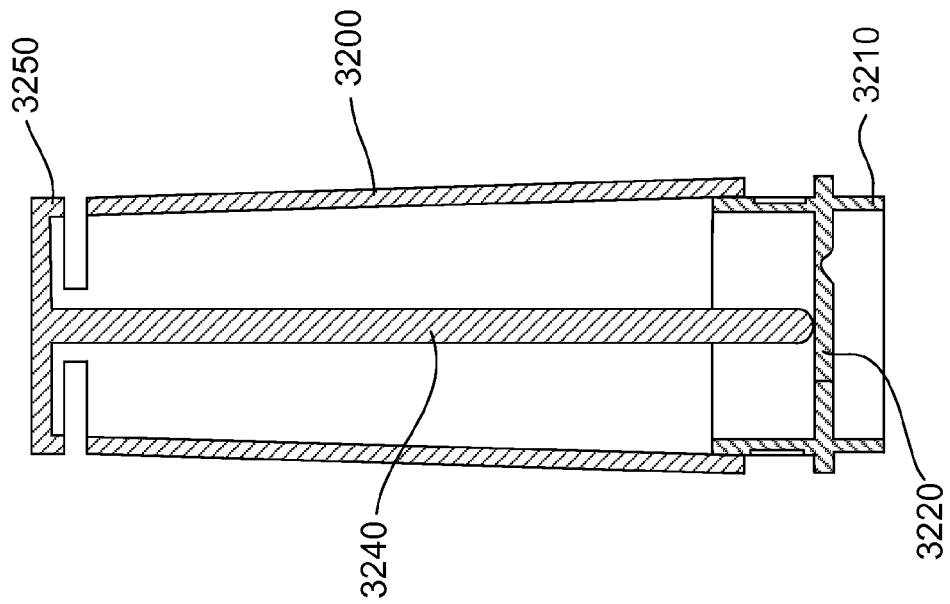

FIGS. 33a and 33b illustrate a replaceable, edible and/or biodegradable cartridge 3210 with a sealing or closing door 3220 actuated by a separate post configuration in an aerosolizing delivery apparatus 3200. The apparatus comprises a first member (or mouthpiece) 3200 detachably connected to a replaceable cartridge 3210 that contains aerosolizable powder. A deflection member 3250 is located on an end of the first member 3200 opposed to the cartridge 3210 and is configured to redirect aerosolized particles to the sides of a user's mouth upon actuation of the apparatus. In the closed configuration shown in FIGS. 33 a, the door or cover 3220 obstructs an outlet port of the cartridge 3210, and thus prevents air from flowing into the chamber through air intake ports and prevents powder from becoming aerosolized and exiting the cartridge through outlet port. In some embodiments, the door or cover 3220 is a flap formed integrally with a top surface of the cartridge. FIG. 33 b shows the cartridge 3210 with the door 3220 in the open position whereby the outlet port is uncovered. The door 3220 is opened by moving the first member 3200 toward the cartridge 3210 whereby the post 3240 provided in the first member 3200 urges the door 3220 into the open configuration. The closing/opening lever is designed to be sprung or passive, and lockable in the open position.

Example 5

Figure 34B:
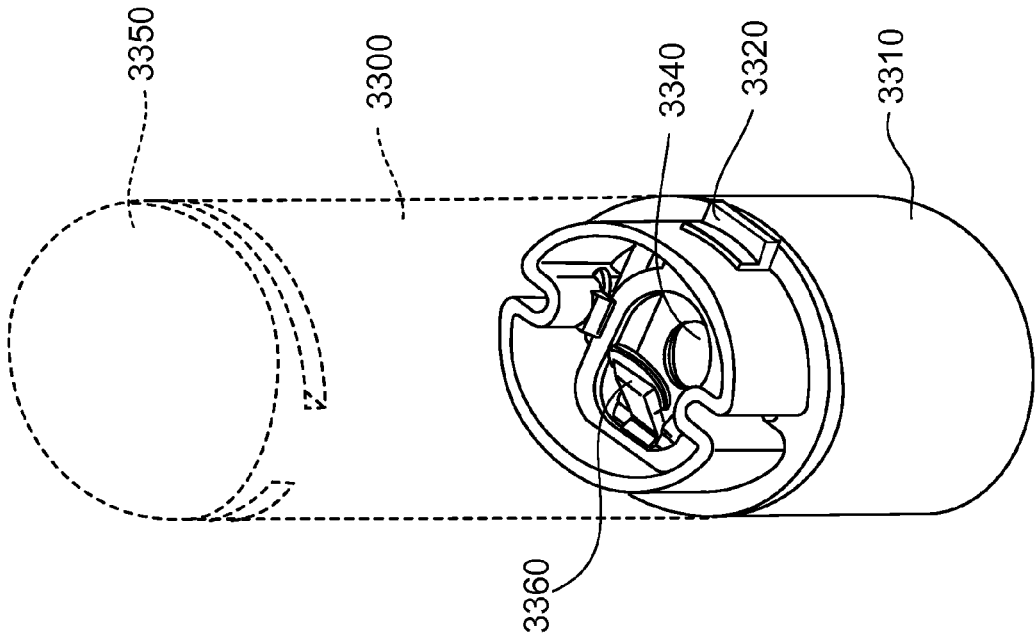
FIGS. 34A and 34B illustrate an aerosolizing delivery apparatus that includes a user-actuated flexible door employing a living hinge and used to close inlet and outlet ports on a replaceable cartridge.
Figure 34A:
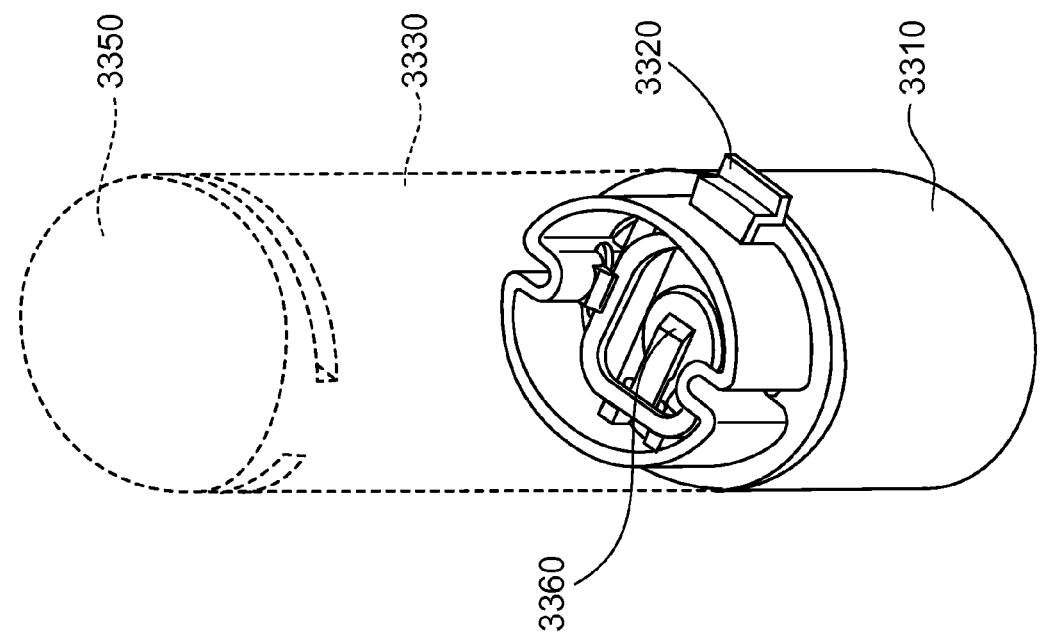
Figure 36B:
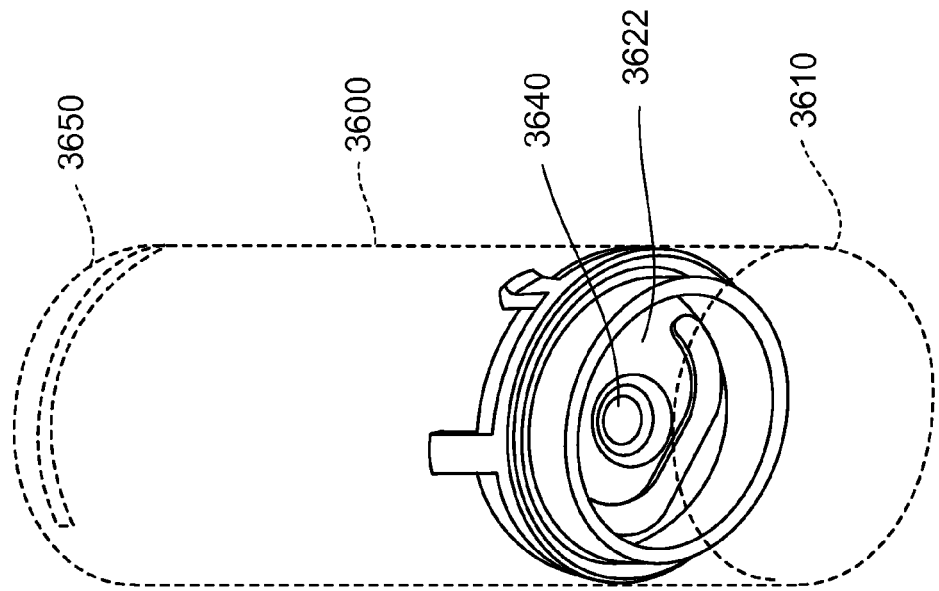
FIGS. 36A and 36B illustrate an aerosolizing delivery apparatus that includes a unidirectional dual flapper valve used to close inlet and outlet ports on a replaceable cartridge for an aerosolizing delivery apparatus.
Figure 36A:
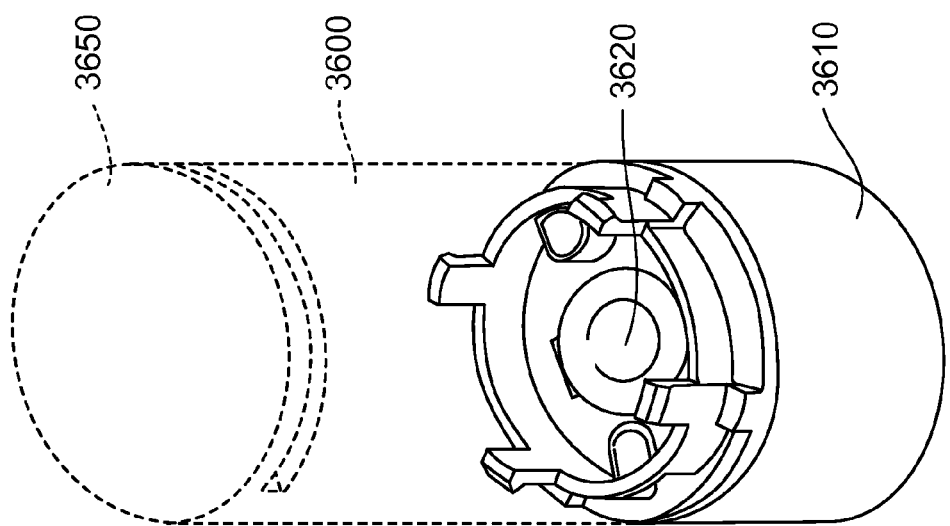
Figure 37D:
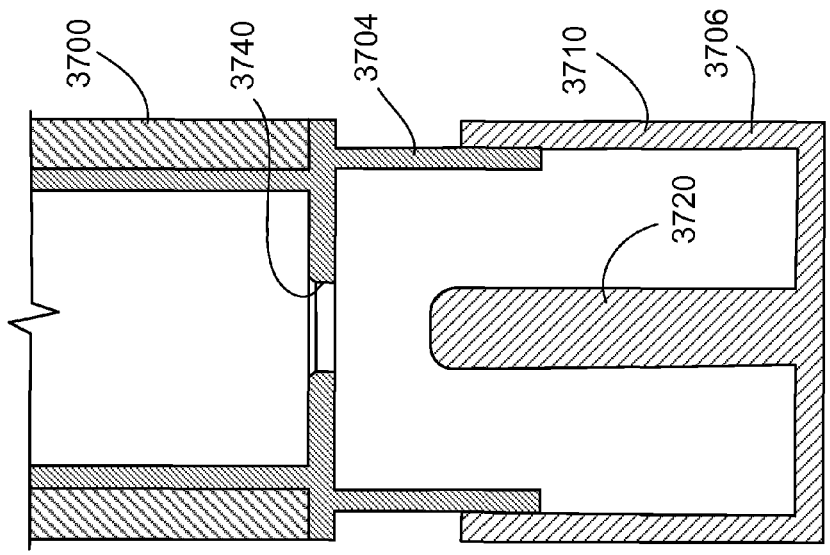
Figure 37C:
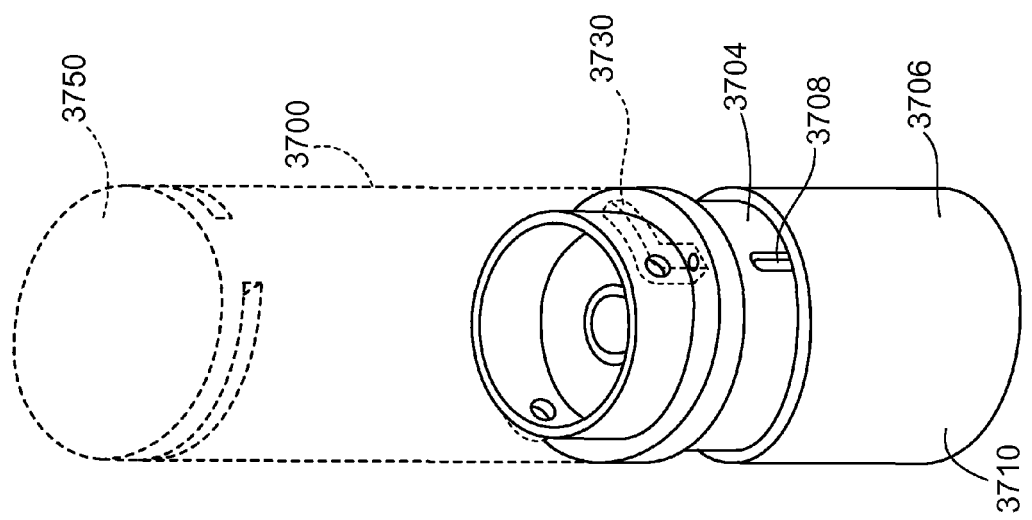
Figure 38:
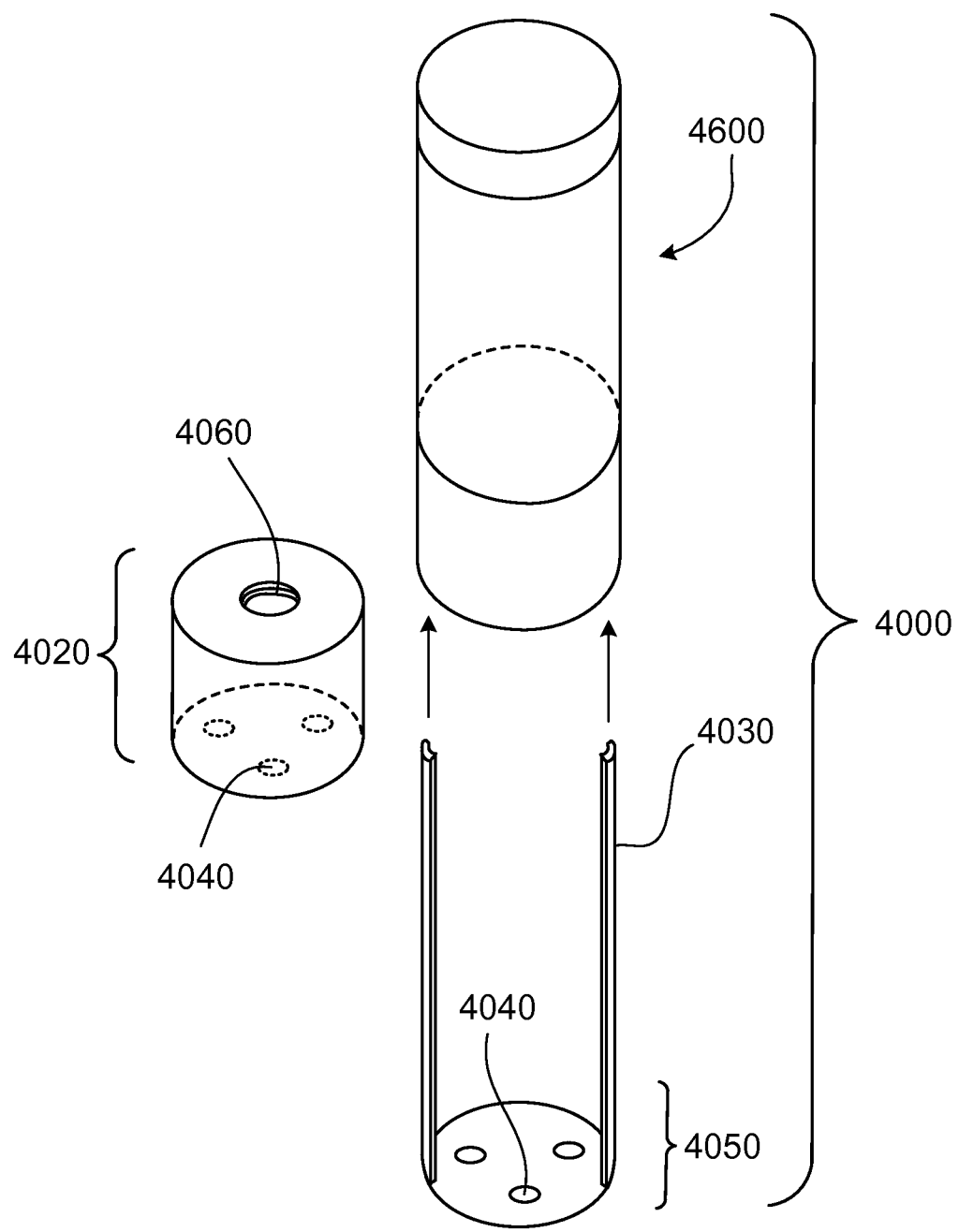
FIG. 38 illustrates an aerosolizing delivery apparatus that includes a mounting carriage used for supporting an edible cartridge relative to a mouthpiece.

FIGS. 34a and 34b illustrate a replaceable, edible and/or biodegradable cartridge 3310 with a sealing or closing door 3360 actuated by a living hinge mechanism in an aerosolizing delivery apparatus 3300. The apparatus comprises a first member (or mouthpiece) 3300 detachably connected to a replaceable cartridge 3310 that contains aerosolizable powder. A deflection member 3350 is located on an end of the first member 3300 opposed to the cartridge 3310 and is configured to redirect aerosolized particles to the sides of a user's mouth upon actuation of the apparatus. In the closed configuration shown in FIG. 34a, the door or cover is disposed on an outer surface of the cartridge, and prevents air from flowing into the chamber through air intake ports 3330 and prevents powder from becoming aerosolized and exiting the cartridge through outlet port 3340. FIG. 34b shows a cartridge 3310 and door 3360 in the open position, with outlet port uncovered. The closing/opening lever is designed to be sprung or passive with button or lever 3320, and lockable in the open position. An end of the lever 3320 protrudes outward from the apparatus to permit manual actuation between the closed configuration and the open configuration.

Example 6

FIGS. 35a and 35b illustrate a replaceable, edible and/or biodegradable cartridge 3410 with a sealing one way duck bill valve 3420, actuated by a digital manipulation, in an aerosolizing delivery apparatus 3400. The apparatus comprises a first member (or mouthpiece) 3400 detachably connected to a replaceable cartridge 3410 that contains aerosolizable powder. A deflection member 3450 is located on an end of the first member 3400 opposed to the cartridge 3410 and is configured to redirect aerosolized particles to the sides of a user's mouth upon actuation of the apparatus. In the closed configuration shown in FIG. 35*a*, the valve prevents air from flowing from the chamber through outlet ports, and prevents powder from becoming aerosolized and exiting the cartridge. FIG. 35*b* shows a cross sectional view of the cartridge 3410 and valve 3420 in the closed position, with outlet port uncovered. The closing/opening actuation is achieved by squeezing the ends of the valve through the side opening 3415 of the cartridge as seen in FIG. 35*a*.

Example 7

FIGS. 36*a* and 36*b* illustrate a replaceable, edible and/or biodegradable cartridge 3610 with a sealing one way dual flapper valve 3620, actuated by inhalation/inspiration, in an aerosolizing delivery apparatus 3600. The apparatus comprises a first member (or mouthpiece) 3650 detachably connected to a replaceable cartridge 3610 that contains aerosolizable powder. A deflection member 3650 is located on an end of the first member 3600 opposed to the cartridge 3610 and is configured to redirect aerosolized particles to the sides of a user's mouth upon actuation of the apparatus. In the closed configuration, the valve 3620 prevents air from flowing from the chamber through outlet ports 3640, and prevents powder from becoming aerosolized and exiting the cartridge. FIG. 36*b* shows an underside (or cartridge) view of the bottom 3510 and bottom flapper valve 3622 in the closed position, with outlet port 3640 covered.

Example 8

FIG. 37 shows a replaceable, edible and/or biodegradable cartridge with a post-in-hole sealing or closing mechanism in an aerosolizing delivery apparatus. The apparatus comprises a first member (or mouthpiece) 3700 detachably connected to a replaceable cartridge 3710 that contains aerosolizable powder. A deflection member 3750 is located on an end of the first member 3700 opposed to the cartridge 3710 and is configured to redirect aerosolized particles to the sides of a user's mouth upon actuation of the apparatus. The air intake ports 3708 and aerosol flow outlet port 3740 direct aerosolized powder towards the deflection member 3750. The cartridge 3710 includes a cartridge inner member 3704 and an outer member 3706, which are slidably connected. In the open configuration shown in FIGS. 37*c* and 37*d*, the inner member 3704 telescopes upward and partially out of the outer member 3706, whereby the cartridge outlet port 3740 is open. The inner member 3704 slides relative to the outer member 3706 such that pushing the outer member 3706 up into the inner member 3704 brings a free end of the post 3720 into outlet port 3740, whereby the cartridge is in the closed configuration, and the outlet port 3740 is sealed. The post-in-hole configuration prevents air from flowing into the chamber of the first member through air intake port 3708 by covering the opening to the air intake portal with the upper edge of outer member 3706. A closed orientation prevents powder from becoming aerosolized and exiting the cartridge through outlet port 3740 or spilled from the air inlet ports 3708. FIG. 37 *b* and *d* shows a cross sectional view of cartridge 3710 and post orientation in the closed (FIG. 37 *b*.) and open (FIG. 37 *d*) positions. Also shown in FIG. 37 *c* are orientation guides 3730 for the slidable member, which also aid in attaching the cartridge to the mouthpiece.

Example 9

FIG. 38 illustrates an example of an aerosolizing apparatus 4000. The apparatus includes a first member (or mouthpiece) 4600 detachably connected to a mounting carriage 4050 that supports a replaceable, edible and/or biodegradable cartridge 4020 that contains aerosolizable powder. A deflection member is located on a first end of the first member 4600 opposed to the mounting carriage 4050 and is configured to redirect aerosolized particles to the sides of a user's mouth upon actuation of the apparatus. Mounting carriage 4050 connects with the mouthpiece or first member 4600 with dowels, pins, prongs, magnets, etc., 4030. Openings 4040 can be present in the bottom of the mounting carriage 4050 when using edible cartridges 4020. Edible cartridges can have at least one outlet port 4060, be sized to be press fit into the first member 4600, and/or be held in place adjoining the first member 4600 by the mounting carriage 4050. In certain examples, puncture prongs are mounted to a carrying case designed to carry the apparatus with or without at least one edible cartridge. The prongs mounted to the case are then used to create small air inlet holes 4040 in the edible cartridge 4020 by puncturing the bottom of the edible cartridge 4020. The holes 4040 in the bottom of the mounting carriage can be used to align the cartridge 4020 with the prongs in the carrying case. The mounting carriage and edible cartridge are then detachably connected to the mouthpiece, wherein a user inhales preloaded powder via the first member. In addition to inhalation, the user can eat the edible cartridge for a full flavor experience. For example, candies and chocolates can be press molded into a cartridge, breads or crusts can be used for cartridge material and loaded with lyophilized or freeze dried powders processed from, for example, sandwiches, pizzas, meats, etc.

What is claimed is:

1. A cartridge configured to be detachably connected to a delivery device, the cartridge comprising:

a housing defining a reservoir and a cartridge outlet, the cartridge outlet configured to permit fluid communication between the reservoir and an exterior of the cartridge, wherein the cartridge is configured to form a junction with the delivery device when the cartridge is assembled with the delivery device and an outer surface of the housing defines a flat region that is configured to define a bypass port at the junction between the outer surface of the housing and a surface of the delivery device to permit air flow into the delivery device.

2. The cartridge of claim 1, wherein, when connected to the delivery device, the cartridge outlet is configured to be in fluid communication with an inlet of the delivery device.

3. The cartridge of claim 1, wherein the housing defines a cartridge inlet that is in fluid communication with air exterior to the device.

4. The cartridge of claim 3, wherein the cartridge inlet is in fluid communication with an interior space of the delivery device.

5. The cartridge of claim 3, wherein the cartridge comprises a closing mechanism operatively connected to at least one of the cartridge inlet and the cartridge outlet.

6. The cartridge of claim 5, wherein the closing mechanism is at least one of a post-in-hole structure, a spring-actuated door, a slide lever, a living hinge, a flap valve, a unidirectional valve, or combinations thereof.

7. The cartridge of claim 5, further comprising an actuator operatively connected to the closing mechanism.

8. The cartridge of claim 1, wherein the cartridge comprises an inner member, and an outer member slidably interconnected to the inner member to define the reservoir.

9. The cartridge of claim 8, wherein the housing defines a cartridge inlet that is in fluid communication with air exterior to the device, and
wherein the inner member is movable relative to the outer member, between a first position wherein at least one of the cartridge air inlet and the cartridge outlet are open, and a second position wherein at least one of the cartridge air inlet and the cartridge outlet are closed.

10. The cartridge of claim 9, wherein movement of the inner member relative to the outer member actuates at least one of an air inlet closing mechanism and an outlet closing mechanism.

11. The cartridge of claim 1, wherein the cartridge is configured to be detachably connected to the delivery device by a mounting carriage, a press fit, a magnetic retaining mechanism, a twist mechanism, a snap mechanism, a screw mechanism, a bayonet mount mechanism, or combinations thereof.

12. The cartridge of claim 1, wherein the cartridge reservoir has a volume capacity of between about ten (10) milligrams to about two (2) grams of a product.

13. The cartridge of claim 1, wherein, when connected to the delivery device, the cartridge and delivery device cooperate to provide a flow rate of between about ten (10) liters per minute and about sixty (60) liters per minute at a vacuum pressure of about four kiloPascals.

14. The cartridge of claim 1, wherein the reservoir has a variable volume.

15. The cartridge of claim 1, comprising:
a delivery device connection portion and
a base portion assembled with the delivery device connection portion to define the reservoir within the cartridge, the delivery device connection portion being moveable relative to the base portion between a first position in which the reservoir has a first volume, and a second position in which the reservoir has a second volume,
wherein when the cartridge is in the first position, the cartridge outlet is open so as to permit fluid communication between the reservoir and the exterior of the cartridge via the cartridge outlet, and when the cartridge is in the second position, the cartridge outlet is closed.

16. The cartridge of claim 1, wherein the cartridge is at least one of edible or biodegradable.

17. The cartridge of claim 1, wherein the cartridge is biodegradable and is formed of at least one of a polyester, a polyhydroxyalkanoate, a polyanhydride, a polycaprolactone, a polydiaxonone, a polyglycolide, a polyhydroxybutyrate, a polylactic acid, a polypropylene carbonate, a polylactic-co-glycolic acid, a poly(3-20 hydroxybutyrate-co-3-hydroxyvalerate), a polyvinyl alcohol, a starch derivative, a cellulose derivative, a cellulose ester, a cellophane, an enhanced biodegradable plastic, compositional variants thereof, or combinations thereof.

18. The cartridge of claim 1, the cartridge further comprising:
external screw threads on the housing configured to engage corresponding screw threads defined on the delivery device, and
the flat region on the surface of the housing, located adjacent the screw threads, and configured to be located at the junction when the cartridge is assembled with the delivery device and define the bypass port to permit air flow into the delivery device.

19. A cartridge for a delivery device, the cartridge comprising:
a connection portion configured to be detachably connected to the delivery device, the connection portion including a first end having an outlet, and a first sidewall disposed about the first end defining an outer surface, the outer surface of the connection portion first sidewall comprises a flat region configured to define a bypass port between the connection portion and the delivery device when the cartridge is connected to the delivery device, and
a base portion, the base portion including a second end, a second sidewall disposed about the second end, and a post extending from the second end in parallel with the second sidewall so that at least a portion of the post is surrounded by the second sidewall,
wherein the connection portion is engaged with the base portion to define a reservoir between the first end and the second end, and
the connection portion is moveable relative to the base portion between a first position in which the outlet is open such that fluid communication exists between the reservoir and the exterior of the cartridge, and a second position in which the post is positioned within the outlet so as to close the outlet.

20. The cartridge of claim 19, further comprising external screw threads on the housing adjacent the flat region and configured to engage corresponding screw threads defined on the delivery device.

21. The cartridge of claim 19, wherein the reservoir has a variable volume.

22. The cartridge of claim 19, wherein the connection portion is engaged with the base portion such that when the connection portion is in the first position, an air inlet is formed between the connection portion and the base portion.

23. A cartridge and a delivery device:
the cartridge comprising a housing defining a reservoir and a cartridge outlet, the cartridge outlet configured to permit fluid communication between the reservoir and an exterior of the cartridge,
the housing forming a junction with the delivery device and an outer surface of the housing defining a flat region defining a bypass port between the outer surface of the housing and the delivery device at the junction to permit air flow into the delivery device.

24. The cartridge and delivery device of claim 23, further comprising external screw threads on the housing adjacent the flat region, the external screw threads configured to engage corresponding screw threads defined on the delivery device at the junction.

* * * * *